United States Patent
Dou et al.

(10) Patent No.: US 7,635,693 B2
(45) Date of Patent: *Dec. 22, 2009

(54) METHODS FOR PREVENTING AND TREATING CANCER USING N-THIOLATED β-LACTAM COMPOUNDS AND ANALOGS THEREOF

(75) Inventors: Q. Ping Dou, Tampa, FL (US); Edward Turos, Wesley Chapel, FL (US); David M. Smith, Boston, MA (US)

(73) Assignee: University of South Florida, Tampa, FL (US)

( * ) Notice: Subject to any disclaimer, the term of this patent is extended or adjusted under 35 U.S.C. 154(b) by 546 days.

This patent is subject to a terminal disclaimer.

(21) Appl. No.: 11/374,814

(22) Filed: Mar. 14, 2006

(65) Prior Publication Data
US 2006/0160787 A1 Jul. 20, 2006

Related U.S. Application Data

(62) Division of application No. 10/431,113, filed on May 6, 2003, now Pat. No. 7,026,472.

(60) Provisional application No. 60/377,604, filed on May 6, 2002.

(51) Int. Cl.
A61K 31/397 (2006.01)
C07D 205/08 (2006.01)
A61P 37/06 (2006.01)

(52) U.S. Cl. .................... 514/210.15; 424/9.2
(58) Field of Classification Search ............ 514/210.15
See application file for complete search history.

(56) References Cited

U.S. PATENT DOCUMENTS 4,938,949 A 7/1990 Borch et al.
5,142,039 A 8/1992 Blaszczak et al.
5,338,861 A 8/1994 Botta et al.
6,476,015 B1* 11/2002 Turos et al. ............ 540/355
6,946,458 B2 9/2005 Turos
2003/0191108 A1 10/2003 Turos

OTHER PUBLICATIONS

Coates, Bioorganic & Medicinal Chemistry, vol. 11, Issue 2, Jan. 2003, pp. 193-196.*

(Continued)

Primary Examiner—Mark L Berch
(74) Attorney, Agent, or Firm—Saliwanchik, Lloyd & Saliwanchik

(57) ABSTRACT

The subject invention concerns N-thiolated β-lactam compounds of formula A,

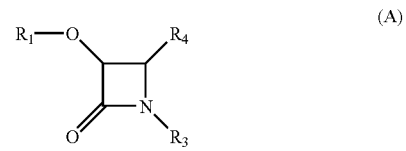

(A)

wherein $R_1$ is a hydrocarbon group having 1-8 carbon atoms; $R_3$ is an organothio group; and $R_4$ is alkyl, alkenyl, alkynyl, aryl, heteroaryl, cycloalkyl, heterocycloalkyl, cycloalkenyl, or heterocycloalkenyl, and analogs and pharmaceutically acceptable salts, esters and amides thereof. The subject invention also concerns methods for inducing tumor cell death or inhibiting tumor cell proliferation, and methods for inducing DNA damage, inhibiting DNA replication, activating p38 MAP kinase, or activating caspase cascade activation, or releasing cytochrome C from mitochondria into the cytoplasm in a tumor cell. Methods for treating cancer using N-thiolated β-lactam compounds, as well as pharmaceutical compositions comprising the same are further disclosed.

37 Claims, 26 Drawing Sheets

OTHER PUBLICATIONS

An, B. and Q. P. Dou "Cleavage of Retinoblastoma Protein during Apoptosis: An Interleukin 1β-converting Enzyme-like Protease as Candidate," *Cancer Research*, Feb. 1, 1996, vol. No. 56, pp. 438-442.

An, B. et al. "Novel dipeptidyl proteasome inhibitors overcome Bcl-2 protective function and selectivity accumulate the cyclin-dependent kinase inhibitor p27 and induce apoptosis in transformed, but not normal, human fibroblasts," *Cell Death and Differentiation*, 1998, vol. No. 5, pp. 1062-1075.

Desoize, B. "Anticancer Drug Resistance and Inhibition of Apoptosis," *Anticancer Research*, 1994, vol. No. 14, pp. 2291-2294.

Dou, Q. P. "Putative roles of retinoblastoma protein in apoptosis," *Apoptosis*, 1997, vol. No. 2, Issue No. 1, pp. 5-18.

Drexler, H. G. et al. "Continuous hematopoietic cell lines as model systems for leukemia—lymphoma research," *Leukemia Research*, 2000, vol. No. 24, pp. 881-911.

Earnshaw, W. C. "Nuclear changes in apoptosis," *Current Opinion in Cell Biology*, 1995, vol. No. 7, pp. 337-343.

Fattman, C. L. et al. "Sequential two-step cleavage of the retinoblastoma protein by caspase-3/-7 during etoposide-induced apoptosis," *Oncogene*, 2001, vol. No. 20, pp. 2918-2926.

Fisher, D. E. "Apoptosis in Cancer Therapy: Crossing the Threshold," *Cell*, Aug. 26, 1994, vol. No. 78, pp. 539-542.

Gao, G. and Q. P. Dou "N-Terminal Cleavage of Bax by Calpain Generates a Potent Proapoptotic 18-kDa Fragment that Promotes Bcl-2-Independent Cytochrome C Release and Apoptotic Cell Death," *Journal of Cellular Biochemistry*, 2000, vol. No. 80, pp. 53-72.

Green, D. R. and J. C. Reed "Mitochondria and Apoptosis," *Science*, Aug. 28, 1998, vol. No. 281, pp. 1309-1312.

Harrison, D. J. "Molecular Mechanisms of Drug Resistance in Tumours," *Journal of Pathology*, 1995, vol. No. 175, pp. 7-12.

Jänicke, R. U. et al. "Specific cleavage of the retinoblastoma protein by an ICE-like protease in apoptosis," *The EMBO Journal*, 1996, vol. No. 15, Issue No. 24, pp. 6969-6978.

Kummer, J. L. et al. "Apoptosis Induced by Withdrawal of Trophic Factors is Mediated by p38 Mitogen-activated Protein Kinase," *The Journal of Biological Chemistry*, 1997, vol. No. 272, Issue No. 33, pp. 20490-20494.

Lazebnik, Y. A. et al. "Cleavage of poly(ADP-ribose) polymerase by a proteinase with properties like ICE," *Nature*, Sep. 22, 1994, vol. No. 371, pp. 346-347.

Lee, S. et al "Apoptosis and signal transduction: clues to a molecular mechanism," *Current Opinion in Cell Biology* 1993, vol. No. 5, pp. 286-291.

Li, H. et al. "Cleavage of BID by Caspase 8 Mediates the Mitochondrial Damage in the Fas Pathway of Apoptosis," *Cell*, Aug. 21, 1998, vol. No. 94, pp. 491-501.

Martin, S. J. and D. R. Green "Protease Activation during Apoptosis: Death by a Thousand Cuts?" *Cell*, Aug. 11, 1995, vol. No. 82, pp. 349-352.

Menter, D. G. et al "Selenium Effects on Prostate Cell Growth," *Cancer Epidemiology, Biomarkers & Prevention*, Nov. 2000, vol. No. 9, pp. 1171-1182.

Nam, S. et al "Ester Bond-containing Tea Polyphenols Potently Inhibit Proteasome Activity in Vitro and in Vivo," *The Journal of Biological Chemistry*, Apr. 20, 2001, vol. No. 276, Issue No. 16, pp. 13322-13330.

Pfundt, R. et al. "In situ demonstration of phosphorylated c-jun and p38 MAP kinase in epidermal keratinocytes following ultraviolet B irradiation of human skin," *Journal of Pathology*, 2001, vol. No. 193, pp. 248-255.

Raingeaud, J. et al. "Pro-inflammatory Cytokines and Environmental Stress Cause p38 Mitogen-activated Protein Kinase Activation by Dual Phosphorylation on Tyrosine and Threonine," *The Journal of Biological Chemistry*, Mar. 31, 1995, vol. No. 270, Issue No. 13, pp. 7420-7426.

Ren, X. et al. "Studies on Nonconventionally Fused Bicyclic β-Lactams," *J. Org. Chem.*, 1998, vol. No. 63, pp. 8898-8917.

Sanchez-Prieto, R. et al. "A Role for the p38 Mitogen-activated Protein Kinase Pathway in the Transcriptional Activation of p53 on Genotoxic Stress by Chemotherapeutic Agents," *Cancer Research*, May 1, 2000, vol. No. 60, pp. 2464-2472.

Smith, D. M. and Q. P. Dou "Green tea polyphenol epigallocatechin inhibits DNA replication and consequently induces leukemia cell apoptosis," *International Journal of Molecular Medicine*, 2001, vol. No. 7, pp. 645-652.

Smith, D. M. et al. "A Novel β-Lactam Antibiotic Activates Tumor Cell Apoptotic Program by Inducing DNA Damage," *Molecular Pharmacology*, 2002, vol. No. 61, Issue No. 6, pp. 1348-1358.

Staudinger, H. "Diphenylketen," Mittheilungen aus dem chemischen Institut der Universitat Strassburg i. E., *Zur Kenntniss der Ketene*, 1907 (1$^{st}$ edition), pp. 51-123.

Thornberry, N. A. and Y. Lazebnik "Caspases: Enemies Within," *Science*, Aug. 28, 1998, vol. No. 281, pp. 1312-1316.

Turos, E. et al "N-Thiolated Bicyclic and Monocyclic β-Lactams," *Tetrahedron*, 2000, vol. No. 56, pp. 5571-5578.

Watabe, M. et al. "MT-21 is a Synthetic Apoptosis Inducer that Directly Induces Cytochrome c Release from Mitochondria," *Cancer Research*, Sep. 15, 2000, vol. No. 60, pp. 5214-5222.

Wu, G. Y. and C. H. Wu "Receptor-mediated in Vitro Gene Transformation by a Soluble DNA Carrier System," *The Joumal of Biological Chemistry*, Apr. 5, 1987, vol. No. 262, Issue No. 10, pp. 4429-4432.

Binder, S. et al. "Emerging Infectious Diseases: Public Health Issues for the 21$^{st}$ Century" *Science*, May 21, 1999, vol. No. 284, pp. 1311-1313.

Boyd, D.B. et al. "Heteroatom-Activated β-Lactam Antibiotics: Considerations of Differences in the Biological Activity of [[3(S)-(Acylamino)-2-oxo-1-azetidinyl]oxy]acetic Acids (Oxamazins) and the Corresponding Sulfur Analogues (Thiamazins)" *J. Med. Chem.*, 1987, vol. No. 30, pp. 528-536.

Breuer, H. et al. "[(2-oxo-1-azetidinyl)oxy]acetic Acids: A New Class of Synthetic Monobactams" *J. Antibiotics*, Jun. 1985, vol. No. 38, Issue No. 6, pp. 813-818.

Champney, W.S. and C.L. Tober "Evernimicin (SCH27899) Inhibits both Translation and 50S Ribosomal Subunit Formation in *Staphylococcus aureus* Cells" *Antimicrob. Agents and Chemotherapy*, Jun. 2000, vol. No. 44, Issue No. 6, pp. 1413-1417.

Lim, D.V. et al. "Radiolabeling of and Macromolecular Syntheses in *Neissetia gonorrhoeae* Types 1 and 4" *Applied and Envion. Microbiology*, Feb. 1977, vol. No. 33, Issue No. 2, pp. 328-333.

Long, T.E. and E. Turos "N-Thiolated β-Lactams" *Curr. Med. Chem.-Anti-Infective Agents*, 2002, vol. No. 1, Issue No. 3, pp. 251-268.

Slusarchyk, W.A. et al. "Monobactams: Ring Activating N-1-Substituents in Monocyclic β-Lactam Antibiotics" *Heterocycles*, 1984, vol. No. 21, Issue No. 1, pp. 191-209.

Sykes, R.B. et al. "Monocydicβ-lactam antibiotics produced by bacteria" *Nature*, Jun. 11, 1981, vol. No. 291, pp. 489-491.

Turos, E. et al. "N-Thiolated Bicyclic and Monocyclic β-Lactams" *Tetrahedron*, 2000, vol. No. 56, pages 5571-5578.

Turos, E. et al. "N-Thiolated β-Lactams: Novel Antibacterial Agents for Methicillin-Resistant *Staphylococcus aureus* " *Bioorganic & Med. Chem. Letters*, 2002, vol. No. 12, pp. 2229-2231.

Woulfe, S.R. and M.J. Miller "The Synthesis of Substituted [[3(S)-(Acylamino)-2-oxy-1-azetidinyl]thio]acetic Acids" *J. Org. Chem.*, 1986, vol. No. 51, pp. 3133-3139.

Hawley, G. et al. "The Condensed Chemical Dictionary", 1977, p. 498, Van Nostrand Reinhold Co., New York.

Roberts, J.D. and M.C. Caserio "Basic Principles of Organic Chemistry", 1964, Chapter 16, p. 529, W.A. Benjamin, Inc., New York.

Burnett, D.A. et al. "β-Lactams from Esters and Sulfenimines: A New Route to Monobactams" *J. Org. Chem.*, 1986, vol. No. 51, Issue No. 10, pp. 1929-1930.

Shah, N. V. and L.D. Cama "Synthesis of a Novel Carbapenem-Potassium (5R,6R)-1, 1-Difluoro-2-Phenyl-6-(1R-Hydroxyethyl)-Carbapen-2EM-3-Carboxylate. The Use of New N-Protecting Group in β-Lactam Synthesis" Heterocycles, 1987, vol. No. 25, pp. 221-227.

Coates, C. et al. "N-Thiolated β-Lactam Antibacterials: Defining the Role of Unsaturation in the $C_4$ Side Chain" *Bioorganic & Medicinal Chemistry*, 2003, vol. No. 11, Issue No. 2, pp. 193-196.

Kellen, J. A. "Molecular Interrelationships in Multidrug Resistance (Review)," *Anticancer Research*, 1994, vol. No. 14, pp. 443-436.

Smith, D. M. et al., "Regulation of tumor cell apoptotic sensitivity during the cell cycle (Review)," *International Journal of Molecular Medicine*, 2000, vol. No. 6, pp. 1-5.

Ren, X. et al. "Synthesis of Inversely-Fused Bicyclic β-Lactams" *J. Org. Chem.*, 1995, vol. No. 60, Issue No. 16, pp. 4980-4981.

* cited by examiner

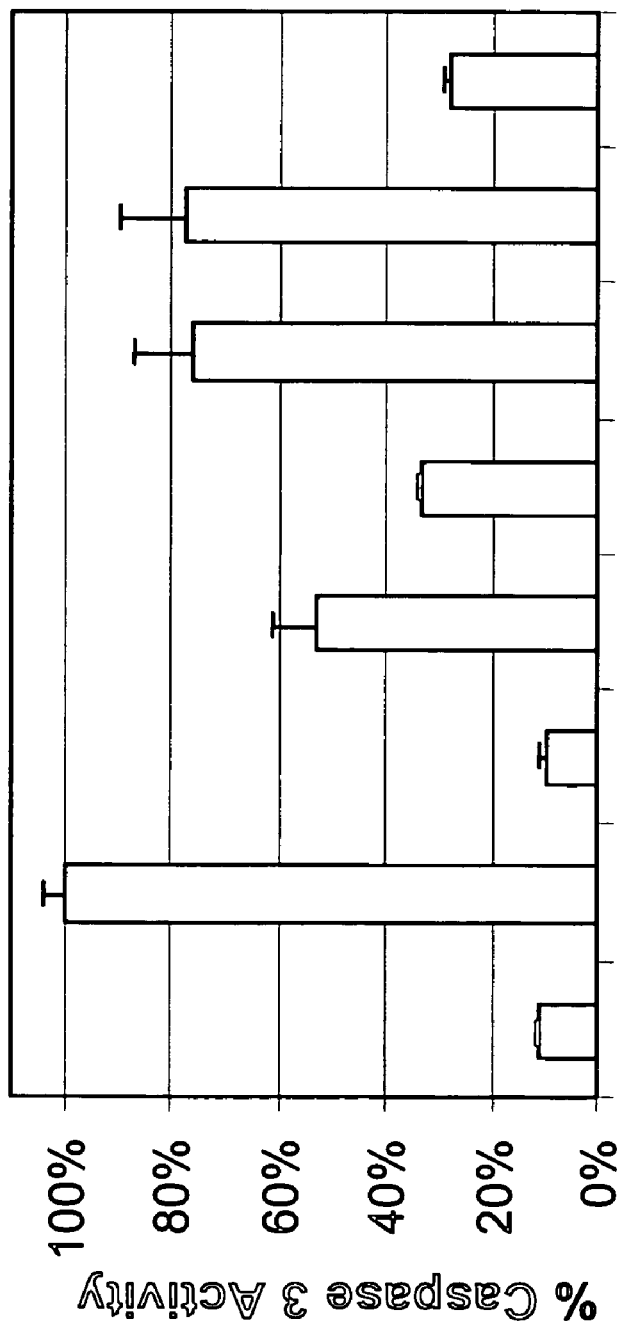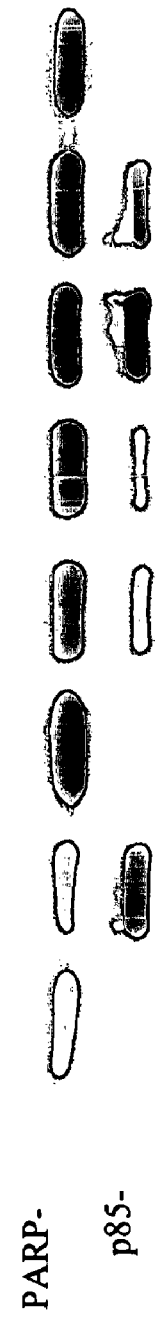
FIG. 2A
FIG. 2B

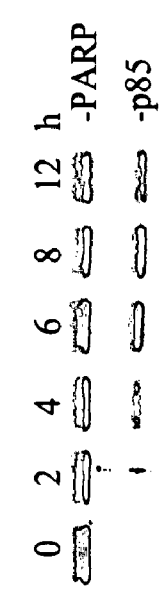
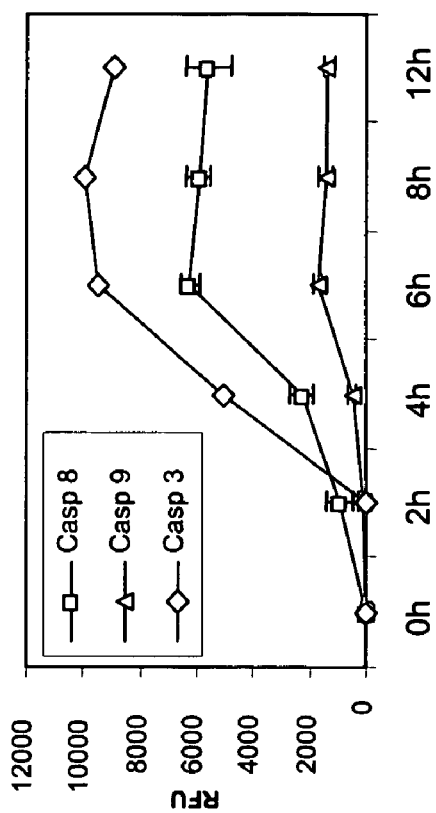
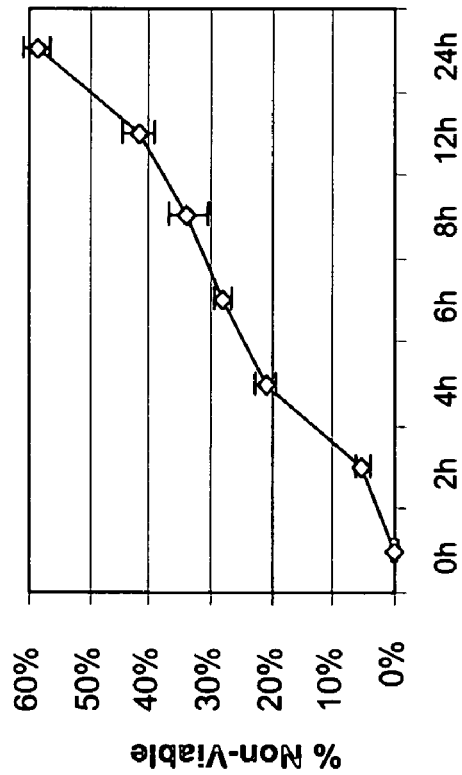
FIG. 3A
FIG. 3B
FIG. 3C
FIG. 3D

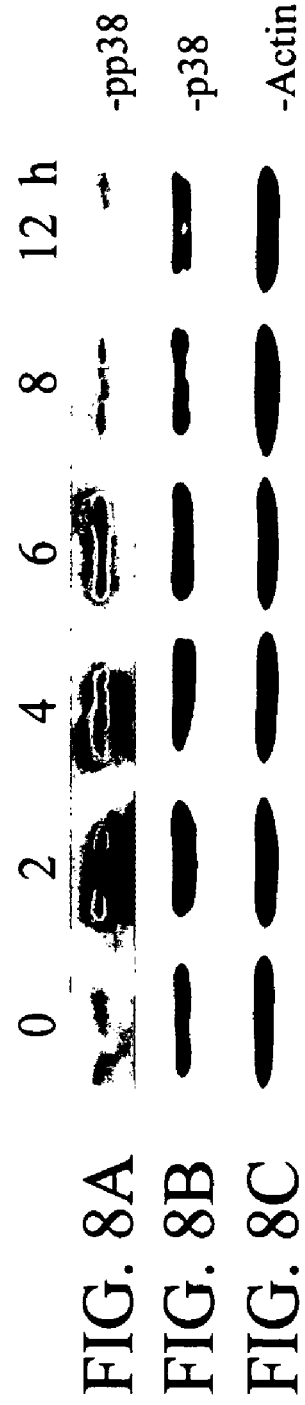
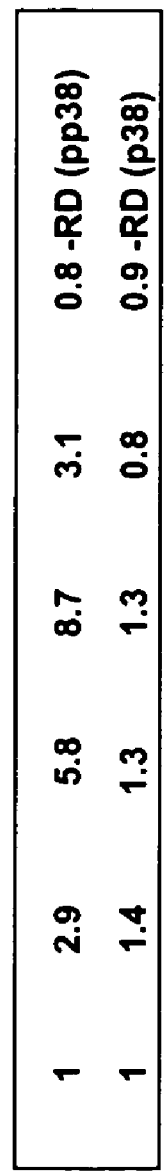
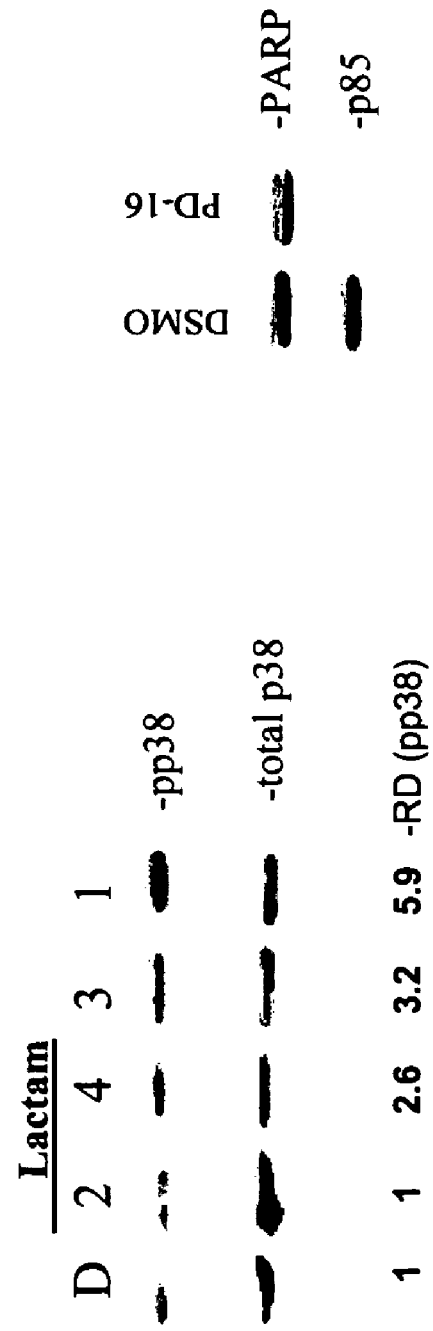
FIG. 8A
FIG. 8B
FIG. 8C
FIG. 8D
FIG. 8E

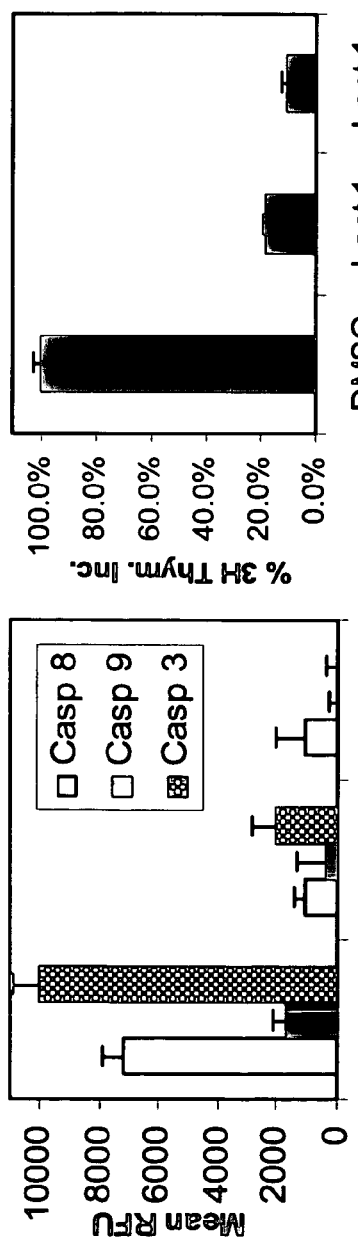
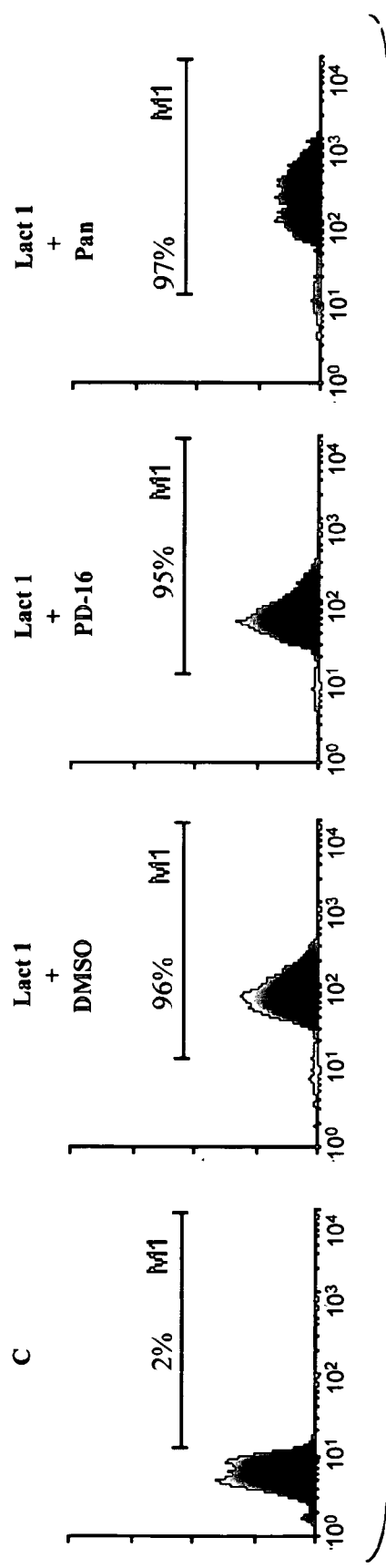
FIG. 8I
FIG. 8G
FIG. 8H
FIG. 8F

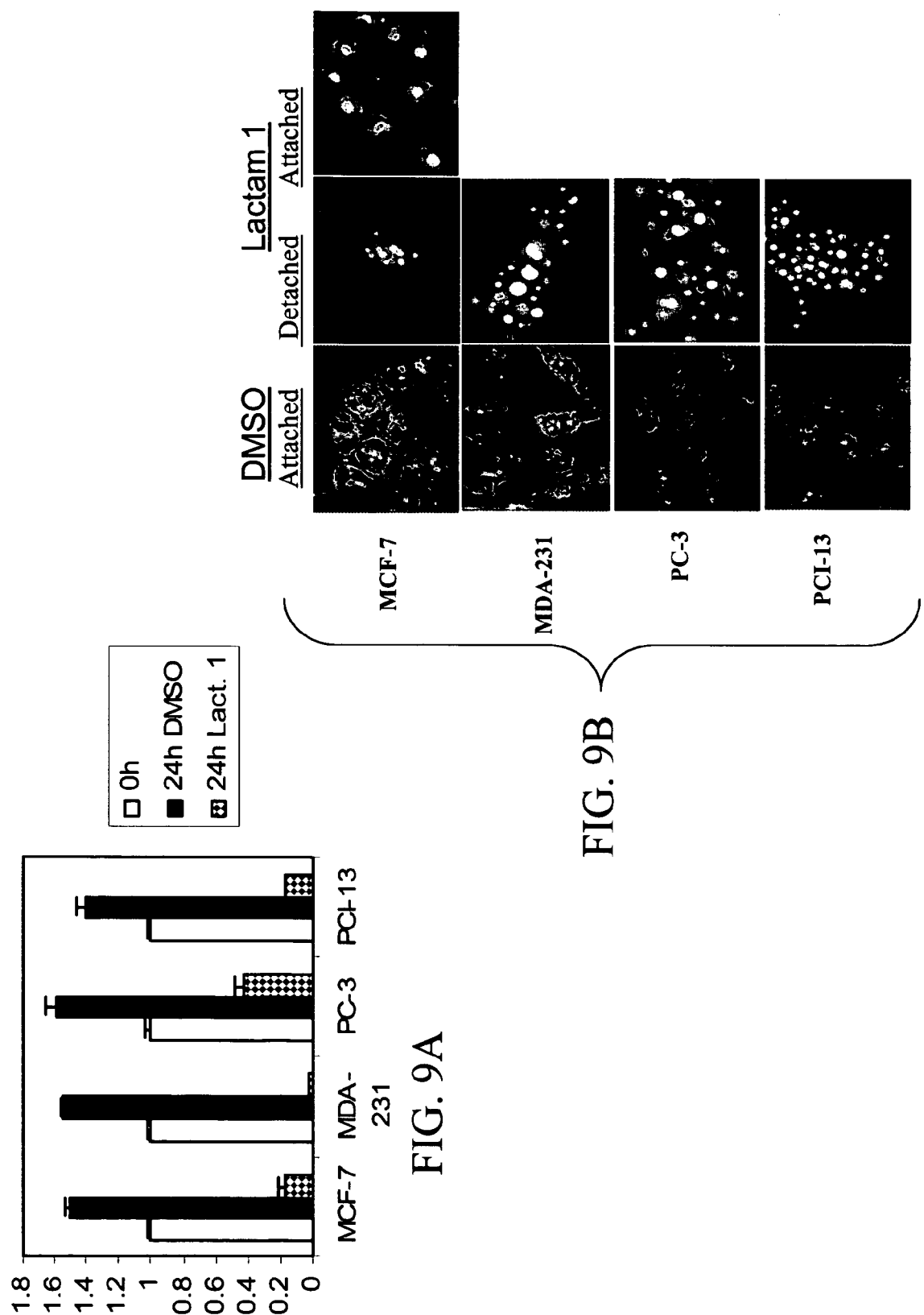

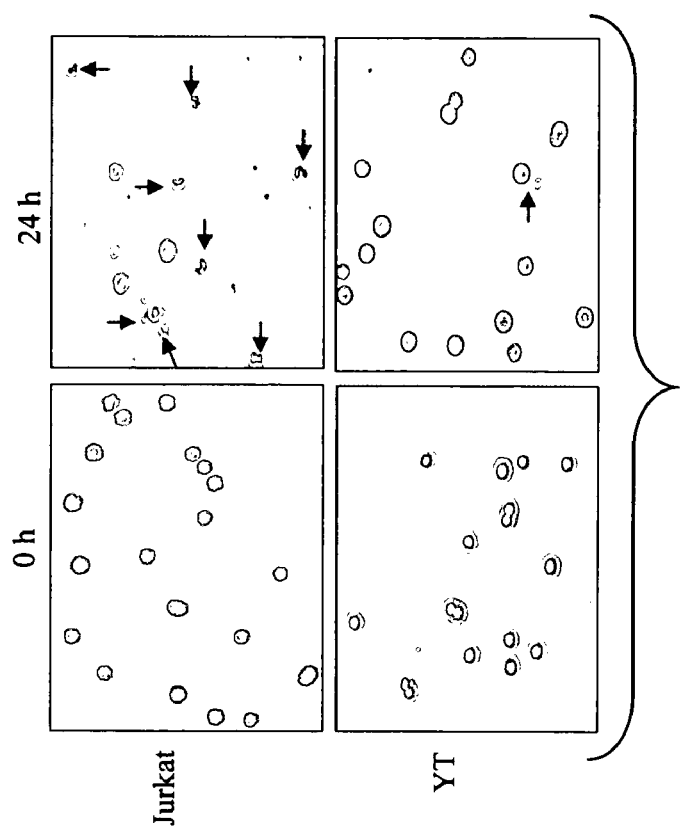
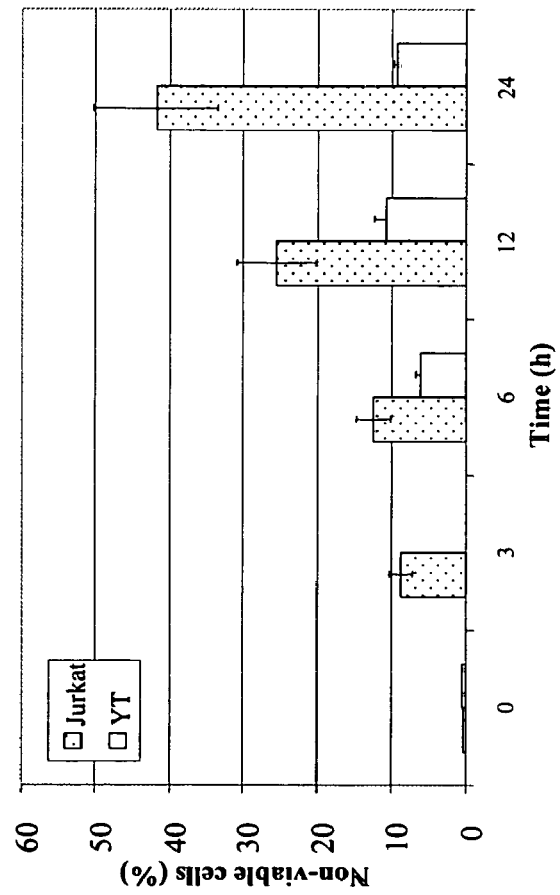
FIG. 14A
FIG. 14B
FIG. 14C
FIG. 14D

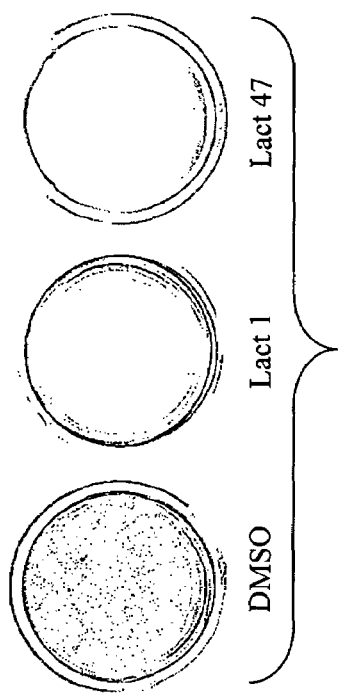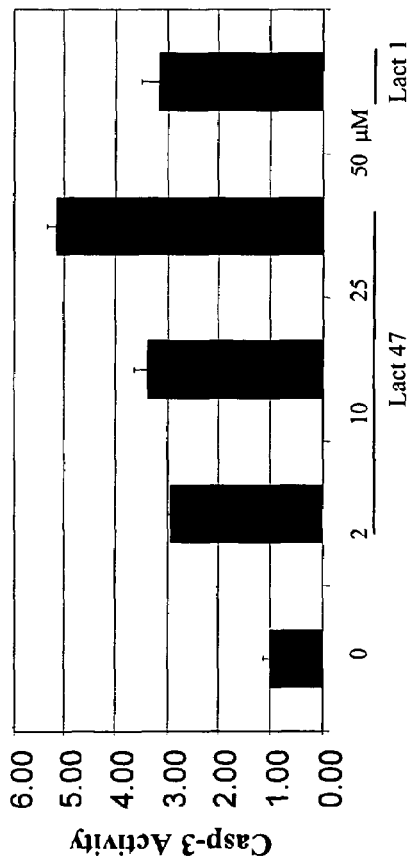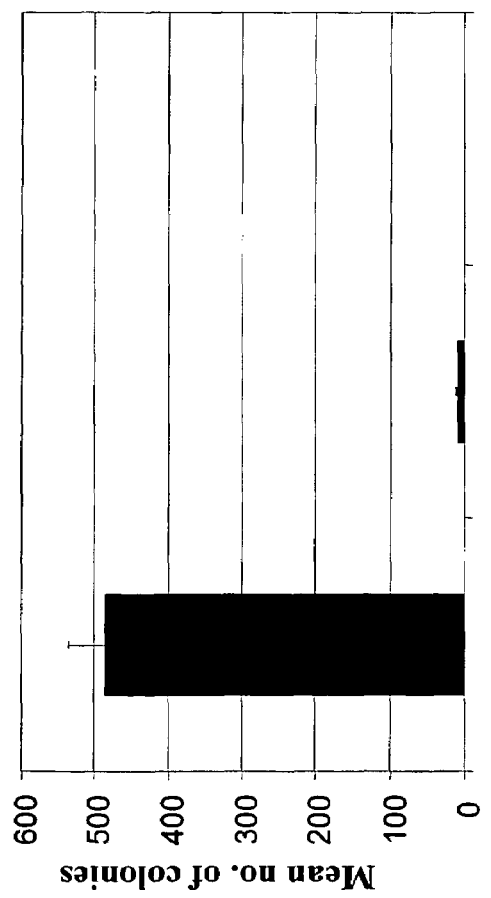
FIG. 18A
FIG. 18B
FIG. 18C

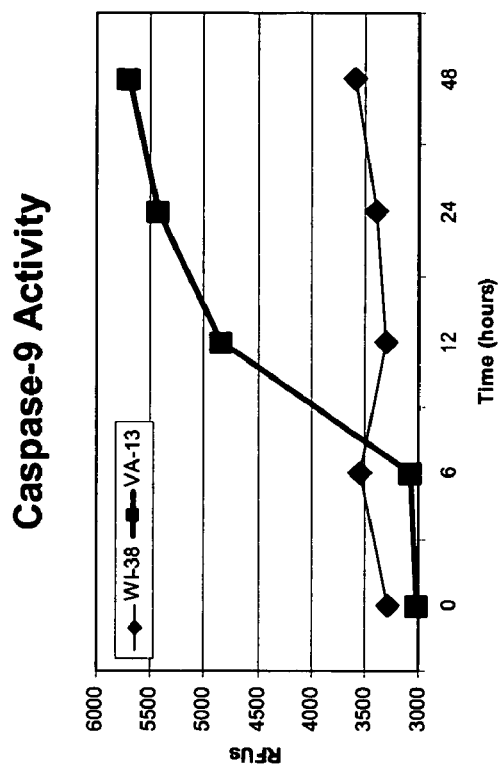
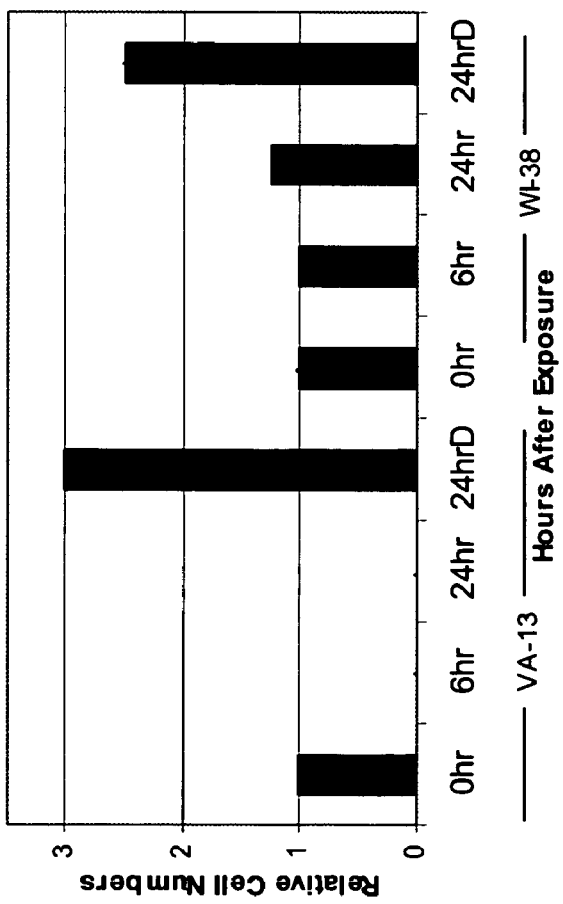
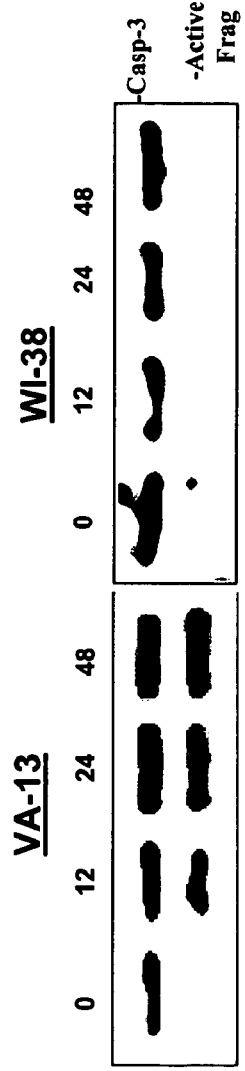
FIG. 19A
FIG. 19B
FIG. 19C

METHODS FOR PREVENTING AND TREATING CANCER USING N-THIOLATED β-LACTAM COMPOUNDS AND ANALOGS THEREOF

CROSS-REFERENCE TO RELATED APPLICATION

This application is a divisional of U.S. application Ser. No. 10/431,113, filed May 6, 2003, now U.S. Pat. No. 7,026,472 which claims the benefit of U.S. Provisional Application Ser. No. 60/377,604, filed May 6, 2002.

GOVERNMENT SUPPORT

The subject matter of this application has been supported by a research grant from the Army Research Office under grant number DAMD 17-03-1-0175. Accordingly, the government has certain rights in this invention.

FIELD OF THE INVENTION

The present invention relates to N-thiolated β-lactam compounds, and analogs and derivatives thereof, which potently induce neoplastic cell apoptosis or inhibit neoplastic cell proliferation. Specifically, the invention relates to methods of treating conditions characterized by abnormal cellular proliferation or dysregulation of the normal process of cell death in the cells or tissues of an animal using N-thiolated β-lactam compounds, and analogs and derivatives thereof.

BACKGROUND OF THE INVENTION

Apoptosis is the process by which a cell actively commits suicide through a tightly controlled program (See for example, Wyllie A H, et al., 1980, Cell death: the significance of apoptosis. *Int Rev Cytol* 68:251-306). Morphologically, apoptosis is characterized by shrinkage of the cell, dramatic reorganization of the nucleus, active membrane blebbing, and ultimately fragmentation of the cell into membrane-enclosed vesicles (apoptotic bodies) (Earnshaw W C, 1995, Nuclear changes in apoptosis. *Curr Opin Cell Biol* 7:337-43). Apoptosis occurs in two physiological stages: commitment and execution.

Recent experiments have demonstrated that mitochondria play an essential role in apoptotic commitment (Green D R et al., 1998, Mitochondria and apoptosis. *Science* 281:1309-12). Upon apoptotic stimulation, several important events occur at the mitochondria, including the release of cytochrome C. Release of cytochrome C from the mitochondria can be inhibited by the expression of anti-apoptotic Bcl-2 family members (such as Bcl-2 and Bcl-XL) and induced by the expression of pro-apoptotic Bcl-2 proteins (such as Bax and BID). During receptor-mediated apoptosis, BID is cleaved at its N-terminus by caspase-8. The carboxyl-terminal fragment of BID (MW 15 kDa) is then inserted into the membrane of the mitochondria, triggering release of mitochondrial cytochrome C (Li H, et al., 1998, Cleavage of BID by caspase-8 mediates the mitochondrial damage in the Fas pathway of apoptosis. *Cell* 94:491-501).

Releasing cytochrome C from mitochondria commits the cell to die by either apoptosis or necrosis. The cytochrome C-induced apoptotic process involves Apaf-1-mediated caspase activation. This cytosolic cytochrome C interacts with Apaf-1, which induces its association with procaspase-9, thereby triggering processing and consequent activation of caspase-9. The activated caspase-9 in turn cleaves downstream effector caspases (such as caspase-3), initiating apoptotic execution (Green et al., supra; Martin, et al., 1995, *Cell.* 82:349-52; Thomberry et al., 1998, *Science.* 281:1312-6). It is believed that activating effector caspases leads to apoptosis through the proteolytic cleavage of important cellular proteins, such as poly(ADP-ribose) polymerase (PARP) (Lazebnik et al., 1994, *Nature.* 371:346-7) and the retinoblastoma protein (RB) (An et al., 1996, *Cancer Res.* 56:438-42; Janicke et al., 1996, *Embo J.* 15:6969-78; Fattman, et al., 2001, *Oncogene.* 20:2918-26).

Activating the cellular apoptotic program is a current strategy for treating human cancer. In fact, radiation and standard chemotherapeutic drugs have been demonstrated to kill some tumor cells by inducing apoptosis (Fisher, 1994, *Cell.* 78:539-42).

Unfortunately, the majority of human cancers at present are resistant to present therapies (Harrison, 1995, *J Pathol.* 175:7-12; Desoize, 1994, *Anticancer Res.* 14:2291-2294; Kellen, 1994, *Anticancer Res.* 14:433-435). It is therefore essential to identify novel anti-cancer compounds that induce apoptosis. Along this line, synthetic small compounds have great potential to be developed into anticancer drugs because they can be easily synthesized and structurally manipulated for selective development.

For more than 60 years, N-thiolated β-lactam antibiotics have played an essential role in treating bacterial infections (Morin et al., Chemistry and Biology of beta-lactam Antibiotics, Vol. 1-3. New York: Academic Press, 1982; Kukacs et al., Recent Progress in the Chemical Synthesis of Antibiotics. Berlin, Springer-Verlag, 1990). Recently a new class of N-thiolated β-lactam is found to inhibit bacterial growth in *Staphylococcus aureus* (Turos et al., 2000, *Tetrahedron* 56:5571-5578; Ren, et al., 1998, *J. Org. Chem.* 63:8898-8917). These compounds thus have proven clinical acceptability. To date, N-thiolated β-lactam compounds have not found use as anticancer drugs. Accordingly, N-thiolated β-lactam compounds that rapidly induce DNA damage, inhibit DNA replication, and induce an apoptotic effect, including inducing a death program of a neoplastic cell in a time and concentration dependent manner are desired.

BRIEF SUMMARY OF THE INVENTION

The invention concerns a method for inducing tumor cell death or inhibiting tumor cell proliferation, comprising contacting the cell with an effective amount of a N-thiolated β-lactam compound, or a pharmaceutically acceptable salt, ester or amide thereof. According to a preferred embodiment, the inventive method uses N-thiolated β-lactam A-H as hereinafter defined. In a particularly preferred embodiment, N-thiolated β-lactam A is used.

The method of the present invention is preferably used to treat tumor cells present in an animal, preferably a mammal, such as a human patient. The tumor cells can be those of a solid tumor or a blood borne tumor. Suitable cancers that can be treated with the present invention include, but are not limited to lung, breast, colon, prostate, melanoma, pancreas, stomach, liver, brain, kidney, uterus, cervix, ovaries, urinary tract, gastrointestinal, head-and-neck cancer or leukemia. N-thiolated β-lactam compounds of the present invention can be administered to the animal orally, intramuscularly, and/or transdermally.

The present invention also relates to pharmaceutical compositions comprising N-thiolated β-lactam compounds of the invention. In a preferred embodiment, an N-thiolated β-lactam compound of the invention has the structure shown in formula (I). In one embodiment, the N-thiolated β-lactam has the structure of the compound corresponding to lactam 1 as defined in Table 1.

In yet another embodiment, the present invention relates to a method for inducing, in a tumor cell, DNA damage, DNA replication inhibition, p38 MAP kinase activation, or caspase cascade activation, or cytochrome C release from mitochondria into the cytoplasm, comprising contacting the tumor cell with an effective amount of a N-thiolated β-lactam compound.

In a further embodiment, the present invention relates to a method for screening an N-thiolated β-lactam compound or an analog thereof for its ability to induce tumor cell death or to inhibit tumor cell proliferation, the method comprising the steps of a) contacting a culture of tumor cells with the compound; b) preparing a lysate of the treated cells; and c) measuring apoptosis-specific caspase-3 activity or PARP cleavage; wherein an increase in either caspase-3 activity or PARP cleavage as compared to untreated tumor cells indicates that the compound or analog thereof is capable of inducing cancer cell death or inhibiting cancer cell proliferation. In a preferred embodiment, human Jurkat T cells can be used for screening.

The purpose and advantages of the present invention will be set forth in and apparent from the description that follows, as well as will be learned by practice of the invention. Additional advantages of the invention will be realized and attained by the methods and compositions particularly pointed out in the written description and claims hereof, as well as from the appended drawings.

Both the foregoing general description and the following detailed description are exemplary and are intended to provide further explanation of the invention claimed. Those skilled in the art will appreciate that the conception upon which this disclosure is based can readily be utilized to prepare other N-thiolated β-lactam compounds and methods of using such compounds for carrying out the methods of the present invention. It is important, therefore, that the claims be regarded as including such equivalent compounds and methods of using such compounds insofar as they do not depart from the spirit and scope of the present invention.

The accompanying drawings, which are incorporated in and constitute part of this specification, are included to illustrate and provide a further understanding of the compositions and methods of the invention. Together with the description, the drawing serves to explain the principles of the invention.

BRIEF DESCRIPTION OF THE FIGURES

FIGS. 2A-D show the apoptosis-inducing potencies of different N-thiolated β-lactam analogs. Jurkat T cells are treated with either 50 μM of each individual compound or the vehicle DMSO (indicated by D) for 8 h, followed by preparation of cellular extracts. FIGS. 2A and 2C show cell-free caspase-3 activity assay. Standard deviations are calculated from three separate and independent experiments and are indicated by error bars. FIGS. 2B and 2D show Western blot assay using a specific polyclonal PARP antibody. The intact PARP (MW 116 kDa) and a PARP cleavage fragment (p85) are shown. Similar results are obtained in three or more experiments.

FIGS. 3A-D show a kinetic characterization of lactam 1-induced apoptosis. Jurkat T cells are treated with 50 μM lactam 1 for the indicated hours, followed by performance of various assays as follows. FIGS. 3A and 3D show Western blot assay using specific antibodies to PARP, BID or caspase-9. The intact caspase-9 (MW 45 kDa) and its cleavage (active) fragment (35 kDa) as well as a BID cleavage fragment (15 kDa) are shown. The experiments are conducted at least three times with similar results. FIG. 3B shows trypan blue incorporation assay. The numbers given are percentages of non-viable cells to total cells. Standard deviations are shown with error bars from a mean of at least 3 different experiments. FIG. 3C shows cell-free caspase-8, caspase-9 and caspase-3 assay. Standard deviations are shown from 3 different experiments.

FIG. 4 shows that lactam 1 induces cytochrome C release from mitochondria. Cytosol and mitochondria fractions are prepared from Jurkat T cells treated with 50 μM lactam 1 for indicated hours, followed by Western blot assay using a specific antibody to cytochrome C (MW 17 kDa; A), the cytochrome oxidase subunit H (COX, MW 26 kDa; B) and ~-actin (MW 43 kDa; C). The unchanged levels of mitochondrial COX and cytosolic ~3-actin protein serve as controls for equal loading and fractionation purity.

FIG. 5D demonstrates that caspase inhibitors block apoptosis induced by lactam 1. Jurkat T cells are pretreated with either a specific inhibitor to caspase-8, caspase-9 or caspase-3 (at 25 μM), or a general caspase inhibitor (pan, at 25 μM), or DMSO, followed by a co-treatment with 50 μM lactam 1 for 8 hours. After that, PARP cleavage is determined in a Western blot assay.

FIG. 6A shows Jurkat T cells are treated with 50 μM lactam 1 for the indicated hours, followed by flow cytometry analysis. The cell cycle distribution is measured as the percentage of cells that contain $G_1$, S, $G_2$ and M DNA (cells in $G_1$, S, G2 and M=100%). The apoptotic population is measured as the percentage of total cell populations with <$G_1$ DNA content. FIG. 6B shows Jurkat T cells are treated with either DMSO (D) or 50 μM lactam for (1, 2, 3, or 4), for five hours, followed by assaying the cell cycle distribution and Sub $G_1$ population.

FIGS. 7A and 7B: $^3$H-thymidine incorporation assay. Jurkat T cells are either untreated (as a control, indicated by C or 0 μM), or pretreated with 50 μM lactam 1 for the indicated hours (FIG. 7A), or pretreated with indicated concentrations of lactam 1 for 2 hours (FIG. 7B). $^3$H-thymidine is then added, followed by a 2 hour incubation. The amount of $^3$H-thymidine incorporated is then analyzed by scintillation counting (see MATERIALS AND METHODS section herein). Standard deviations are shown with error bars from a mean of at least 3 different experiments. FIGS. 7C-7E: TUNEL assay. Jurkat cells are treated with 50 μM lactam 1 for four hours (FIG. 7D) each indicated time point (FIG. 7C), or with 50 μM of the indicated drug for four hours (FIG. 7E), followed by analysis of DNA strand breaks by flow cytometry (FIGS. 7C and 7E) or a fluorescence microscopy (FIG. 7D). The M1 region represents the TUNEL-positive (DNA strand breaks) cells. Similar results are observed in 3 independent experiments.

FIGS. 8A-I show the involvement of p38 MAP kinase in lactam 1-induced apoptosis. (FIGS. 8A-D) Jurkat T cells are treated with 50 μM lactam 1 for the indicated hours (FIG. 8D), followed by Western blot assay using specific antibodies to phosphorylated p38 (pp38, total p38, or actin. RD (relative density) values are normalized ratios of the intensities of pp38 or p38 band to the corresponding actin band. The experiments are done three times with similar results. (FIGS. 8E and 8F) Jurkat T cells are pre-treated for 1 hour with either the specific p38 MAP kinase inhibitor PD-169316 (PD-16; at 30 μM), the pan caspase inhibitor (at 25 μM), or the vehicle DMSO, followed by a co-treatment with 50 μM lactam 1 for 8 h. After that, PARP cleavage is determined in Western blotting (FIG. 8E) and caspase-8, caspase-9 and caspase-3 activities are measured in cell-free assay (FIG. 8F; and see FIG. 3). (FIG. 8G) Jurkat T cells are pretreated with 50 μM lactam 1, 50 μM lactam 1 plus 30 μM PD16, or DMSO for 2 hours, followed by addition of $^3$H-thymidine. After an additional 2 hours of incubation, the amount of $^3$H-thymidine incorporated is then analyzed by scintillation counting (see FIG. 7). (FIGS. 8H-I) Jurkat T cells are treated for four hours with either DMSO or lactam 1 (at 50 μM), in the absence (with DMSO) or presence of PD 169316 (PD-16; at 30 μM) or Boc-D-FMK (50 μM), followed by measurement of TUNEL positivity and p38 phosphorylation as described in FIG. 7C and FIGS. 8A-8C, respectively.

FIGS. 9A-B show that lactam 1 inhibits proliferation and induces apoptosis in four solid tumor cell lines. (FIG. 9A) MTT assay. Human breast (MCF-7, MDA-MB-231), prostate (PC-3), and head-and-neck (PCI-13) cancer cell lines are grown in equal cell numbers in a 24-well plate. At ~50% confluency (0 hours), three wells of each cell line are treated with either 50 μM lactam 1 or DMSO for 24 hours. After that, cells are subjected to MTT assay. Standard deviations are given as described in FIG. 3. (FIG. 9B) Nuclear staining assay. MCF-7, MDA-MB231, PC-3 and PCI-13 cells are treated with 50 μM lactam 1 or DMSO for 24 (MCF-7) or 48 hours (other three lines), followed by collecting both detached and attached cell populations. After lactam 1 treatment, ~50% of these cancer cell lines became detached, whereas <5% became detached after treating with DMSO. Both detached and attached cell populations are used for nuclear staining assay with DNA staining die Hoechst 33342. Each sample is then analyzed by fluorescence microscopy for nuclear morphology. Similar results are obtained in 6 independent experiments.

(FIG. 13A) Structures of the N-thiolated β-lactam compounds studied. Numerical designations were given to each compound. (FIG. 13B) Jurkat T cells were treated with the solvent (DMSO) or 50 μM of each indicated analog for 24 h, followed by trypan blue dye exclusion assay. The numbers given are percentages of non-viable cells to total cells. Standard deviations are shown with error bars from a mean of at least three different experiments.

FIGS. 14A-D show selective induction of apoptosis by lactam 1 in leukemic Jurkat T over immortalized/non-transformed NK cells. Jurkat T and NK (YT) cells were treated with 10, 25 and 50 μM of lactam 1 for 24 h (FIG. 14A) or with 30 μM of lactam 1 for indicated hours (FIGS. 14B-D). (FIGS. 14A and 14B) Measurement of PARP cleavage in Western blot assay. The intact PARP (116 kDa) and a PARP cleavage fragment (p85) are shown. (FIG. 14C) Trypan blue dye exclusion assay. The numbers given are percentages of non-viable cells to total cells. Standard deviations are shown with error bars from a mean of at least three different experiments. (FIG. 14D) Morphological changes of Jurkat T and YT cells after treatment. Photographs under a phase-contrast microscope (100×).

(FIG. 17A) Measurement of sub-$G_1$ DNA content by flow cytometry analysis. The percentage of sub-$G_1$ cell population represents the cell populations with DNA fragmentation. (FIG. 17B) Measurement of DNA strand breaks by TUNEL assay. The numbers indicate the percentage of TUNEL-positive population. Results of representative of three independent experiments are shown.

FIGS. 18A-C show effects of β-lactams on caspase activation and colony formation. (FIG. 18A) Prostate cancer LNCaP cells were treated for 48 h with 2, 10, and 25 μM of lactam 12 versus 50 μM of lactam 1. Cell-free caspase-3 activity was then determined by incubating whole cell extracts with caspase-3 substrate and measuring free AMCs. (FIGS. 18B and 18C) LNCaP cells were plated in soft agar with the solvent DMSO or 50 μM of the indicated β-lactams. Cells were then cultured for 21 days without addition of new drug. The plates were scanned and a representative well from each treatment was selected for presentation (FIG. 18B). Colonies were quantified with an automated counter and presented as mean values from triplicate independent experiments. Error bars denote standard deviations (FIG. 18C).

FIGS. 19A-D show lactam 1 selectively inhibits proliferation and induce apoptosis in SV40-transformed human fibroblasts, but not the normal, parental human fibroblasts. The normal (WI-38) and SV40-transformed (VA-13) human fibroblasts, grown in either 96-well plates (FIG. 19A, 0 h) or 60-mm dishes (FIGS. 19B-D, 0 h), are treated with either 50 μM lactam 1 or DMSO (or D) for up to 48 hours. (FIG. 19A) MTT assay. (FIG. 19B) Cell-free caspase-9 activity assay. A protein extract (20 μg) is incubated with 20 μM Ac-LEHD-AFC (the specific caspase-9 substrate) in a 96-well plate at 37° C. for 2 h. After incubation, the liberated florescent AFC groups are measured by Wallac Victor 1420 Multilabel counter with 405/535 nM filters. FIG. 19C shows processing and activation of caspase-3 detected in Western blot assay. Both intact and active forms of caspase-3 are indicated. FIG.

Figure 1:
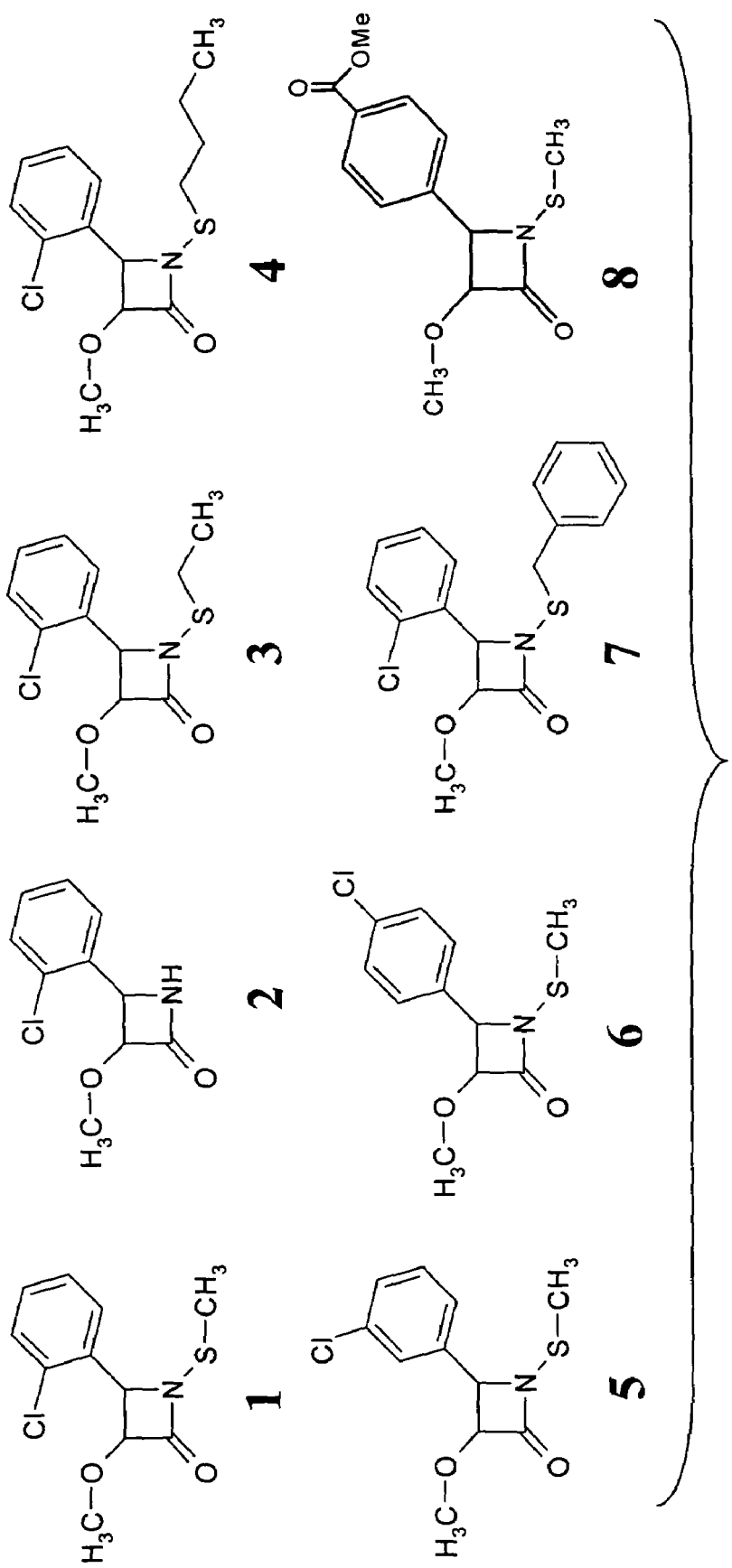
FIG. 1 shows structures of eight N-thiolated β-lactam compounds of the present invention.

19D shows nuclear staining assay. Treatment with lactam 1 or DMSO for 48 hours induced ~60% and <5%, respectively, of VA-13 cells detached. When WI-38 cells are treated with either lactam 1 or DMSO for 38 hours, no detachment is observed. Both detached and attached populations of Va-13 or WI-38 cells are collected, and used for nuclear staining assay with DNA staining dye Hoechst 33342.

DETAILED DISCLOSURE OF THE INVENTION

Reference will now be made in detail to the present preferred embodiments of the invention, examples of which are illustrated in the accompanying figures. The methods and corresponding compositions of the invention will be described in conjunction below.

An important property of candidate anticancer drugs is the ability to induce tumor cell apoptosis (Pfundt et al., 2001, *J. Pathol.* 193:248-55). The present invention concerns N-thiolated β-lactam compounds that induce apoptosis and inhibit cell cycle progression in several human cancer cell lines.

Definitions

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARMACEUTICAL SCIENCES, 15th Ed., Mack Publ. Co., Easton, Pa. (1975).

A "hyperproliferative disorder" is any condition in which a localized population of proliferating cells in an animal is not governed by the usual limitation of normal growth. Examples of hyperproliferative disorders include tumors, neoplasms, lymphomas and the like.

"Pharmaceutically acceptable salt, ester or amide" as used herein, relates to a chemical modification of a compound of the present invention wherein the chemical modification takes place either at a functional group of the compound or on the aromatic ring. Pharmaceutically acceptable salt, ester or amide, include any pharmaceutically acceptable salt, amide, ester, or other derivative. The derivative of a compound of the present invention, upon administration to a recipient, is capable of providing, directly or indirectly, a compound of this invention or an active metabolite or residue thereof. Particularly favored derivatives increase the bioavailability of the compounds of this invention when such compounds are administered to a mammal (e.g., by allowing an orally administered compound to be more readily absorbed into the blood) or enhance delivery of the parent compound to a biological compartment (e.g., the brain or lymphatic system).

As known to those of skill in the art, "salts" of the compounds of the present invention can be derived from inorganic or organic acids and bases. Examples of acids, for purposes of illustration and not limitation, include hydrochloric, hydrobromic, sulfuric, nitric, perchloric, fumaric, maleic, phosphoric, glycolic, lactic, salicylic, succinic, p-toluenesulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be used to prepare salts that are useful intermediates in obtaining the compounds of the invention and their pharmaceutically acceptable acid addition salts.

Examples of bases, for purposes of illustration and not limitation, include alkali metal (e.g sodium) hydroxides, alkaline earth metal (e.g., magnesium) hydroxides, and ammonia. Examples of salts, for purposes of illustration and not limitation, include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate and undecanoate. For therapeutic use, salts of the compounds of the present invention will be pharmaceutically acceptable. However, salts of acids and bases that are non-pharmaceutically acceptable can also find use, for example, in the preparation or purification of a pharmaceutically acceptable compound.

β-lactam Compounds

The subject invention concerns N-thiolated β-lactam compounds and uses thereof. Compounds of the invention have apoptotic and/or anti-proliferative properties against tumor cells.

β-lactam compounds encompassed within the scope of the present invention can have the general formula A:

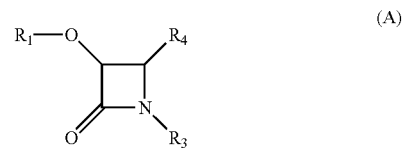

wherein $R_1$ is a hydrocarbon group having 1-8 carbon atoms and includes alkyl, alkenyl, and alkynyl groups;

$R_3$ is an organothio group; and $R_4$ is an alkyl, alkenyl, alkynyl, aryl, heteroaryl, cycloalkyl, heterocycloalkyl, cycloalkenyl, or heterocycloalkenyl, any of which can be optionally substituted with $R_2$, wherein $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I;

or a pharmaceutically acceptable salt, ester or amide thereof.

In one embodiment, β-lactam compounds of the present invention can have the following formula I:

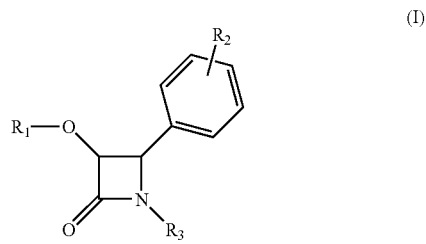

in which $R_1$ is a hydrocarbon group having 1-8 carbon atoms and includes alkyl, alkenyl, and alkynyl groups; $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, —CHO, —COOH, amido, amino, carboxylic ester group, or COX, wherein X is Cl, F, Br, or I; and $R_3$ is an organothio group; or a pharmaceutically acceptable salt, ester or amide thereof.

Figure 11A:
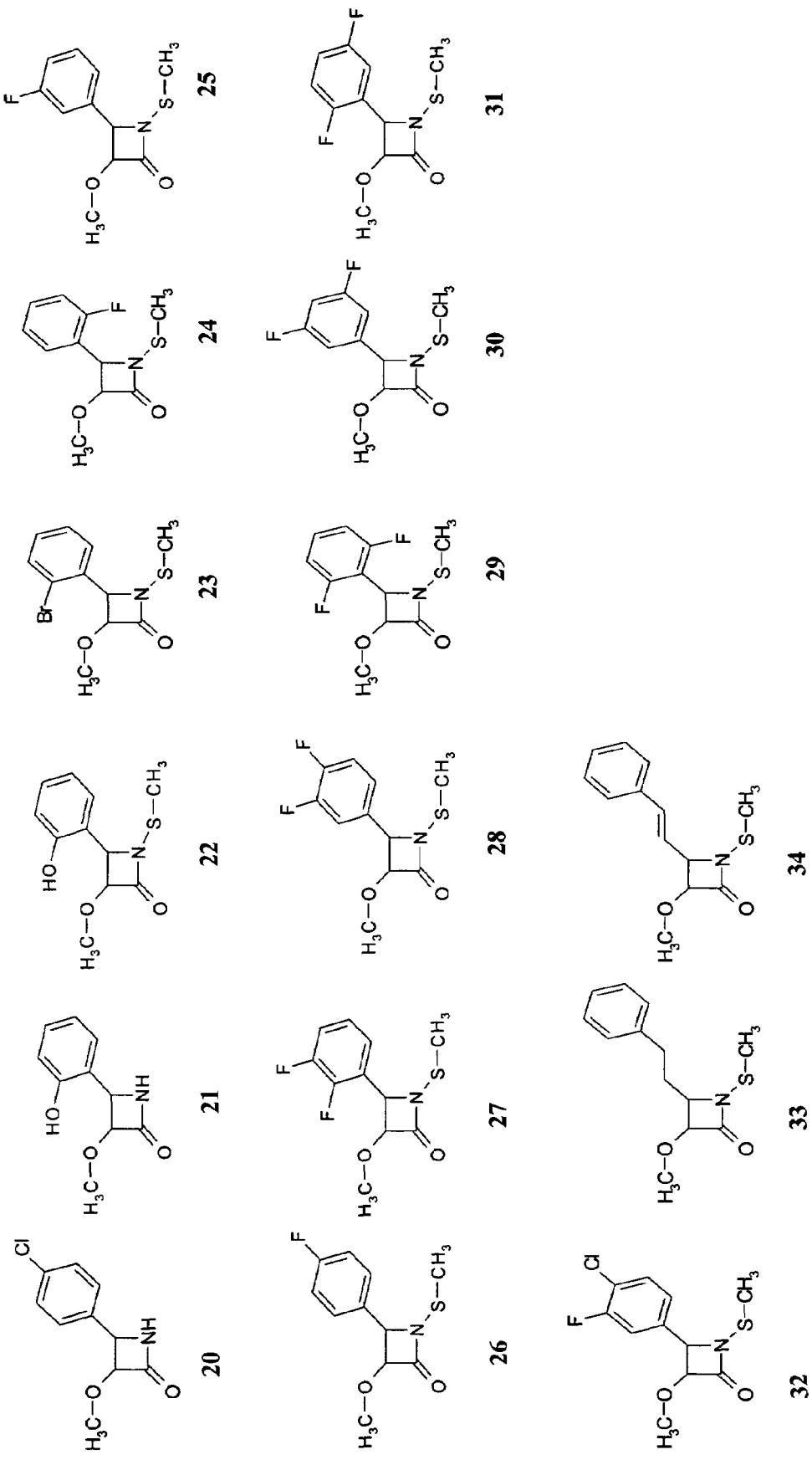
FIGS. 11A-B show structures of N-thiolated β-lactam compounds of the present invention.
Figure 11B:
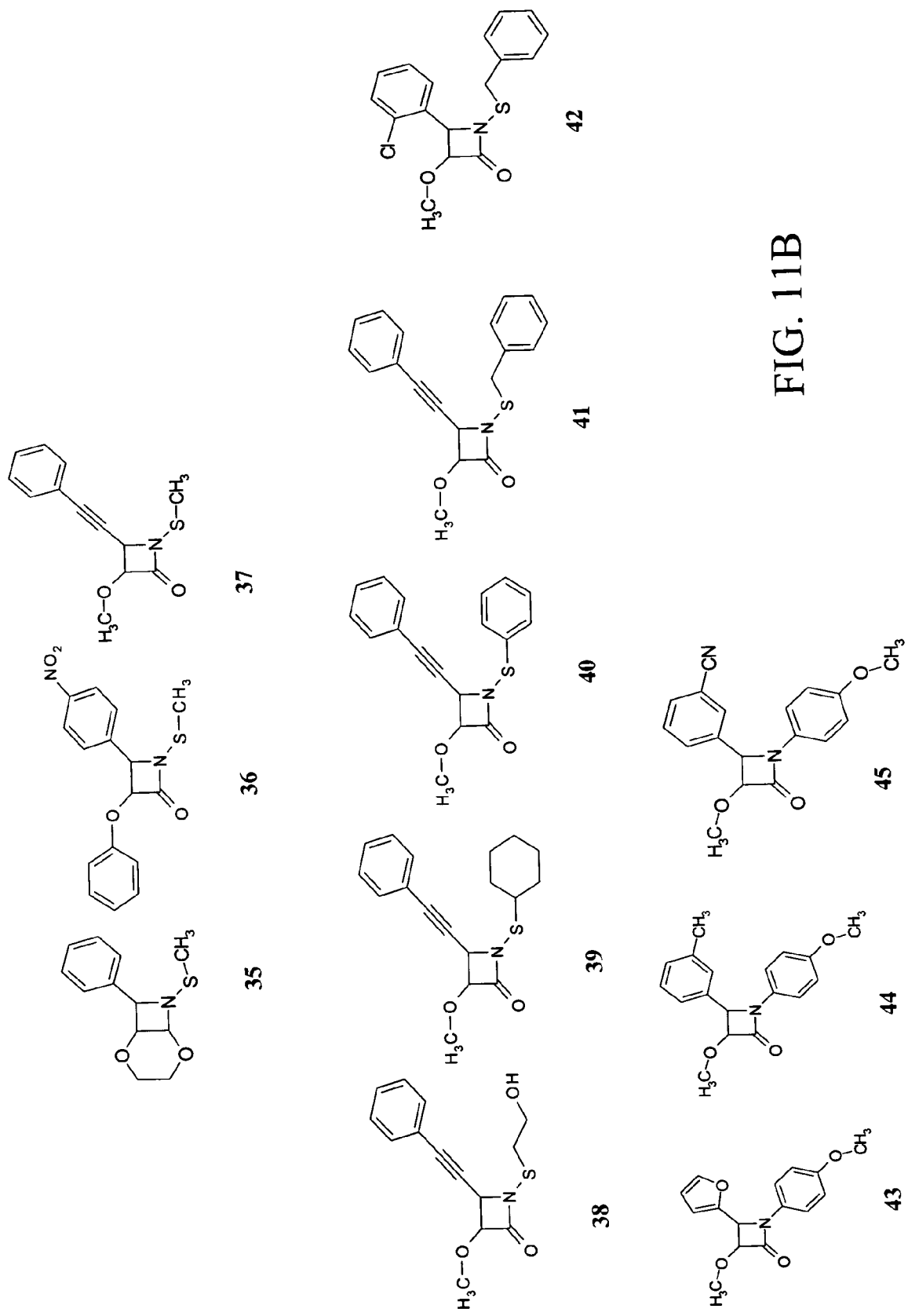
Figure 12:
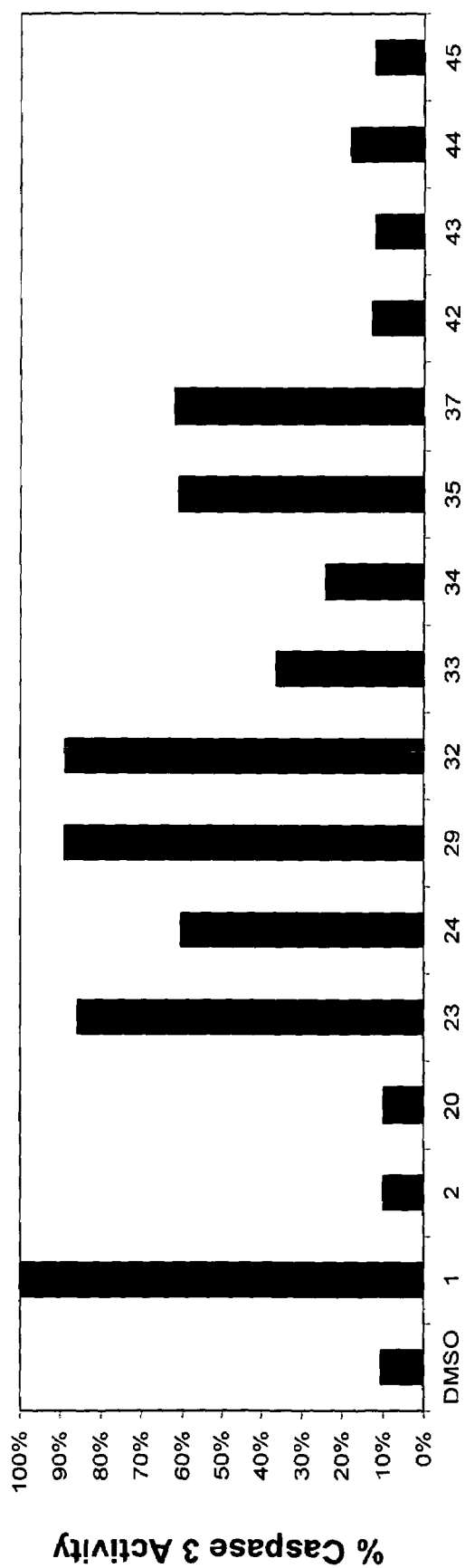
FIG. 12 shows cell-free caspase-3 activity assay. Jurkat T cells are treated with either each indicated compound at 50 μM or the vehicle DMSO for 8 h, followed by preparation of cellular extracts and performance of cell-free caspase-3 activity assay.

In exemplified embodiments, the β-lactam compounds of formula I have structures shown in FIGS. 1, 11, and 13A, and Table 1 below.

TABLE 1

N-thiolated β-lactam Compounds of formula I of the Invention

| Compound # | $R_1$ | $R_2$ (position on the phenyl ring) | | | | | $R_3$ |
|---|---|---|---|---|---|---|---|
| | | 2 | 3 | 4 | 5 | 6 | |
| lactam 1 | —$CH_3$ | —Cl | | | | | —S—$CH_3$ |
| lactam 2 | —$CH_3$ | —Cl | | | | | —H |
| lactam 3 | —$CH_3$ | —Cl | | | | | —S—$CH_2CH_3$ |
| lactam 4 | —$CH_3$ | —Cl | | | | | —S—$(CH_2)_3CH_3$ |
| lactam 5 | —$CH_3$ | | —Cl | | | | —S—$CH_3$ |
| lactam 6 | —$CH_3$ | | | —Cl | | | —S—$CH_3$ |
| lactam 7 | —$CH_3$ | —Cl | | | | | —S—$CH_2$—Ph |
| lactam 8 | —$CH_3$ | | | —$CO_2CH_3$ | | | —S—$CH_3$ |
| lactam 9 | —$CH_3$ | —Cl | | | | | —S—$CH_2$—$CH_3$ |
| lactam 10 | —$CH_3$ | —Cl | | | | | —S—$(CH_2)_3CH_3$ |
| lactam 11 | —$CH_3$ | —Cl | | | | | —S—$(CH_2)_7CH_3$ |
| lactam 12 | —$CH_3$ | —Cl | | | | | $SCH_2CO_2CH_3$ |
| lactam 13 | —$COCH_3$ | —Br | | | | | —S—$CH_3$ |
| lactam 14 | —$COCH_3$ | —F | | | | | —S—$CH_3$ |
| lactam 15 | —$CH_3$ | | —Br | | | | —S—$CH_3$ |
| lactam 16 | —$CH_3$ | | | —Br | | | —S—$CH_3$ |
| lactam 17 | —$CH_3$ | —$CO_2Me$ | | | | | —S—$CH_3$ |
| lactam 18 | —$CH_3$ | | | —$CO_2CH_2CH_3$ | | | —S—$CH_3$ |
| lactam 19 | —$CH_3$ | | | —$CO_2(CH_2)_4CH_3$ | | | —S—$CH_3$ |
| lactam 20 | —$CH_3$ | | | —Cl | | | H |
| lactam 21 | —$CH_3$ | OH | | | | | H |
| lactam 22 | —$CH_3$ | OH | | | | | —S—$CH_3$ |
| lactam 23 | —$CH_3$ | —Br | | | | | —S—$CH_3$ |
| lactam 24 | —$CH_3$ | —F | | | | | —S—$CH_3$ |
| lactam 25 | —$CH_3$ | | —F | | | | —S—$CH_3$ |
| lactam 26 | —$CH_3$ | | | —F | | | —S—$CH_3$ |
| lactam 27 | —$CH_3$ | —F | —F | | | | —S—$CH_3$ |
| lactam 28 | —$CH_3$ | | —F | —F | | | —S—$CH_3$ |
| lactam 29 | —$CH_3$ | —F | | | | —F | —S—$CH_3$ |
| lactam 30 | —$CH_3$ | | —F | | —F | | —S—$CH_3$ |
| lactam 31 | —$CH_3$ | —F | | | —F | | —S—$CH_3$ |
| lactam 32 | —$CH_3$ | | —F | —Cl | | | —S—$CH_3$ |
| lactam 36 | —Ph | | | —$NO_2$ | | | —S—$CH_3$ |
| lactam 42 | —$CH_3$ | —Cl | | | | | —S—$CH_2$—Ph |
| lactam 44 | —$CH_3$ | | —$CH_3$ | | | | —$PhOCH_3$ |
| lactam 45 | —$CH_3$ | | —CN | | | | —$PhOCH_3$ |
| lactam 46 | —$CH_3$ | —I | | | | | —S—$CH_3$ |
| lactam 47 | —$CH_3$ | —$NO_2$ | | | | | —S—$CH_3$ |
| lactam 48 | —$CH_3$ | | | | | | —S—$CH_3$ |
| lactam 49 | —$CH_3$ | —F | | | | | —S—$CH_3$ |

Ph = phenyl

β-lactam compounds encompassed within the scope of the present invention can have the general formula B:

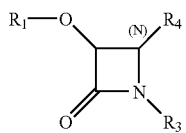

(B)

wherein $R_1$ is a hydrocarbon group having 1-8 carbon atoms and includes alkyl, alkenyl, and alkynyl groups;

$R_3$ is an organothio group;

$R_4$ is an aryl, heteroaryl, cycloalkyl, heterocycloalkyl, cycloalkenyl, or heterocycloalkenyl, any of which can be optionally substituted with $R_2$ wherein $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I; and (N) is, preferably a straight or branched 2-4 carbon alkyl, alkenyl, or alkynyl chain connecting the β-lactam ring to the $R_4$ group;

or a pharmaceutically acceptable salt, ester or amide thereof.

β-lactam compounds of the present invention can also have the following formula II:

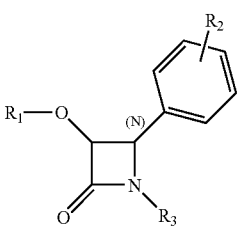

(II)

in which $R_1$ is a hydrocarbon group having 1-8 carbon atoms; $R_2$ is one or more halide, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I; (N) is, preferably a straight or branched 2-4 carbon alkyl, alkenyl, alkynyl, or alkynyl chain connecting the β-lactam ring to the phenyl; and $R_3$ is an organothio group; or a pharmaceutically acceptable salt, ester or amide thereof.

TABLE 2

N-thiolated β-lactam Compounds of formula II of the Invention

| Compound # | $R_1$ | $R_2$ (position on the phenyl ring) 2 | 3 | 4 | $R_3$ |
|---|---|---|---|---|---|
| lactam 33[a] | —CH$_3$ | | | | —S—CH$_3$ |
| lactam 34[b] | —CH$_3$ | | | | —S—CH$_3$ |
| lactam 37[c] | —CH$_3$ | | | | —S—CH$_3$ |
| lactam 38[c] | —CH$_3$ | | | | —S—(CH$_2$)$_2$OH |
| lactam 39[c] | —CH$_3$ | | | | —S-cyclohexyl |
| lactam 40[c] | —CH$_3$ | | | | —S—Ph |
| lactam 41[c] | —CH$_3$ | | | | —S—CH$_2$—Ph |

[a] where N = —(CH$_2$)$_2$—
[b] where N = —(CH)$_2$—
[c] where N = —C≡C—
Ph = phenyl β-lactam compounds of the present invention can also have the structure of Formula III:

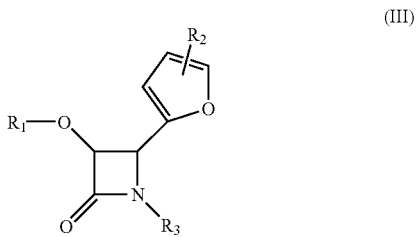

(III)

in which $R_1$ is a hydrocarbon group having 1-8 carbon atoms; $R_2$ is one or more halide, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, carboxylic ester group, —CHO, —COOH, or COX, wherein X is Cl, F, Br, or I; and $R_3$ is an organothio group; or a pharmaceutically acceptable salt, ester or amide thereof.

It will be appreciated by those skilled in the art that compounds of the invention having one or more chiral center(s) can exist in and be isolated in optically active and/or racemic forms. Some compounds can exhibit polymorphism. It is well known in the art how to prepare optically active forms (for example, by resolution of the racemic form by recrystallization techniques, by synthesis from optically-active starting materials, by chiral synthesis, or by chromatographic separation using a chiral stationary phase). It is to be understood that the present invention encompasses any racemic, optically-active, polymorphic, or stereoisomeric form, or mixtures thereof, of the compounds of the invention and methods of using such compounds as described herein.

As used herein, the term "alkyl" refers to a straight or branched chain alkyl moiety. Included within this group are, for example, methyl, ethyl, n-propyl, n-butyl, isobutyl, sec-butyl, tert-butyl, pentyl, isoamyl, hexyl, and octyl.

The term "alkenyl" refers to a straight or branched chain alkyl moiety having in addition one double bond. Included within this group are, for example, ethenyl, propenyl, 1- and 2-butenyl, pentenyl, and hexenyl.

The term "alkynyl" refers to a straight or branched chain alkyl moiety having in addition one triple bond. Included within this group are, for example, ethynyl, propynyl, 1- and 2-butynyl, pentynyl, and hexynyl.

The term "alkoxy" refers to an alknyl ether moiety wherein the term alkyl is as defined above. Included within this group are, for example, methoxy, ethoxy, n-propoxy, isopropoxy, n-butoxy, iso-butoxy, sec-butoxy, and tert-butoxy.

The term "acyl" refers to an alkyl or aryl group bonded through a carbonyl (R—C(O)—) group. Included within this group are, for example, acetyl and benzoyl.

The term "cycloalkyl" refers to a saturated alicyclic moiety, and includes benzofused cycloalkyls. Included within this group are, for example, cyclopropyl, cyclobutyl, cyclopentyl, cyclohexyl, cycloheptyl, cyclooctyl, and decalinyl. The term "benzofused cycloalkyl" refers to a benzene ring sharing a common bond with the ring of a cycloalkyl. Included within this group are, for example, indanyl and tetrahydronaphthyl.

The term "cycloalkenyl" refers to an alicyclic moiety having in addition one double bond. Included within this group are, for example, cyclopentenyl and cyclohexenyl.

The term "heterocycloalkyl" refers to a heterocyclic moiety having one or more heteroatoms selected from the group of N, O, and S, and includes benzofused heterocycloalkyls. Included within this group are, for example, pyrrolidinyl, pyrrolyl, piperidinyl, and morpholinyl. The term "benzofused heterocycloalkyl" refers to a benzene ring sharing a common bond with the ring of a heterocycloalkyl. Included within this group are, for example, indolinyl and tetrahydroquinolinyl.

The term "heterocycloalkenyl" refers to an alicyclic moiety having one or more heteroatoms selected from the group of N, O, and S, and having in addition one double bond. Included within this group is, for example, dihydropyranyl.

The term "aryl" refers to a homocyclic aromatic moiety that can be a single ring or multiple rings which are fused together or linked covalently. Included within this group are, for example, phenyl, indenyl, biphenyl, naphthyl, anthracenyl, and phenathracenyl group.

The term "heteroaryl" refers to an aromatic ring system of five to ten atoms of which at least one atom is selected from the group N, O and S. Included within this group are, for example, pyrolyl, furyl, thienyl, imidazolyl, oxazolyl, thiazolyl, pyrazolyl, pyridyl, pyrrimidinyl, indolyl, quinolinyl, and isoquinolinyl.

Preparation of the N-thiolated β-lactam Compounds

N-thiolated β-lactam compounds of the present invention can be synthesized according to the procedure given in Ren et al., 1998, *J. Org. Chem.* 63:8898-8917, which is incorporated herein by reference in its entirety. It will be apparent to one of ordinary skill in the art in the field of the present invention how the starting compounds and procedures below can be easily modified to produce other desired compounds, both those described herein, and others such as $R_2$ being one or more halogens in meta, para or ortho position on phenyl ring.

As can be understood with reference to Reaction Scheme 1 (below), while most antibiotics require demanding multi-step syntheses or semi-synthetic procedures to reach the final active substance, N-thiolated β-lactams such as 5 can be prepared in a single step from n-protio lactams 4 using a published procedure (Shah, N. V.; Cama, L. D. Synthesis of a Novel Carbapenem-Potassium (5R,6R)-1,1-Difluoro-2-phenyl-6-(1R-hydroxyethyl)-carbapeN-2-em-3-carboxylate. The Use of a New N-Protecting Group in β-lactam Synthesis. *Heterocycles* 1987, 25, 221). Although some of N-thiolated β-lactams are commercially available, most variants of the N-thiolated β-lactams can be prepared in only two chemical steps. The first step is a Staudinger coupling of an acid chloride 1 with an N-(4-methoxyphenyl) imine 2, followed by N-dearylation of β-lactam 3 with ceric ammonium nitrate. After that, the alkylthio group $SR^3$ is attached to the lactam nitrogen using an easily prepared phthalimide reagent. Yields for each of these steps are typically above 90% on a multigram scale regardless of the nature of the $R^1$, $R^2$ and $R^3$ groups. The compounds are generally obtained in purified form by crystallization directly from the crude reaction media, omitting the need for column chromatography or HPLC. The structure and purity of all compounds are determined by $^1H$ and $^{13}C$ NMR spectroscopy, infrared spectroscopy, mass spectrometry, and elemental analysis. Using this simple three-step procedure (see Reaction Scheme 1, below), N-thiolated β-lactams can be synthesized.

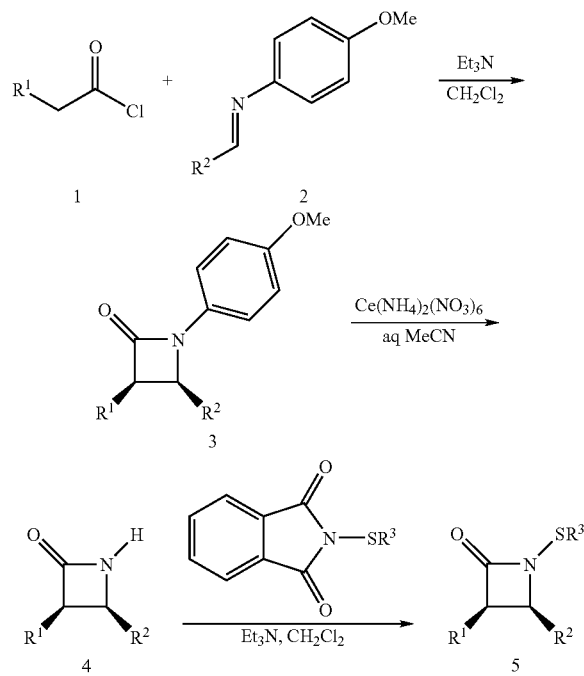

Reaction Scheme 1

The following general experimental procedures can be employed. All air- or moisture-sensitive procedures are performed under an argon atmosphere using glassware and syringes that are pre-dried in an oven overnight at 120° C., and assembled while still hot. The imines are prepared by heating equimolar amounts of the appropriate aldehyde and amine in refluxing benzene solution in the presence of a small amount of p-toluenesulfonic acid under Dean-Stark conditions, followed by filtering the cooled solution through an approximately one inch plug of silica gel to remove residual amine. The purity of the crude imine is checked by $^1H$ NMR prior to use. The acid chlorides are synthesized according to standard protocols by heating the corresponding carboxylic acid in thionyl chloride, removing residual volatiles by distillation, and used without further purification. THF and $Et_2O$ are distilled immediately prior to use from sodium/benzophenone under argon, and $CH_2Cl_2$ is freshly distilled from $CaH_2$ under $N_2$. Reactions are followed by TLC with fluorescence indicator ($SiO_2$-60, F-254) or 1% aqueous $KMnO_4$ stain. Flash chromatography is performed using 40 μm silica gel. $^1H$ NMR spectra are recorded at 300, 360, 400 or 500 MHz and $^{13}C$ NMR spectra are obtained at 75, 100, or 125 MHz. IR spectra are obtained as a thin film smeared onto NaCl plates. Mass spectra are run using electron impact or chemical ionization methods.

Methods of Treatment

As noted above, the present invention provides methods of treating conditions that arise as the result of dysregulation of the normal process of cell death in the cells or tissue of a subject. Dysregulation of the cell death process is associated with many conditions. Such conditions include tumors, cancers, neoplasms, autoimmune disorders (e.g., systemic lupus erythematosus, rheumatoid arthritis, graft-versus-host disease, Sjogren's syndrome and myasthenia gravis); hyperproliferative disorders (such as B or T cell lymphoma, neuroblastoma, and chronic lymphocytic leukemia), chronic inflammatory conditions (such as psoriasis, asthma, or Crohn's disease), other conditions such as osteoarthritis and atherosclerosis, and those induced by DNA and/or RNA viral infections, wherein the viruses include, but are not limited to, herpes virus, papilloma virus and human immunodeficiency virus (HIV).

In neoplasms, for example, normal cell death is inhibited, allowing hyperproliferative growth of cells. Aberrant functioning of normal cell death can also result in serious pathologies including autoimmune disorders, viral infections, conditions induced by viral infections, neurodegenerative diseases, and the like. The present invention provides methods of treating these and other conditions. Thus, the subject invention also concerns methods for treating or preventing hyperproliferative disorders in a patient. These disorders are treated by administering an effective amount of a β-lactam compound of the present invention. These β-lactam compounds are therapeutically effective on their own.

Conditions that benefit from treatment with the β-lactam compounds of the present invention share the common etiology of dysregulation of the cell death process. Normal apoptosis occurs via several pathways, with each pathway having multiple steps. The methods described herein are useful in treating dysregulated apoptosis and necrosis. Without being limited by one theory, the effective β-lactam compounds described herein induce or promote cell death when the cell death process is malfunctioning. Thus, in addition to treating conditions associated with dysregulated apoptosis, the compounds of this invention also treat conditions in which there is not any apoptotic defect. For example, in certain viral infections, while there is not any apoptotic defect, cell death can be promoted by inducing necrosis.

One aspect of the subject invention concerns methods for inducing tumor cell death or inhibiting tumor cell proliferation by contacting or exposing a tumor cell to an N-thiolated β-lactam compound of the present invention. In a further aspect, the present invention concerns methods for inducing DNA damage, inhibition of DNA replication, p38 MAP kinase activation, caspase cascade activation, and/or mitochondrial cytochrome C release into cytoplasm in a tumor cell comprising contacting or exposing the tumor cell to an N-thiolated β-lactam compound of the present invention. In one embodiment of the present methods, the tumor cell is from a mammal. In a preferred embodiment, the tumor cell is from a human.

The subject invention also concerns methods for treating or preventing cancer in a patient, wherein the method comprises administering to the patient an effective amount of an N-thiolated β-lactam compound of the present invention. The subject method can be used to treat or prevent cancers including, but not limited to, lung cancer, breast cancer, colon cancer, prostate cancer, melanomas, pancreatic cancer, stomach cancer, liver cancer, brain cancer, kidney cancer, uterine cancer, cervical cancer, ovarian cancer, cancer of the urinary tract, gastrointestinal cancer, head-and-neck cancer, or leukemia. In one embodiment of the subject method, the N-thiolated β-lactam compound is administered orally, intramuscularly, and/or transdermally. Preferably, the patient being treated is a mammal, and more preferably, the mammal is a human.

To "treat" as intended herein, means to induce cell death (wherein the cell death is either apoptotic or necrotic) in cells or tissue which are causative (primary or distal) of the disorder being treated. For example, in hyperproliferative disorders, the methods will treat the disorder by inducing apoptosis of the hyperproliferative cells, such as neoplastic cells. In this embodiment, reduction in tumor size or tumor burden is one means to identify that the object of the method has been met. In other aspects, treatment encompasses restoration of immune function or regulation of immune dysfunction, as in autoimmune disorders and chronic inflammatory conditions.

Methods of Identifying Potential Therapeutic Agents

Also provided herein is an assay to screen for β-lactam compounds as potential agents to effectively treat conditions associated with the dysregulation of the apoptotic or necrotic pathway.

The method comprises contacting a dysregulated cell, i.e., a cell affected by the disorder, such as a tumor cell or other hyperproliferative condition, with an effective amount of a β-lactam compound to be screened. In a further aspect of this invention, an untreated control cell is further assayed and compared to the tumor cell treated with a β-lactam compound.

A preferred method for screening a β-lactam compound or an analog thereof for its ability to induce tumor cell death or to inhibit tumor cell proliferation comprises: contacting a culture of tumor cells with the β-lactam compound, preparing a lysate of the β-lactam treated cells, and measuring apoptosis-specific caspase-3 activity or PARP cleavage; and relating the measured apoptosis-specific caspase-3 activity or PARP cleavage to the β-lactam ability to induce tumor cell death or to inhibit tumor cell proliferation wherein an increase in either caspase-3 activity or PARP cleavage as compared to untreated tumor cells indicates that the compound or analog thereof is capable of inducing cancer cell death or inhibiting cancer cell proliferation. A skilled artisan will readily recognize that any tumor or neoplastic cell line is suitable for screening and a variety of assays can be used. For example, the tumor cell can be a leukemia cell or a solid tumor cell.

To identify these potential β-lactam therapeutic agents, appropriate assay conditions (e.g., incubation time, temperature, culture maintenance medium, etc.) can be readily determined by one of skill in the art, some of which are exemplified in the Examples below.

In a further aspect, the N-thiolated β-lactam compounds of this invention are further characterized and identified by their ability to induce caspase-8, caspase-9 and caspase-3 activation, S-phase arrest, DNA strand breaks, or p38 MAP kinase activation.

Use of β-lactam Compounds for Preparing Medicaments

The β-lactam compounds of the present invention are also useful in the preparation of medicaments to treat a variety of conditions associated with dysregulation of cell death as described above. Thus, one of skill in the art would readily appreciate that any one or more of the compounds described more fully below, including the many specific embodiments, can be used by applying standard pharmaceutical manufacturing procedures to prepare medicaments to treat the many disorders described herein above. Such medicaments can be delivered to the subject by using delivery methods that are well-known in the pharmaceutical arts.

Compositions and Formulations

Although β-lactam compounds of the present invention can be administered alone, β-lactam compounds can also be administered as a pharmaceutical formulation comprising at least one additional active ingredient, together with one or more pharmaceutically acceptable carriers therefor. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration can be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Formulations suitable for topical administration to the eye also include eye drops wherein the active ingredient is dissolved or suspended in a suitable carrier, especially an aqueous solvent for the agent.

Formulations for rectal administration can be presented as a suppository with a suitable base comprising, for example, cocoa butter or a salicylate. Formulations suitable for vaginal administration can be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose sealed containers, such as for example, ampoules and vials, and can be stored in a freeze-dried (lyophilized) condition requiring only the addition of the sterile liquid carrier, for example water for injections, immediately prior to use. Extemporaneous injection solutions and suspensions can be prepared from sterile powders, granules and tablets of the kind previously described.

Preferred unit dosage formulations are those containing a daily dose or unit, daily subdose, as herein above-recited, or an appropriate fraction thereof, of an agent. It should be understood that in addition to the ingredients particularly mentioned above, the formulations of this invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Pharmaceutical Delivery

Various delivery systems are known and can be used to administer a therapeutic agent of the invention, e.g., encapsulation in liposomes, microparticles, microcapsules, receptor-mediated endocytosis (see, e.g. Wu et al., 1987, *J. Biol. Chem.* 262:4429-4432), and the like. Methods of delivery include, but are not limited to, intra-arterial, intramuscular, intravenous, intranasal, and oral routes. In a specific embodiment, the pharmaceutical compositions of the invention can be administered locally to the area in need of treatment; such local administration can be achieved by, for purpose of illustration and not limitation, local infusion during surgery, by injection, or by means of a catheter.

Therapeutic amounts can be empirically determined and will vary with the pathology being treated, the subject being treated, and the efficacy and toxicity of the agent. Similarly, suitable dosage formulations and methods of administering the agents can be readily determined by those of skill in the art.

The pharmaceutical compositions can be administered orally, intranasally, parenterally or by inhalation therapy, and can take the form of tablets, lozenges, granules, capsules, pills, ampoules, suppositories or aerosol form. They can also take the form of suspensions, solutions, and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

Ideally, the agent should be administered to achieve peak concentrations of the active compound at sites of the disease. Peak concentrations at disease sites can be achieved, for example, by intravenously injecting of the agent, optionally in saline, or orally administering, example, a tablet, capsule or syrup containing the active ingredient.

Kits

Furthermore, the invention also comprehends a kit wherein N-thiolated β-lactam compounds of the present invention are provided. The kit can include a separate container containing a suitable carrier, diluent or excipient. The kit can also include additional anti-cancer, anti-tumor or antineoplastic agent, antioxidant, DNA topoisomerase II enzyme inhibitor or an inhibitor of oxidative DNA damage or antimicrobial, or cyclo-oxygenase and/or lipoxygenase, NO or NO-synthase non-steroidal anti-inflammatory, apoptosis and platelet aggregation modulating or blood or in vivo glucose modulating agent and/or an agent which reduces or alleviates ill effects of antineoplastic, anti-tumor or anti-cancer agents, antioxidant, DNA topoisomerase II enzyme inhibitor or antimicrobial, or cyclo-oxygenase and/or lipoxygenase, NO or NO-synthase, apoptosis, platelet aggregation and blood or in vivo glucose modulating and/or non-steroidal anti-inflammatory agents for co- or sequential-administration. The additional agent(s) can be provided in separate container(s) or in admixture with the inventive polyphenol compounds. Additionally, the kit can include instructions for mixing or combining ingredients and/or administration.

From the above description of the invention, one of skill in the art readily understands that the various methods of treatment, diagnostic methods, use of compounds to prepare medicaments, delivery of such medicaments, and the making of the compounds, can be practiced in many different ways, as exemplified by the many examples presented below.

Abbreviations used herein include Apaf-1, apoptotic protease-activating factor 1; PARP, poly(ADP-ribose) polymerase; MAP, mitogen-activated protein; MTT, 3-(4,5-dimethylthiazol-2-yl)-2,5-diphenyltetrazolium bromide; Ab, antibody; COX, cytochrome oxidase unit II; TUNEL, terminal deoxynucleotidyl transferase-mediated UTP nick-end labeling; Z-IETD-AFC, N-benzyloxycarbonyl-Ile-Glu-Thr-Asp-7-amino-4-trifluoromethyl coumarin; Ac-LEHDAFC, N-acetyl-Leu-Glu-His-Asp-7-amino-4-trifluoromethyl coumarin; Ac-DEVD-AMC, N-acetyl-Asp-Glu-Val-Asp-amino-4-methylcoumarin; Ac-IETD-CHO, N-acetyl-Ile-Glu-Thr-Asp-CHO (aldehyde); Z-LE(OMe)HD(OMe)-FMK, N-benzyloxycarbonyl-Leu-Glu(OMe)-His-Asp(OMe)-fluoromethyl ketone; Ac-DEVD-CHO, N-acetyl-Asp-Glu-Val-Asp-CHO (aldehyde); Boc-D-FMK, N-tert-butoxycarbonyl-Asp-fluoromethyl ketone; PD169316, 4-(4-fluorophenyl)-2-(4-nitrophenyl)-5-(4-pyridyl)-1H-imidazole; PBS, phosphate-buffered saline; TdT, terminal deoxynucleotidyl transferase; SAR, structure-activity relationship; DMSO, dimethyl sulfoxide; MT-21, a previously reported synthetic γ lactam.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be con-

EXAMPLE 1

Synthesis of N-Thiolated β-Lactam Compounds

N-thiolated β-lactam compounds can be synthesized as shown in the reaction scheme below. See: Staudinger, 1907, *Liebigs Ann. Chem.* 356:51, Georg et al., 1993, in: "The Organic Chemistry of β-lactams", Verlag Chemie: New York, pp. 295-368.

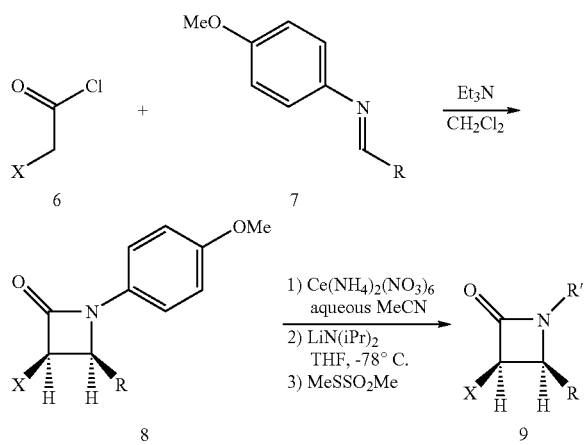

Procedure for the Preparation of N-aryl Protected β-lactams.

To a stirred solution of Et$_3$N (1.25 mL, 9.0 mmol) and imine (7, R═CCPh) (1.88 g, 8.0 mmol) in CH$_2$Cl$_2$ (75 mL) at room temperature is added via cannula a solution of methoxyacetyl chloride (6, X═OMe) (0.91 g, 10.0 mmol) in CH$_2$Cl$_2$ (20 mL). The reaction mixture is stirred at room temperature for 30 min, poured into 5% aqueous HCl (75 mL), and extracted with CH$_2$Cl$_2$ (3×50 mL). The combined organic layers are dried over MgSO$_4$, filtered, and evaporated to give a brown oil that slowly crystallizes upon standing. Flash chromatography (2:1 CH$_2$Cl$_2$:hexanes and then CH$_2$Cl$_2$) of the crude material affords 2.2 g (89%) of β-lactam (8, X═OMe, R═CCPh): white solid; 116-117 C; $^1$H NMR (400 MHz, CDCl$_3$) δ 7.54-7.35 (m, 7H), 6.9 (d, J=7.8 Hz, 2H), 4.96 (d, J=4.8 Hz, 1H), 4.81 (d, J=4.8 Hz, 1H), 3.78 (s, 3H), 3.70 (s, 3H); $^{13}$C NMR (75 MHz, CDCl$_3$) δ 163.1, 157.4, 132.6, 129.3, 129.2, 129.1, 128.8, 119.1, 115.0, 84.8, 81.7, 59.1, 56.1, 56.0, 50.3; IR (thin film) 1752 cm$^{-1}$ (β-lactam C═O). Anal. Calcd for C$_{19}$H$_{17}$NO$_3$: C, 74.25; H, 5.58; N, 4.56. Found: C, 74.10; H, 5.60; N, 4.57.

Procedure for the Dearylation of N-aryl β-lactams.

To a solution of N-p-methoxyphenyl β-lactam (8, X═OMe, R═CCPh) (2.2 g, 7.2 mmol) in CH$_3$CN (100 mL) at 0° C. is added 100 mL of an aqueous solution of ammonium cerium(IV) nitrate (11.8 g, 21.6 mmol) over 5 min. The reaction mixture is stirred for 25 min and then poured into aqueous 5% NaHSO$_3$ (100 mL), and the aqueous mixture is extracted with Et$_2$O (3×50 mL). The combined organic layers are treated with 5% NaHCO$_3$ (100 mL), and the aqueous layer is back-washed with one portion of diethyl ether (50 mL). The combined organic layers are dried over MgSO$_4$, filtered, and evaporated. Flash chromatography of the crude mixture affords 1.28 g (89%) of (9, X═OMe, R═CCPh, R'═H): white solid (mp 121-122 C); 1H NMR (400 MHz, CDCl$_3$) δ 7.42-7.35 (m, 5H), 6.80 (broad s, 1H), 4.72 (d, J=4.8 Hz, 1H), 4.60 (d, J=4.8 Hz, 1H), 3.60 (s, 3H); $^{13}$C NMR (75 MHz, CDCl$_3$) δ 167.5, 132.4, 129.4, 128.9, 122.7, 87.9, 87.1, 83.7, 58.8, 46.6; HRMS (CI, isobutane) calcd for C$_{12}$H$_{11}$NO$_2$ (M+1) 202.0865, obsd 202.0884. Anal. Calcd for C$_{12}$H$_{11}$NO$_2$: C, 71.63; H, 5.51; N, 6.96. Found: C, 71.55; H, 5.53; N, 6.91.

Procedure for the N-methylthiolation of β-lactams.

To a solution of (9, X═OMe, R═CCPh, R'═H) (1.28 g, 6.4 mmol) in THF at −78° C. is added n-butyllithium (5.0 mL, 1.38 M in hexanes, 6.9 mmol). After 30 minutes, methyl methanethiolsulfonate (0.85 g, 6.6 mmol) is added and the reaction mixture is stirred for 12 hours with warming to room temperature. The mixture is poured into 5% aqueous NH$_4$Cl (50 mL) and extracted with CH$_2$Cl$_2$ (3×50 mL). The combined organic layers are dried over MgSO$_4$, filtered, and evaporated. Flash chromatography of the crude mixture affords 1.26 g (80%) of N-methylthio compound (9, X═OMe, R═CCPh, R'═SMe): colorless solid; mp 74-76 C; $^1$H NMR (400 MHz, CDCl$_3$) δ 7.42 (d, J=8.8 Hz, 2H), 7.30 (m, 3H), 4.72 (d, J=4.8 Hz, 1H), 4.63 (d, J=4.8 Hz, 1H), 3.56 (s, 3H), 2.58 (s, 3H); $^{13}$C NMR (75 MHz, CDCl$_3$) δ 169.8, 132.4, 129.6, 129.0, 122.5, 89.3, 86.6, 82.5, 59.0, 55.1, 22.7; IR (thin film) 1772 cm$^{-1}$ (β-lactam C═O). HRMS (CI, isobutane) calculated for C$_{13}$H$_{13}$NO$_2$S (M+1) 248.0742, obsd 248.0734. Anal. calculated for C$_{13}$H$_{13}$NO$_2$S: C, 63.13; H, 5.30. Found: C, 63.08; H, 5.33.

Materials and Methods for Examples 2-7

Materials.

Fetal calf serum, propidium iodide, MTT [3-(4,5-dimethylthiazol-2-yl)-2,5-diphenyltetrazolium bromide], trypan blue, and RNase A are purchased from Sigma (St. Louis, Mo.). RPMI 1640, Dulbecco's modified Eagle's medium, penicillin and streptomycin are purchased from Life Technologies, Inc. (Rockville, Md.). Polyclonal antibodies to human PARP is from Boehringer Mannheim (Indianapolis, Ind.); to caspase-8 (Ab-1) from Oncogene Research Products (Boston, Mass.). Monoclonal antibodies to Tyr-182 phosphorylated and total p38 protein are from Santa Cruz Biotechnology (Santa Cruz, Calif.); to caspase-9 (Ab-2) and caspase-3 (Ab-1) are from Oncogene Research Products; to cytochrome C from BD PharMingen (San Diego, Calif.); to cytochrome oxidase unit 11 (COX) from Molecular Probes (Eugene, Oreg.). Goat antibody to actin and anti-rabbit IgG-horseradish peroxidase are from Santa Cruz Biotechnology. The APO-DIRECT Kit for TUNEL staining is purchased from BD PharMingen. [methyl-$^3$H]Thymidine is obtained from Amersham Pharmacia (Piscataway, N.J.). Z-IETD-AFC (the specific caspase-8 substrate), Ac-LEHD-AFC (the specific caspase-9 substrate), Ac-DEVD-AMC (the specific caspase-3 substrate), Ac-IETD-CHO (the specific caspase-8 inhibitor), Z-LE(OMe)HD(OMe)-FMK (the specific caspase-9 inhibitor), Ac-DEVD-CHO (the specific caspase-3 inhibitor), Boc-D-FMK (a pan caspase inhibitor), and PD169316 (the specific p38 MAP kinase inhibitor) are obtained from Calbiochem (San Diego, Calif.).

Synthesis of β-Lactams.

β-Lactams 1-7 (FIG. 1) are prepared as racemates (with cis stereochemistry) using a procedure described previously (Ren et al., 1998; Turos et al., 2000).

Cell Cultures, Protein Extraction and Western Blot Assay.

Human Jurkat T cells were cultured in RPMI 1640, supplemented with 10% fetal calf serum, 100 units/ml of penicillin and 100 μg/ml of streptomycin. Human breast cancer MCF-7 and MDA-MB-231 cells, human prostate cancer PC-3 cells, and human head-and-neck cancer PCI-13 cells were grown in Dulbecco's modified Eagle's medium containing 10% fetal calf serum, penicillin and streptomycin. All the cell lines were maintained in a 5% $CO_2$ atmosphere at 37° C. A whole cell extract was prepared as described previously (An et al., 1998). Briefly, cells are harvested, washed with PBS and homogenized in a lysis buffer (50 mM Tris-HCl, pH 8.0, 5 mM EDTA, 150 mM NaCl, 0.5% NP-40, 0.5 mM PMSF, and 0.5 mM dithiothreitol) for 30 min at 4° C. After that, the lysates are centrifuged at 14,000×g for 30 min and the supernatants are collected as whole cell extracts. Equal amounts of protein extract (50 μg) are resolved by SDS-polyacrylamide gel electrophoresis and then transferred to a nitrocellulose membrane (Schleicher & Schuell, Keene, N H) using a Semi-Dry Transfer System (BIO-RAD; Hercules, Calif.). The enhanced chemiluminescence (ECL) Western Blot analysis is then performed using specific antibodies to the proteins of interest.

Cell-Free Caspase Activity Assay.

Cell-free caspase activities were determined by measuring the cleavage of AMC or AFC groups from each respective caspase substrate, as described for example by Nam S, et al., 2001, Ester bond-containing tea polyphenols potently inhibit proteasome activity in vitro and in vivo. *J. Biol Chem* 276: 13322-30 with some modifications. Briefly, a prepared protein extract (20 μg) is incubated in a buffer containing 50 mM Tris/pH 8.0 along with each respective caspase substrate at 20 μM in a 96 well plate. The reaction mixture is incubated at 37° C. for 2 h. After incubation, the liberated fluorescent AMC or AFC groups are measured by a Wallac Victor 1420 Multilabel counter (Turku, Finland) with 355/460 rAM and 405/535 nM filters, respectively.

Trypan Blue Assay.

The trypan blue exclusion assay was performed by injecting 10 μl of cell suspension containing 0.2% trypan blue dye into a hemoicytometer and counting. Numbers of cells that absorbed the dye and those that excluded the dye are counted, from which the percentage of non-viable cell number to total cell number is calculated.

Subcellular Fractionation.

Both cytosolic and mitochondria fractions were isolated at 4° C. using a protocol by Gao G and Dou QP, 2000, N-terminal cleavage of bax by calpain generates a potent proapoptotic 18-kDa fragment that promotes bcl-2-independent cytochrome C release and apoptotic cell death. *J Cell Biochem* 80:53-72 with some modifications. At each time point, cells were washed twice with PBS, resuspended in a hypotonic buffer containing 20 mM HEPES (pH 7.5), 1.5 mM $MgCl_2$, 5 mM KCl and 1 mM DTT, and incubated on ice for 10 min. The cells are dounced 30 times, and the lysate is centrifuged at 2,000×g for 10 min. The supernatant is collected and centrifuged again at the same condition. The resulting supernatant is then centrifuged at 20,500×g for 30 min, followed by collection of both the supernatant (cytosol) and pellet fractions. The pellet is washed twice with a buffer containing 210 mM mannitol, 70 mM sucrose, 5 mM Tris-HCl (pH 7.5) and 1 mM EDTA, and resuspended in the lysis buffer as the mitochondria fraction.

Flow Cytometry.

Cell cycle analysis based on DNA content was performed as described by An B, et al. (1998) Novel dipeptidyl proteasome inhibitors overcome Bcl-2 protective function and selectively accumulate the cyclin-dependent kinase inhibitor p27 and induce apoptosis in transformed, but not normal, human fibroblasts. *Cell Death Differ* 5:1062-75. At each time point, cells are harvested, counted, and washed twice with PBS. Cells ($5 \times 10^6$) are suspended in 0.5 ml PBS, fixed in 5 ml of 70% ethanol for at least 2 h at −20° C., centrifuged, resuspended again in 1 ml of propidium iodide staining solution (50 μg propidium iodide, 100 units RNase A and 1 mg glucose per ml PBS), and incubated at room temperature for 30 minutes. The cells are then analyzed with FACScan (Becton Dickinson Immunocytometry, CA), ModFit LT and WinMDI V.2.8 cell cycle analysis software (Verity Software; Topsham, Me.). The cell cycle distribution is shown as the percentage of cells containing $G_1$, S, $G_2$, and M DNA judged by propidium iodide staining. The apoptotic population is determined as the percentage of cells with sub-$G_1$ (<$G_1$) DNA content.

$^3$H-Thymidine Incorporation Assay.

Incorporation of $^3$H-thymidine into cells was measured as disclosed in Smith D M and Dou Q P, 2001, Green tea polyphenol epigallocatechin inhibits DNA replication and consequently induces leukemia cell apoptosis. *Int J Mol Med* 7:645-52. Jurkat T cells are pre-treated with a selected lactam for the indicated number of hours, followed by co-incubation with 2 μl/ml of [methyl-$^3$H]-thymidine [80 Ci (1.5 TBq)/mMol] at 37° C. for 2 hours. After harvesting, the cell pellet is washed with PBS, resuspended in 0.5 ml of PBS and collected on a glass microfiber filter. The filter is then washed with 5 ml/filter of PBS, followed by 5 ml/filter of ice-cold 0.1N NaOH and 5 ml/filter of ethanol. The filters containing fixed DNA are dried, and the remaining radioactivity is measured on a scintillation counter.

TUNEL Assay.

Terminal deoxynucleotidyl transferase-mediated UTP nick end labeling (TUNEL) was performed to determine the extent of DNA strand breaks. TUNEL assay was performed with an APO-Direct kit per the manufacturer's instructions. In brief, cells are fixed in 1% paraformaldehyde and ethanol at 20° C. overnight and then permeabilized with Proteinase K. After permeabilization, Fluorescein conjugated dNTP's and TdT enzyme (Terminal Deoxynucleotidyl Transferase) are added to the cells. The TdT enzyme is then able to label free ends of DNA with Fluorescein conjugated dNTPs that could then be detected by flow cytometry. For the fluorescence microscopy of TUNEL-positive cells, Jurkat T cells were labeled and analyzed in accordance with the manufacturer's instructions (see for example, An et al., 1998, supra).

MTT Assay.

MCF-7, MDA-MB-231, PC-3 and PCI-13 cells were grown to 50% confluency in a 24 well plate. Triplicate wells of cells were then treated with 50 μM lactam 1 for 24 hours. A stock 5 mg/ml of MTT in serum-free media was then added to the cell cultures at a final concentration of 1 mg/ml, followed by a 3 hour incubation at 37° C. After cells crystallized, the media was removed and DMSO added to dissolve the metabolized MTT product. The absorbance was then measured on a Wallac Victor 1420 Multilabel counter at 540 nM.

Nuclear Staining Assay.

To assay nuclear morphology, both the detached or remaining attached solid tumor cells were washed with PBS, fixed with 70% ethanol for 1 hour, and stained with Hoechst 33342

(50 μM) for 30 minutes. The nuclear morphology of cells was visualized by a fluorescence microscope.

EXAMPLE 2

Screen for Apoptotically Active β-Lactams

A library of β-lactam analogs was screened for their ability to induce apoptosis. A representative group of 7 compounds and their structures is shown in FIG. 1. The screening procedure is accomplished by treating human Jurkat T cells with each compound at 50 μM for 8 hours. This is followed by preparation of cell lysates and measurement of apoptosis-specific caspase-3 activation (by cell-free caspase-3 activity assay) and PARP cleavage (by Western blotting).

Figure 2C:
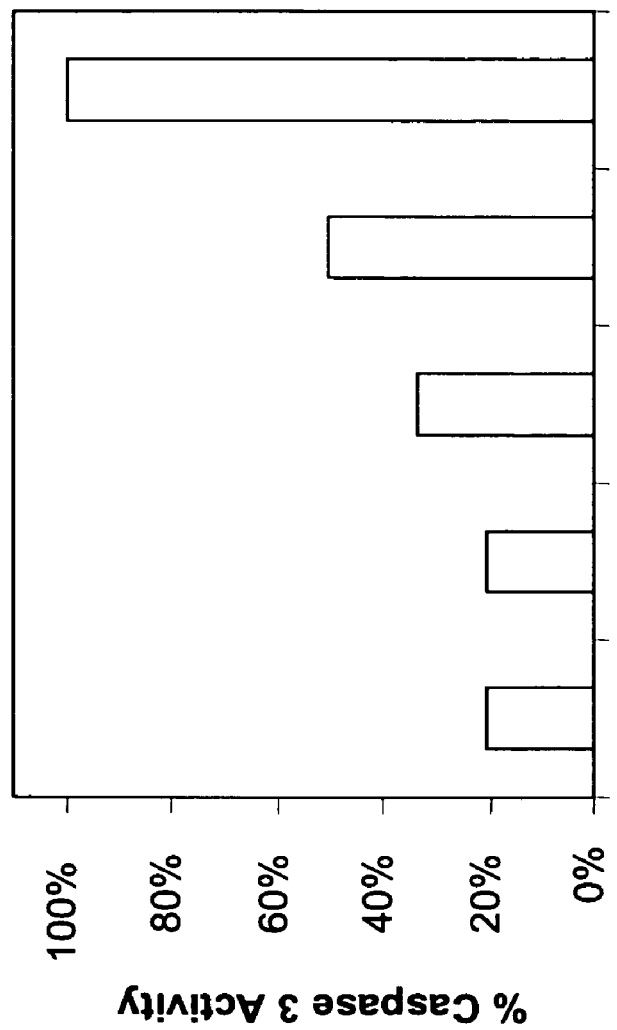

Among the tested compounds, lactam 1 was found to have the greatest potency to induce caspase-3 activation and PARP cleavage within 8 hours of treatment (FIGS. 2A and 2B). Several important structure-activity relationships (SARs) were observed. First, the N-methylthio group is required for the apoptosis-inducing activity of lactam 1. Lactam 2, which is an analog of lactam 1 that lacks the N-methylthio group (FIG. 1), induces neither caspase-3 activation nor PARP cleavage (FIGS. 2A and 2B, lactam 2 vs. lactam 1). In fact, lactam 2-treated cells showed no morphological changes, similar to that observed for DMSO (vehicle)-treated cells (FIGS. 2A and 2B, lactam 2 vs. D, data not shown).

The second SAR observed was that an increase in the number of carbons on the N-thio group was inversely proportional to the apoptosis-inducing ability of these β-lactams. An increase from one carbon (lactam 1) to two carbons (lactam 3) in this chain decreased ~50% of caspase-3 activity and PARP cleavage (FIGS. 2A and 2B, lactam 1 vs. lactam 3). A further increase to four carbons on the N-thio group (lactam 4) causes ~65% decrease in the apoptosis-inducing activity (FIGS. 2A and 2B, lactam 4 vs. lactam 1). Replacement of the N-methylthio with a N-benzylthio group (FIG. 1, lactam 7) also decreased the apoptosis-inducing activity by ~70% (FIGS. 2A and 2B, lactam 1 vs. lactam 7).

Another SAR was associated with the chlorophenyl group in lactam 1. Lactams 1, 5, and 6 are isomers with the chlorine group at ortho-, meta- and para-positions, respectively, on the phenyl ring (FIG. 1). Although both lactams 5 and 6 have similar potency in inducing caspase-3 activity and PARP cleavage, both of them are less potent than lactam 1 (by ~20%; FIGS. 2A and 2B). Based on these results, lactam 1 was chosen as a lead compound for further apoptosis and cell cycle studies.

EXAMPLE 3

Lactam 1-Induced Apoptosis is Caspase-Dependent and Associated with Cytochrome C Release Lactam 1-induced apoptosis was studied by performing both kinetics and concentration-response experiments. When Jurkat T cells were treated with 50 μM lactam 1 for 2, 4, 6, 8, 12 or 24 hours, apoptosis occurred in a time-dependent manner (FIGS. 3A and 3B). The PARP cleavage fragment p85 appears after 4 hours of treatment and its levels increase afterwards (FIG. 3A). Associated with this, the non-viable cell population, as determined by a trypan blue exclusion assay, increased by 20% at 4 hours, and further increased to 60% after 24 hours of treatment with lactam 1 (FIG. 3B).

Activation of caspase-8, caspase-9 and caspase-3 was measured by both cell-free activity assay (FIG. 3C) and Western blot analysis (FIG. 3D) to determine which caspases are activated during lactam 1-induced apoptosis. The caspase-8 activity was detected at 2 hours and later time points, with a maximal level at 6 hours (FIG. 3C). Western blot assay confirms cleavage and activation of caspase-8 at 2 hours with peaking amounts of caspase-8 fragment at 6 hours (MW 18 kDa; FIG. 3D). Consistent with caspase-8 activation, a 15-kDa fragment of Bid (Li et al., 1998) was observed as early as 2 hours after lactam 1 treatment, and peaks at 6 hours (FIG. 3D). The activity of caspase-9 is first detected at 4 hours and then increases afterwards (FIG. 3C). The increased level of the caspase-9 activity was associated with increased levels of the active caspase-9 fragment (MW 35 kDa; FIG. 3D). However, caspase-9 activity levels (by enzyme activity assay) and cleavage fragment amounts (by Western blot) were lower than those detected for caspase-8 (FIGS. 3C and 3D). The cell-free caspase-3 activity was also observed first at 4 hours and dramatically increased after 6 hours treatment (FIG. 3C), in very similar kinetics to that of caspase-3 cleavage detected by Western blotting (FIG. 3D). Furthermore, kinetically, caspase-3 activation is parallel to PARP cleavage (FIGS. 3, 3C, 3D vs. A), which agrees with the observation that caspase-3 is responsible for cleaving PARP (Lazebnik Y A, Kaufmann S H, Desnoyers S, Poirier G G and Earnshaw W C, 1994, Cleavage of poly(ADP-ribose) polymerase by a proteinase with properties like ICE. *Nature* 371:346-7). Lactam 1-induced apoptosis is associated with activation of these caspases.

It has been shown that MT-21, a synthetic compound with a β-lactam ring (a different class of structures from the β-lactams studied here) is able to induce mitochondrial cytochrome C release and apoptotic cell death (Watabe M, Machida K and Osada H, 2000, MT-21 is a synthetic apoptosis inducer that directly induces cytochrome c release from mitochondria. *Cancer Res* 60:5214-22). Whether lactam 1 is able to induce cytochrome C release from the mitochondria was examined. In an experiment similar to that associated with FIG. 3, Jurkat T cells were treated with lactam 1 for up to 12 hours, followed by isolation of cytosolic and mitochondrial fractions and measurement of the cytochrome C levels (FIG. 4). High levels of mitochondrial cytochrome C were detected in untreated cells, associated with low levels of cytosolic cytochrome C (FIG. 4A). After 2 to 4 hours treatment with lactam 1, levels of mitochondrial cytochrome C decreased while those of cytosolic cytochrome C significantly increased (FIG. 4A), indicating release of cytochrome C from the mitochondria. Although the mitochondrial cytochrome C levels further decreased after 6 hours or longer treatment, little or no cytochrome C is detected in the cytosol (FIG. 4A), suggesting loss of cytosolic cytochrome C in the later stages of apoptosis (compare to FIG. 3B). The observed cytochrome C release from mitochondria to the cytosol is not an artifact as constitutive levels of the mitochondria-specific COX (FIG. 4B) and the cytosolic β-actin protein (FIG. 4C) were also observed. Release of cytochrome C began prior to activation of caspase-3 (FIGS. 4 vs. 3).

Jurkat T cells were then treated for 8 hours with various concentrations of lactam 1 (FIG. 5). Induction of apoptosis-specific PARP cleavage was dependent on the concentrations of lactam 1 used. Low levels of p85 PARP fragment were detected when 20 μM lactam 1 is used, which further increased using 30 and 40 μM, and significantly increased using 50 μM. At 60 μM lactam 1 caused almost complete degradation of both the intact PARP protein and the p85 PARP fragment (FIG. 5A). Loss of membrane permeability was also found, a late event in apoptosis (Earnshaw W C. 1995, Nuclear changes in apoptosis. *Curr Opin Cell Biol* 7:337-43; Wyllie A H, Kerr J F and Currie A R, 1980, Cell death: the significance of apoptosis. *Int Rev Cytol* 68:251-306), and was also lactam 1-concentration-dependent: ~10% at 20-40 µM, ~30% at 50 µM, and ~80% at 60 µM (FIG. 5B).

Figure 5A:
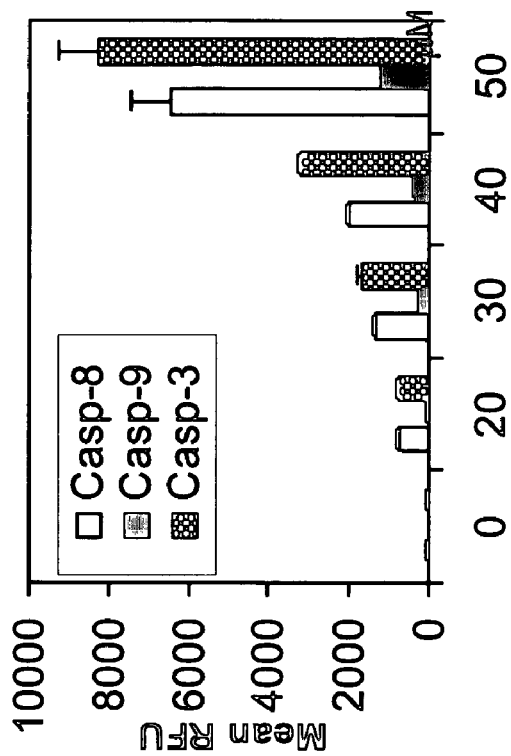
FIGS. 5A-D show that apoptosis induced by lactam 1 is concentration-dependant. Jurkat T cells are treated with increasing concentrations of lactam 1 for 8 hours, followed by assaying for PARP cleavage (FIG. 5A), trypan blue incorporation (FIG. 5B), and cell-free caspase-8, caspase-9 and caspase-3 activities (FIG. 5C). Results are representative of 3-5 different experiments. Standard deviations are given with error bars from a mean of at least 3 different experiments in B and C.
Figure 5B:
Figure 5C:
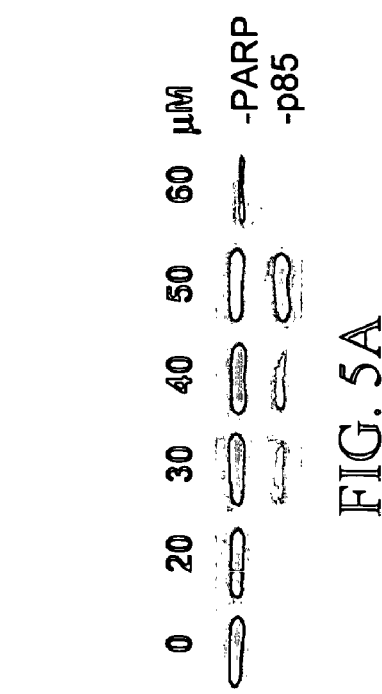
Figure 5D:
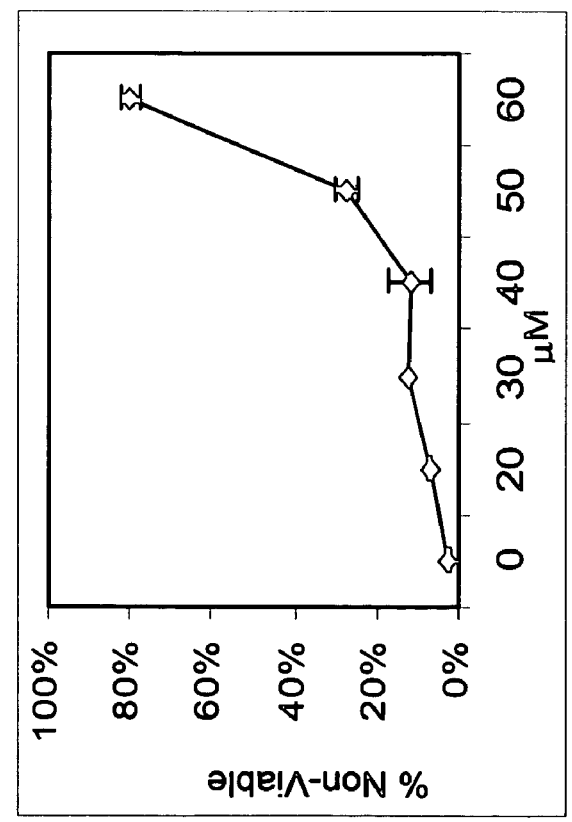

When a cell-free caspase activity assay was performed, activation of caspase-8, caspase-9 and caspase-3 was also found to depend on concentrations of lactam 1 (FIG. 5C). Compared to lysates of untreated cells (0 µM), the levels of caspase-8 increased by 2-fold when 30 to 40 µM lactam-1 was used, and by 5-fold when 50 µM lactam 1 is used (FIG. 5C). Levels of caspase-3 are increased by 2-, 3-, 5- and 11-fold when lactam 1 is used at 20, 30, 40 or 50 µM, respectively (FIG. 5C). Higher levels of caspase-9 activity were also detected in lysates of cells treated with higher concentrations of lactam 1, although caspase-9 activity levels were lower than those detected for caspase-8 and caspase-3 (FIG. 5C).

Both caspase activation and apoptosis induction were observed in time- and concentration-dependent fashions (FIGS. 3 and 5), indicating that caspases are required for lactam 1-induced apoptotic cell death. Jurkat T cells were pre-treated for 1 hour with an individual caspase inhibitor, a general caspase inhibitor (pan), or the vehicle (DMSO), followed by a co-treatment for 8 hours with 50 µM lactam 1. Pre- and co-incubation with each of the caspase inhibitors completely blocked lactam 1-induced PARP cleavage (FIG. 5D) and apoptosis-associated morphological changes (data not shown). Therefore, activation of the caspases is required for lactam 1-induced apoptosis.

EXAMPLE 4

Lactam 1-Induced Apoptosis is Associated with an Increased S Phase Population

It has been suggested that dysregulation of cell cycle progression is involved in the initiation of apoptosis (Lee S, Christakos S and Small M B, 1993, Apoptosis and signal transduction: clues to a molecular mechanism. *Curr Opin Cell Biol* 5:286-91; Dou Q P, 1997, Putative roles of retinoblastoma protein in apoptosis. *Apoptosis* 2:5-8; Smith D M, et al., 2000, Regulation of tumor cell apoptotic sensitivity during the cell cycle (Review). *Int J Mol Med* 6:503-7). The cell cycle distribution of Jurkat T cells that had been treated with lactam 1 is measured in the same kinetics (FIG. 3) and concentration-response (FIG. 5) experiments to determine whether lactam 1-induced apoptosis is associated with cell cycle-specific changes.

Figure 6A:
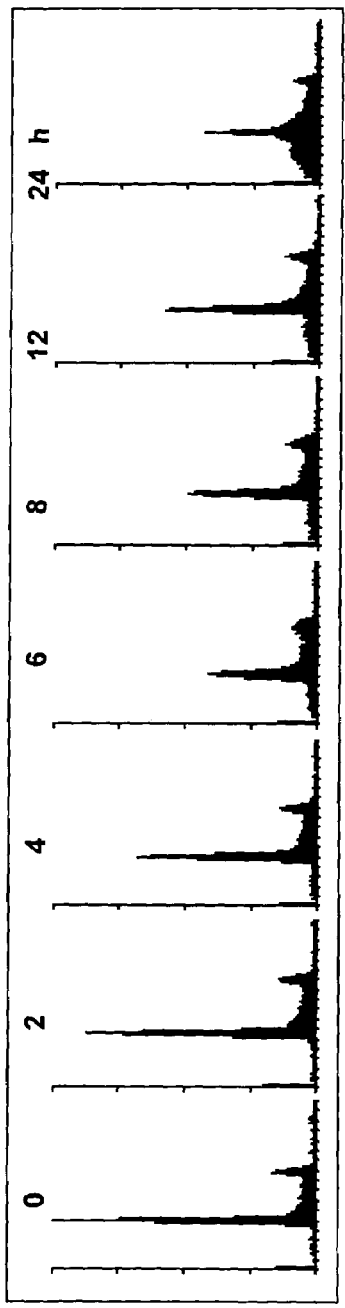
FIGS. 6A-B show that lactam 1 dysregulates cell cycle progression associated with apoptosis induction.

In the kinetics experiment, a slight decrease in $G_1$ and a corresponding increase in S phase population (2-3%) were observed after lactam 1 treatment for 2 to 4 hours (FIG. 6A). This was accompanied by induction of apoptotic cell death, as measured by increased apoptotic sub-$G_1$ (<$G_1$) cell population (2%; FIG. 6A) and PARP cleavage (FIG. 3A). After 6 to 12 hours treatment, S phase population was increased by up to 13%, while that of $G_1$ further decreased, without any apparent change in $G_2$/M population (FIG. 6A). Increased levels of sub-$G_1$ population (5-16%; FIG. 6A) and PARP cleavage (FIG. 3A) were also observed. A 24 hour treatment with lactam 1 further increased S (20%) and sub-$G_1$ (30%) populations (FIG. 6A). Concentration-response experiments (data not shown) provided further support that lactam 1-induced apoptosis is associated with increased S phase population.

Figure 2D:
Figure 6B:
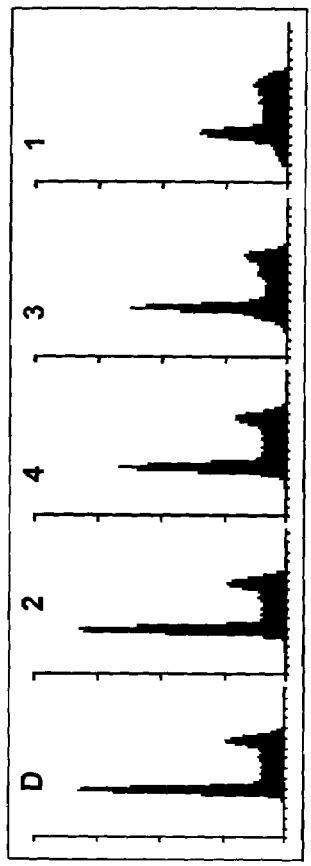

In screening apoptotically active β-lactams, it was found that compounds 2, 4, 3 and 1 increased cellular apoptosis in a stepwise fashion (FIG. 2). Whether these lactams also cause S phase accumulation in a similar manner was examined. Treatment of Jurkat T cells with 50 µM of lactam 2 for 5 hours did not induce accumulation of either S or sub-$G_1$ populations, similar to that of DMSO-treated cells (FIG. 6B, lactam 2 vs. D). In contrast, under the same conditions, treatment with lactams 4, 3 and 1 increased S phase population by 8%, 15% and 21%, respectively (FIG. 6B), associated with stepwise increases in sub-$G_1$ apoptotic populations of 2%, 10% and 14%, respectively (FIG. 6B). This data indicates that the number of carbons bound to the N-thio group is not only important for its apoptosis-inducing activity but also for its ability to arrest cells in S phase.

EXAMPLE 5

Lactam 1 Inhibits DNA Replication, Associated with Induction of DNA Damage

Figure 7A:
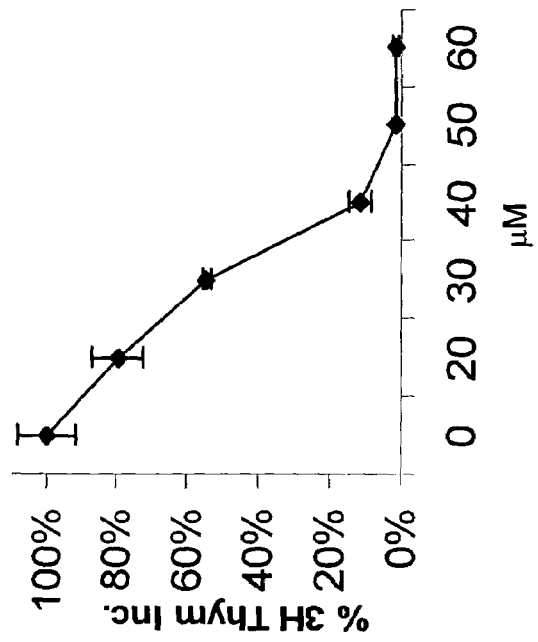
FIGS. 7A-E show that lactam 1 inhibits DNA replication and induces DNA strand breaks in Jurkat T cells.
Figure 7B:
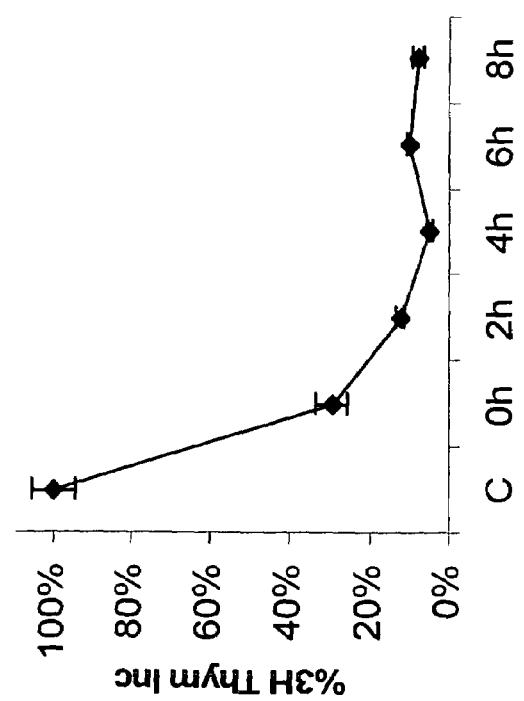

To determine whether the increased S phase population by lactam 1 is due to inhibition of DNA replication, a $^3$H-thymidine incorporation assay was performed with or without lactam 1 in both kinetics and concentration-response experiments. In the kinetics experiment, Jurkat T cells were pre-treated with 50 µM lactam 1 or DMSO for 0, 2, 4, 6 or 8 h, followed by a 2 hour co-treatment with $^3$H-thymidine. After that, cells were harvested and the amount of incorporated radioactive $^3$H-thymidine determined. When both lactam 1 and $^3$H-thymidine are added at the same time and then co-incubated for 2 h, incorporation of the $^3$H-thymidine was inhibited by ~70%, compared to the control cells (FIG. 7A, 0 h vs. C). A pre-incubation with lactam 1 for 2 to 8 h caused 95% inhibition of $^3$H-thymidine incorporation. Thus, lactam 1 inhibited $^3$H-thymidine incorporation, and did so immediately after its administration. The fact that lactam 1 inhibited $^3$H-thymidine incorporation within such a short time period (2 hours) indicates that lactam 1 is directly affecting the ability of the cell to replicate its DNA and this effect is not due to a change in cell cycle (see FIG. 6A).

In the concentration-response experiment, Jurkat T cells were pre-incubated for 2 h with various concentrations of lactam 1, followed by a 2 hour co-incubation with $^3$H-thymidine (a total treatment length of 4 h). Inhibition of $^3$H-thymidine incorporation was found to depend on lactam 1 concentrations used: 20% inhibition at 20 µM, 45% at 30 µM, 90% at 40 µM, and ~100% at 50 or 60 µM. The half-maximal inhibition value for incorporation of $^3$H-thymidine ($IC_{50}$) in intact Jurkat cells was determined to be 32 µM.

Figure 7C:
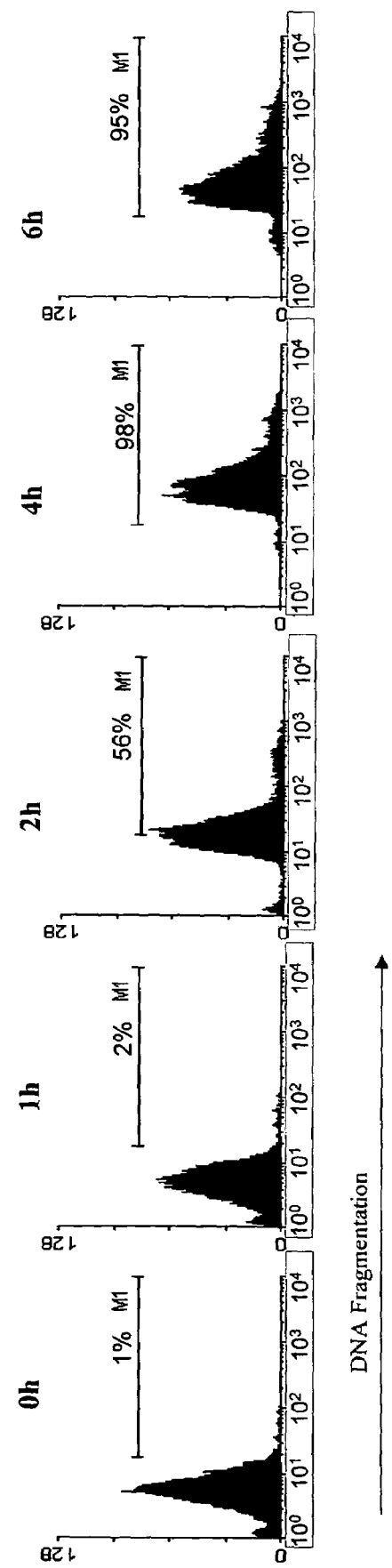
Figure 7D:
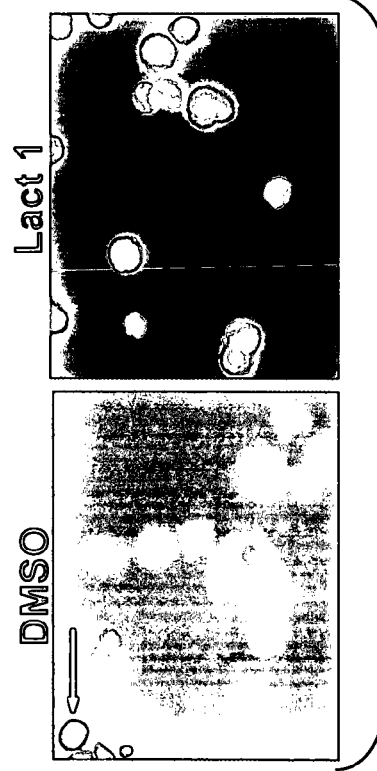
Figure 10:
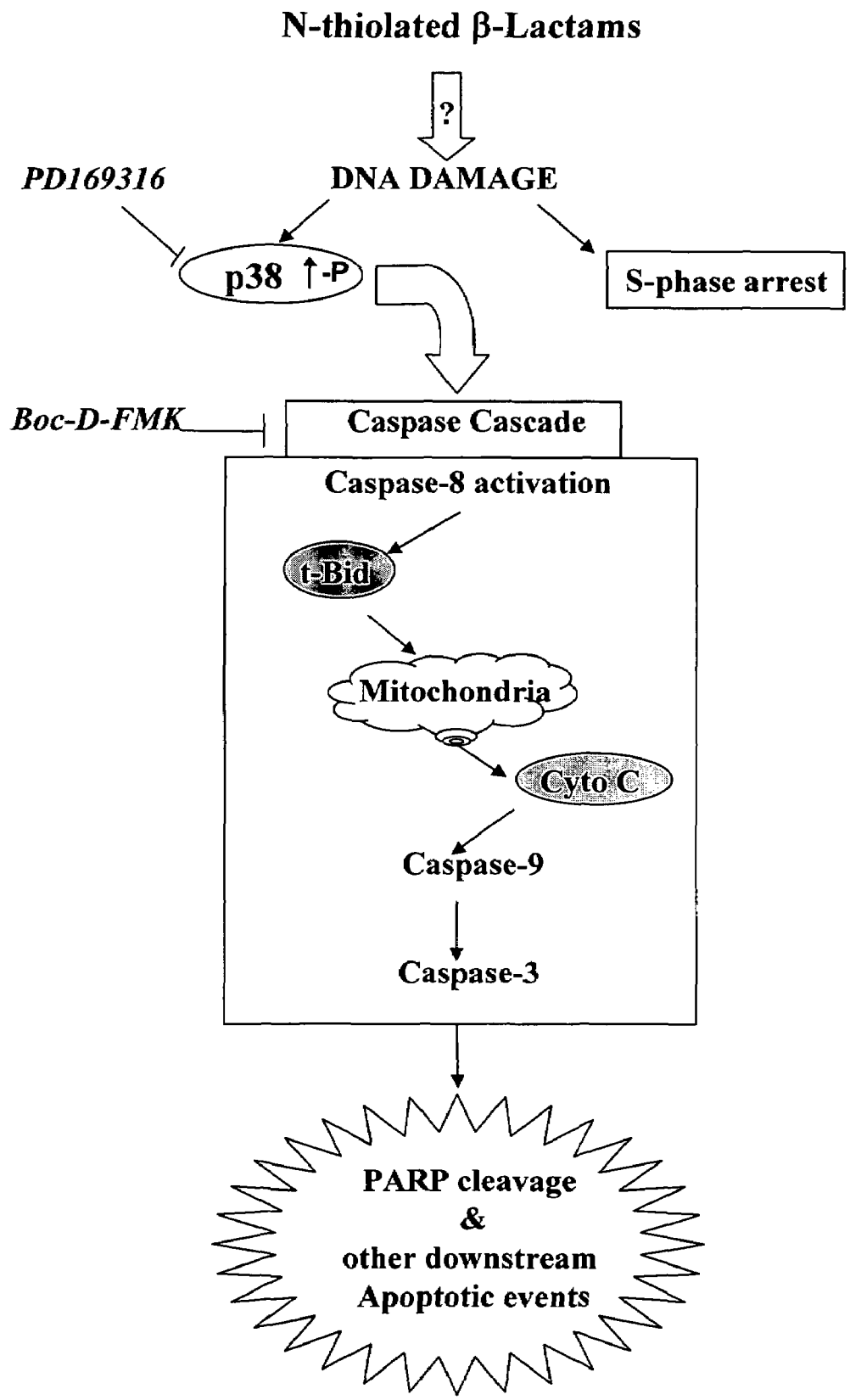
FIG. 10 shows the proposed order of apoptotic events induced by lactam 1. A cascade of events that occur during lactam 1-induced apoptosis is proposed based on kinetic and inhibitor studies.

To determine whether lactam 1 could induce DNA damage that would lead to the inhibition of DNA replication observed (FIGS. 7A and B), which would then be responsible for blockage of S phase progression (FIG. 6) and induction of apoptosis (FIGS. 1-6; also see FIG. 10), a TUNEL assay was implemented that detects DNA strand breaks, and the TUNEL-positive cells are either quantified by flow cytometry or observed under fluorescence microscopy. Treatment with lactam 1 for 1 hour did not induce DNA strand breaks, as compared to the untreated cells (0 h) that stained negative for nick-end labeling (FIG. 7C, 0 h vs. 1 h). However, after just 2 hour incubation with lactam 1, more than half of the cell population had shifted into the M1 region which demonstrated a positive signal for DNA strand breaks (FIG. 7C, 2 h). At this time, the S phase population is only slightly increased (compare FIG. 6A) and apoptosis had not been initiated (FIG. 3A). After a 4 hour treatment with lactam 1, almost the entire population of Jurkat cells contain damaged DNA, as shown by both flow cytometry (FIG. 7C) and fluorescence microscopy (FIG. 7D). Under the same conditions, the S population slightly increases (FIG. 6A) and apoptosis just starts to be detectable (FIG. 3A). These results suggest that lactam 1 induces DNA strand breaks prior to S phase accumulation and apoptosis induction. The fact that lactam 1 induces DNA damage in the entire cell population within 4 hours (FIGS. 7C and 7D) also indicates that it acts via a cell cycle-independent manner.

Figure 7E:
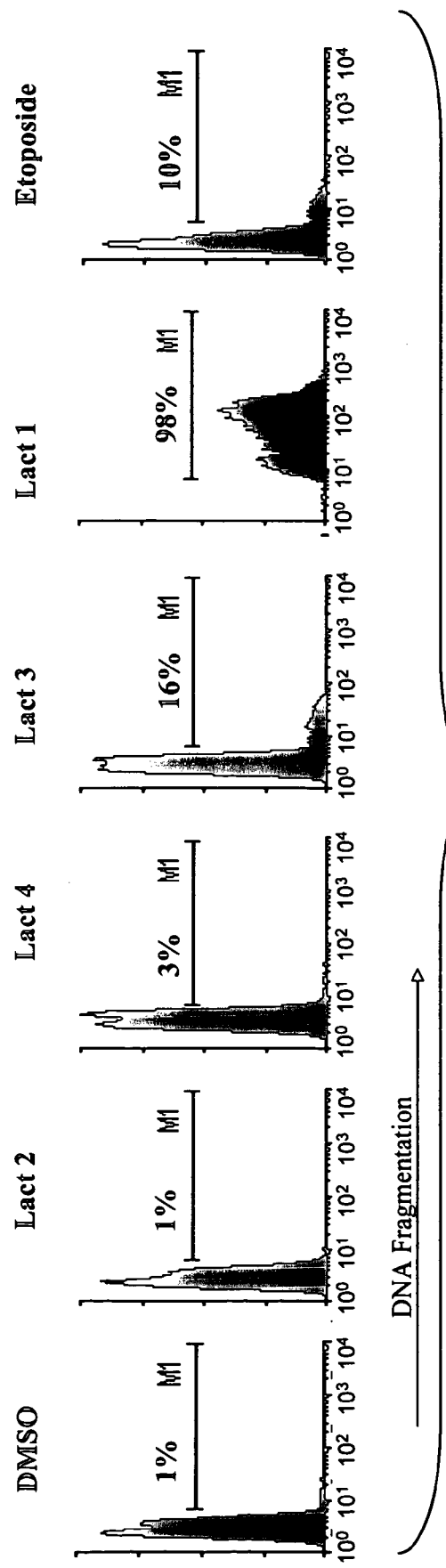

Lactams 2, 4, 3, and 1 were tested to see if the ability to induce apoptosis (FIGS. 13 and 18) and S phase accumulation (FIG. 6) matched that of their DNA-damaging abilities. After 4 hour treatment, DMSO or lactam 2 did not cause any DNA damage, while lactams 4 and 3 induced DNA damage in 3 and 16% of the cell population, respectively (FIG. 7E). Again, treatment with lactam 1 for 4 h causes nearly 100% of the treated cell population to become TUNEL-positive (FIG. 7E). As a comparison, the traditional DNA damaging agent etoposide (also referred to herein as VP-16) at the same concentration induced only 10% of the cells to become TUNEL-positive (FIG. 7E).

EXAMPLE 6

P38 Map Kinase Activation is Necessary for Lactam 1-Induced Apoptosis

It has been shown that multiple stimuli including DNA damaging agents induce apoptosis via activation of p38 MAP kinase (Kummer J L, et al., 1997, Apoptosis induced by withdrawal of trophic factors is mediated by p38 mitogen-activated protein kinase. *J. Biol Chem* 272:20490-4; Sanchez-Prieto R, et al., 2000, A role for the p38 mitogen-acitvated protein kinase pathway in the transcriptional activation of p53 on genotoxic stress by chemotherapeutic agents. *Cancer Res* 60:2464-72). Whether lactam 1 could activate p38 MAP kinase during apoptosis induction was examined, because lactam 1 is able to induce DNA strand breaks (FIGS. 7C and 7D). In this experiment, Jurkat T cells were treated with 50 µM lactam 1 for up to 12 hours, followed by measuring levels of phosphorylated (the activated form of p38 MAP kinase) and total p38 protein in Western blot assay. The levels of Tyr-182 phosphorylated p38 protein were increased by 3-fold at 2 h and reached its maximum (~9-fold) by 6 h (FIG. 8A). In has been shown that dual phosphorylation of p38 on Tyr-182 and Thr-180 activates this kinase (Raingeaud J, et al., 1995, Pro-inflammatory cytokines and environmental stress cause p38 mitogen-activated protein kinase activation by dual phosphorylation on tyrosine and threonine. *J Biol Chem* 270: 7420-6). In contrast, the levels of total p38 protein remained relatively unchanged (FIG. 8B). Therefore, lactam 1-induced DNA damage triggered activation of p38 before S population accumulation and apoptosis induction.

Lactam 4 showed a 2.6 fold normalized increase in phosphorylation of p38 over that of the control (FIG. 8D). Lactam 3 showed a further activation of p38 with a 3.2 fold induction over the control. Again, lactam 1 induced maximal p38 phosphorylation with a 5.9 fold increase (FIG. 8D).

To determine whether p38 activation is necessary for the apoptotic effects elicited by lactam 1, Jurkat T cells were pre-treated with either PD-169316, a specific p38 kinase inhibitor (Kummer et al., 1997), or the vehicle DMSO for 1 hour, followed by a co-treatment with lactam 1 for 8 hours. Pre- and co-treatment with PD-169316 completely inhibited the process of PARP cleavage induced by lactam 1, as compared to the control cells (FIG. 8E). In addition, PD-169316 potently inhibited lactam 1-induced activation of caspase-8, caspase-9 and caspase-3, as measured by cell-free caspase activity assay (FIG. 8F). In fact, the caspase-inhibitory effects of the p38 kinase inhibitor are comparable to those of the pan caspase inhibitor (FIG. 8F).

Whether PD169316 could potentially inhibit caspase activity directly was also investigated. Jurkat T cells were treated with 50 µM VP-16 for 5 hours, followed by preparation of cell lysates and measurement of cell-free caspase activities, in the absence or presence of PD169316 or the pan caspase inhibitor. The results show that PD169316 did not inhibit caspase-8, caspase-9 or caspase-3 activities in the VP-16-treated cell preparation. In contrast, the pan caspase inhibitor completely blocked the VP-16-induced caspase activities (data not shown). This result suggests that during lactam 1-induced apoptosis, p38 activation occurs upstream of caspase activation and is necessary for caspase-mediated cell death.

Given that lactam 1 is able to inhibit DNA replication (FIG. 7) and induce apoptosis (FIGS. 1-6) and that lactam 1-induced apoptosis can be blocked by PD-169316 (FIGS. 8E and 8F), the ability of the p38 inhibitor to affect the DNA replication-inhibitory activity of lactam 1 was studied. An $^3$H-thymidine incorporation assay was performed using Jurkat cells treated with lactam 1 alone or a combination of lactam 1 and PD-169316. Inhibition of DNA replication by lactam 1 was not affected by addition of PD-169316 (FIG. 8G). Thus, the p38 kinase inhibitor inhibited the lactam 1-induced downstream apoptotic events, but did not affect the ability of lactam 1 to inhibit DNA replication.

To further investigate the order of lactam 1-induced apoptotic events, effects of PD-169316 and the pan caspase inhibitor Boc-D-FMK on TUNEL positivity and p38 phosphorylation were measured. In this experiment, growing Jurkat T cells (control) were treated for 4 hours with lactam 1 in the absence (with DMSO) or presence of PD169316 or Boc-D-FMK, followed by measurement of TUNEL-positive cells and phosphorylated p38 levels. Again, Lactam 1 treatment induced 96% TUNNEL positivity. Similarly, cells that had been co-treated with lactam 1 and PD169316 or Boc-D-FMK, show 95% and 97% TUNNEL positivity, respectively (FIG. 8H), demonstrating that neither the p38 inhibitor nor the pan caspase inhibitor could block DNA strand breaks induced by lactam 1. This data also suggests that DNA damage must lie upstream of p38 and caspase activation. In addition, lactam 1-induced p38 phosphorylation was not affected by Boc-D-FMK (FIG. 8I), supporting the conclusion that p38 activation occurs upstream of caspase activation (compare to FIG. 8F).

EXAMPLE 7

Lactam 1 Inhibits Cell Proliferation and Induces Apoptosis in Several Solid Tumor Cell Lines The effects of lactam 1 on several other human solid tumor cell lines are studied. Exponentially grown (0 hour) human breast (MCF-7, MDA-MB-231), prostate (PC-3), and head-and-neck (PCI-13) cancer cell lines were treated with either 50 µM lactam 1 or DMSO for 24 hours, followed by performance of an MTT assay which measures the status of cell viability and thus cell proliferation. The DMSO-treated cells continued to proliferate after 24 hours (FIG. 9A). However, after treatment with lactam 1, cellular viability of MCF-7 cells, MDA-MB-231 cells and PCI-13 cells decreased by 80% and that of PC-3 cells decreased by 60% (FIG. 9A).

To determine whether lactam 1-mediated growth inhibition is due to cell death, these tumor cell lines were treated with 50 µM lactam 1 or an equal percentage of DMSO, followed by separation of the attached and detached cell populations. Both attached and detached cell populations were then used for detection of apoptotic nuclear changes. After a 24 hour treatment with lactam 1, ~50% of MCF-7 cells became detached. All the detached MCF-7 cells exhibited typical apoptotic nuclear condensation and fragmentation (FIG. 9B). The cellular detachment is most likely triggered by apoptosis induction, because the remaining attached MCF-7 cells also show apoptotic nuclear morphology (FIG. 9B). Little or no detachment was observed in MCF-7 cells treated with DMSO; consistent with that, all the remaining attached cells contain normal, round nuclei (FIG. 9B). Similar to MCF-7 cells, about half of MDA-MB-231, PC-3 and PCI-13 cells become detached after a 48 hour treatment with lactam 1 but not DMSO. Almost all the detached cells exhibited an apoptosis-specific nuclear morphology (FIG. 9B). These data demonstrate that lactam 1 is able to inhibit cell proliferation and induce cell death in these breast, prostate, and head and neck solid tumor cell lines.

Materials and Methods for Examples 8-12

Materials.

Fetal bovine serum (Tissue Culture Biologicals, Tulane, Calif.), 3-(4,5-dimethylthiazol-2-yl)-2,5-diphenyltetrazolium bromide (MTT), Dimethyl sulfoxide (DMSO) and trypan blue were purchased from Sigma-Aldrich (St. Louis, Mo.). RPMI 1640, Dulbecco's modified Eagle's medium (DMEM), MEM non-essential amino acids solution, MEM sodium pyruvate solution, penicillin, and streptomycin were purchased from Invitrogen (Carlsbad, Calif.). Polyclonal antibody to human PARP was obtained from Roche Molecular Biochemicals (Indianapolis, Ind.). The APO-DIRECT kit for terminal deoxynucleotidyl transferase-mediated UTP nick-end labeling (TUNEL) staining was purchased from BD Pharmingen (San Diego, Calif.).

Synthesis of β-Lactams.

The β-lactam analogs (FIG. 13) were prepared as racemates (with cis stereochemistry) using a procedure described previously (Ren X F, et al., 1998, Studies on nonconventionally fused bicyclic beta-lactams. *J Organic Chem* 63:8898-17; Turos E, Konaklieva M I, Ren R X F, Shi H, Gonzalez J, Dickey S, Lim D V., 2000, N-thiolated bicyclic and monocyclic beta-lactams. *Tetrahedron* 56:5571-78).

Cell Culture, Protein Extraction, and Western Blot Assay.

Human Jurkat T cells and human prostate cancer LNCaP cells were cultured in RPMI 1640 medium, supplemented with 10% fetal bovine serum, 100 units/ml penicillin, and 100 μg/ml streptomycin. Human YT cells were cultured in RPMI 1640 medium supplemented with 1 mM MEM sodium pyruvate solution, 0.1 mM MEM non-essential amino acids solution, 10% fetal bovine serum, 100 units/ml penicillin, and 100 μg/ml streptomycin. All cell lines were maintained at 37° C. in a humidified incubator with an atmosphere of 5% $CO_2$. A whole-cell extract was prepared as described previously (An B, Goldfarb R H, Siman R, Dou Q P., 1998, Novel dipeptidyl proteasome inhibitors overcome Bcl-2 protective function and selectively accumulate the cyclin-dependent kinase inhibitor p27 and induce apoptosis in transformed, but not normal, human fibroblasts. *Cell Death Differ* 5:1062-75). Briefly, cells were harvested, washed with PBS and homogenized in a lysis buffer (50 mM Tris-HCl, pH 8.0, 5 mM EDTA, 150 mM NaCl, 0.5% NP-40, 0.5 mM phenylmethylsulfonyl fluoride, and 0.5 mM dithiothreitol) for 30 min at 4° C. Afterwards, the lysates were centrifuged at 12000×g for 15 min at 4° C. and the supernatants collected as whole-cell extracts. Equal amounts of protein extract (60 μg) were resolved by SDS-polyacrylamide gel electrophoresis and transferred to a nitrocellulose membrane (Schleicher & Schuell, Keene, N. H.) using a Semi-Dry Transfer System (Bio-Rad, Hercules, Calif.). The enhanced chemiluminescence Western blot analysis was then performed using specific antibodies to the proteins of interest.

Trypan Blue Assay.

The trypan blue dye exclusion assay was performed by mixing 20 μl of cell suspension with 20 μl of 0.4% trypan blue dye before injecting into a hemocytometer and counting. The number of cells that absorbed the dye and those that exclude the dye were counted, from which the percentage of nonviable cell number to total cell number was calculated.

Morphological Assessment of Apoptosis.

To assess morphological changes of cells, 50 μl of treated or untreated cell suspension were transferred to a glass slide at the indicated time points. The slides were observed under a phase-contrast microscope (Leica; Wetzlar, Germany) and photographs were taken (100×). Apoptotic cells were identified by their distinct morphological changes.

TUNEL Assay.

Terminal deoxynucleotidyl transferase-mediated nick end labeling (TUNEL) was used to determine the extent of DNA strand breaks (Smith D M, Dou Q P., 2001, Green tea polyphenol epigallocatechin inhibits DNA replication and consequently induces leukemia cell apoptosis. *Int J Mol Med* 7:645-52). The assay was performed following manufacturer's instruction using the APO-Direct kit. In brief, the harvested cells were fixed in 1% paraformaldehyde for 15 min on ice, washed with PBS, and then fixed again in 70% ethanol at −20° C. overnight. The cells were then incubated in DNA labeling solution (containing terminal deoxynucleotidyl transferase (TdT) enzyme, fluorescein-conjugated dUTP and reaction buffer) for 90 min at 37° C. After removing the DNA labeling solution by rinsing cells with Rinsing Buffer, the cells were incubated with the Propidium Iodide/RNase A solution, incubated for 30 min at room temperature in the dark, and then analyzed by flow cytometry within 3 h of staining.

Caspase-3 Activity Assay.

To measure cell-free caspase-3 activity, whole cell extracts (20-30 μg) from untreated or treated LNCaP cells were incubated with 20 μM of the fluorogenic substrate caspase-3/caspase-7 (Ac-DEVD-AMC) for 30 min at 37° C. in 100 μl of assay buffer (50 mM Tris, pH 8.0). Measurement of the hydrolyzed AMC groups was performed on a VersaFluor™ Fluorometer (Bio-Rad) as described previously (Nam S, Smith D M, Dou Q P., 2001, Ester bond-containing tea polyphenols potently inhibit proteasome activity in vitro and in vivo. *J Biol Chem* 276:13322-30).

Soft Agar Assay.

The soft agar assay was performed as described previously (Menter D G, Sabichi A L, Lippman S M., 2000, Selenium effects on prostate cell growth. *Cancer Epidemiol Biomarkers Prev* 9:1171-82) with a few modifications. In brief, in a six-well plate, a bottom feeder layer (0.6% agar) was prepared with DMEM media containing 10% fetal bovine serum, 100 units/ml penicillin, and 100 μg/ml streptomycin. A top layer (0.3% agar) was prepared with DMEM and the same media as described above but containing $2 \times 10^4$ prostate cancer LNCaP cells and 50 μM of lactam 1 or lactam 12, or equal volume of solvent (DMSO) as a control. Plates were incubated at 37° C. in 5% $CO_2$ in a humidified incubator for three weeks. MTT (1 mg/ml) was added to each well and incubated overnight to allow complete formation of purple formazan crystals. The plates were then scanned and photographed, and the number of colonies was quantified by Quantity one v.4.0.3 software (Bio-Rad, Hercules, Calif.).

EXAMPLE 8

Screening for More Apoptotically Active Analogs of lactam 1

Figure 13A:
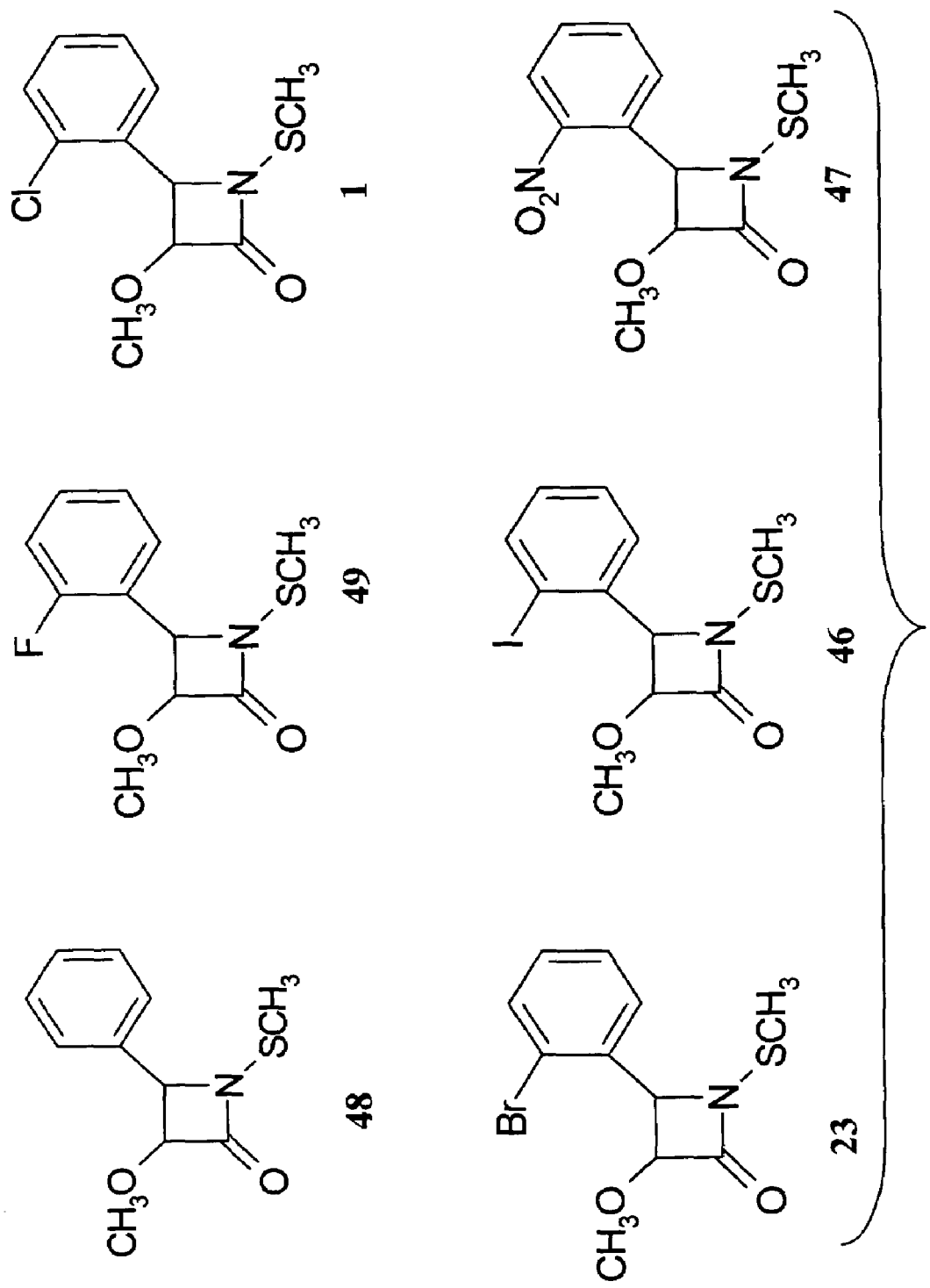
FIGS. 13A-B show a screen for more potent analogs of the lactam 1.
Figure 13B:
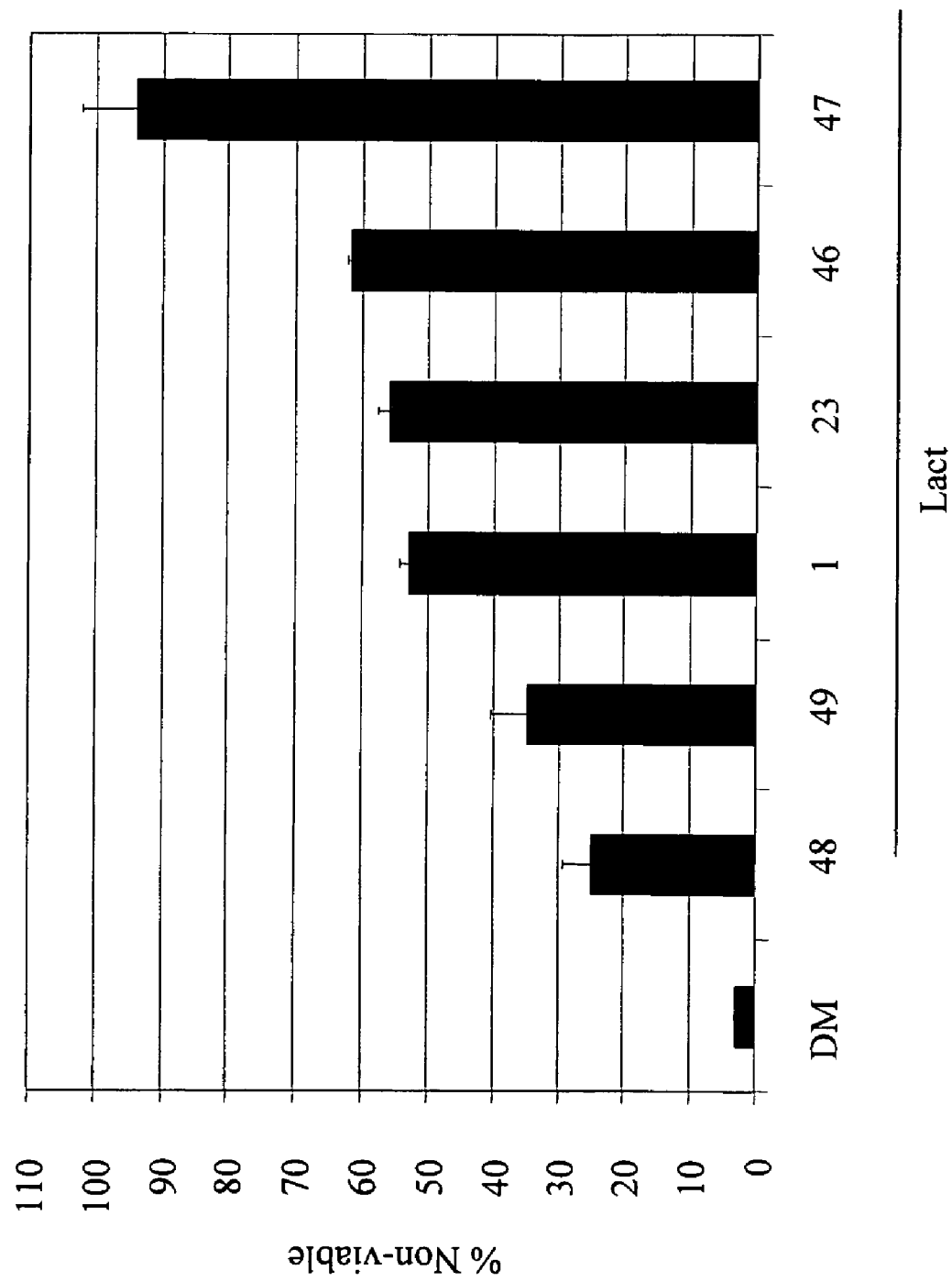

Lactam 1 contains a chloro (Cl) group in the ortho position on the benzene ring (FIG. 13A). To examine whether deletion or substitution of the Cl group could affect lactam 1 cell death-inducing ability, additional halogen (lactams 23, 46, and 49) and nonhalogen (lactam 47) analogs of lactam 1 were synthesized (FIG. 13A). These compounds were then tested in the trypan blue dye exclusion assay, using lactam 1 as a comparison (FIG. 13B). Jurkat T cells were treated with each of these compounds at 50 μM for 24 h, followed by measurement of loss of cell membrane permeability, indicative of a late apoptotic stage (FIG. 13B) (Wyllie A H, Kerr J F, Currie A R., 1980, Cell death: the significance of apoptosis. *Int Rev Cytol* 68:251-306; Earnshaw W C., 1995, Nuclear changes in apoptosis. *Curr Opin Cell Biol* 7:337-43). As a control, lactam 1 induced ~52% cell death (FIG. 13B). Interestingly, removal of the Cl group from the benzene ring significantly decreased the cell death-inducing activity to ~25% (lactam 48; FIG. 13B). Furthermore, replacement of the Cl group with a smaller halogen atom (—F; lactam 49) also decreased the death-inducing activity (to ~35%), while analogs with a larger halogen group (—Br and —I; lactams 23 and 46, respectively; FIG. 13A) increased the cell death rates to 55 and 60% (FIG. 13B). These data indicate that the size of the group in the ortho position on the benzene ring is important for the compound's cell death-inducing activity. The analog with the —NO$_2$ group in the ortho position of the benzene ring, lactam 47 (FIG. 13A), exhibited the strongest effect with a total of ~94% cell death (FIG. 13B). Therefore, the order of potency of the tested compounds was: H<F<Cl<Br<I<NO$_2$.

EXAMPLE 9

Lactam 1 Induces Apoptosis Preferentially in Leukemic Jurkat T Over Non-Transformed Immortalized NK Cells To determine whether lactam 1 was able to induce apoptosis preferentially in tumor/transformed vs. normal/non-transformed cells, human leukemic Jurkat T cells and immortalized, non-transformed NK cells (YT line) (Drexler H G, Matsuo A Y, MacLeod R A., 2000, Continuous hematopoietic cell lines as model systems for leukemia-lymphoma research. *Leuk Res* 24:881-911) were treated with lactam 1 in both concentration- and time-dependent experiments. Treatment of Jurkat T cells with 10 μM of lactam 1 for 24 h induced apoptosis-specific PARP cleavage fragment p85 (FIG. 14A), whose levels were further increased when 25 μM of lactam 1 was used (FIG. 14A). After treatment with 50 μM of lactam 1, PARP degradation was further increased, as evidenced by a significant decrease in expression of intact PARP protein (FIG. 14A). In contrast, no PARP cleavage was detectable in the YT cells after treatment with lactam 1 at even 50 μM (FIG. 14A).

In the kinetic experiment, both Jurkat T cells and YT cells were treated with 30 μM of lactam 1 for 3, 6, or 24 h. Again, PARP cleavage was detected in Jurkat T cells first at 3 h, which was then increased at 6 h (FIG. 14B). By 24 h, the levels of PARP/p85 fragments in Jurkat T cells were decreased, probably again due to further degradation (FIG. 14B). Importantly, no PARP cleavage was observed in YT cells in the same kinetics experiment (FIG. 14B). To confirm the tumor cell-selective killing activity of lactam 1, a trypan blue dye exclusion assay was performed in the same kinetic experiment. After 24 h, there was 42% cell death in the Jurkat T cells compared to 9% in YT cells (FIG. 14C). Furthermore, by using phase-contrast microscopy, more cell death was observed in Jurkat T cells than YT cells (FIG. 14D). Thus, lactam 1 induced apoptotic cell death selectively in tumor cells over non-transformed cells.

EXAMPLE 10

Figure 15A:
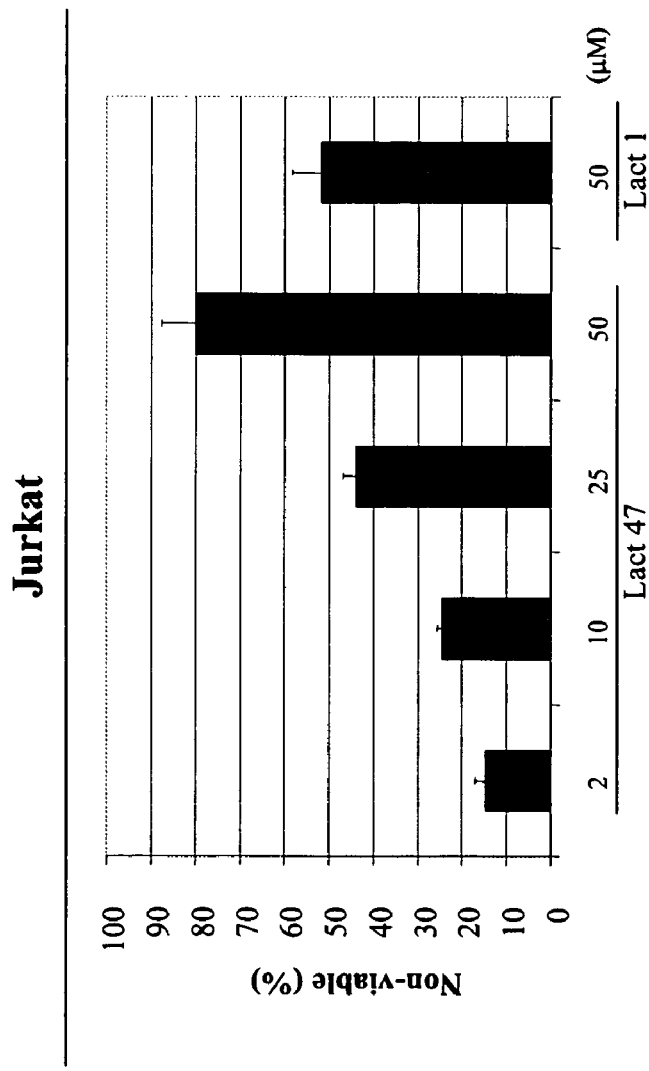
FIGS. 15A-D show dose-response comparison between Jurkat T and YT cells treated with lactam 12 and lactam 1 to induce cell apoptosis. Jurkat T (FIGS. 15A and 15B) and YT cells (FIGS. 15C and 15D) were treated with 2, 10, 25, and 50 μM of lactam 12 versus 50 μM of lactam 1 for either 12 (FIGS. 15B and 15D) or 24 h (FIGS. 15A and 15C), followed by trypan blue exclusion (FIGS. 15A and 15C) or Western blot assay using anti-PARP antibody (FIGS. 15B and 15D). Results are representative of three different experiments. Standard deviations are shown with error bars from a mean of at least three independent experiments (FIGS. 15A and 15C).
Figure 15B:

Lactam 47 Has Enhanced Apoptosis-Inducing Activity Specific to Jurkat T, but not Normal YT Cells To determine if lactam 47 is capable of inducing apoptosis at lower concentrations than lactam 1, a dose-response experiment was performed with both compounds. Jurkat T cells were treated with lactam 47 at 2, 10, 25, and 50 μM for 24 h, using 50 μM of lactam 1 as a comparison. Again, treatment with lactam 1 caused ~50% cell death, measured by trypan blue exclusion assay (FIG. 15A). Under the same experimental conditions, lactam 47 induced cell death in a concentration-dependent-manner: 25% cell death at 10 μM, 45% at 25 μM, and 80-90% at 50 μM (FIG. 15A). Therefore, lactam 47 is ~2-fold more potent than lactam 1. This conclusion was further supported by PARP cleavage assay using lysates prepared after 12 h treatment (FIG. 15B). Cleavage of PARP occurred in lactam 47-treated cells in a dose-dependent manner with the highest level of PARP cleavage observed at 50 μM (FIG. 15B). The levels of PARP cleavage induced by 50 μM of lactam 1 were equivalent to ~50% of that by 50 μM of lactam 47 (FIG. 15B).

Figure 15C:
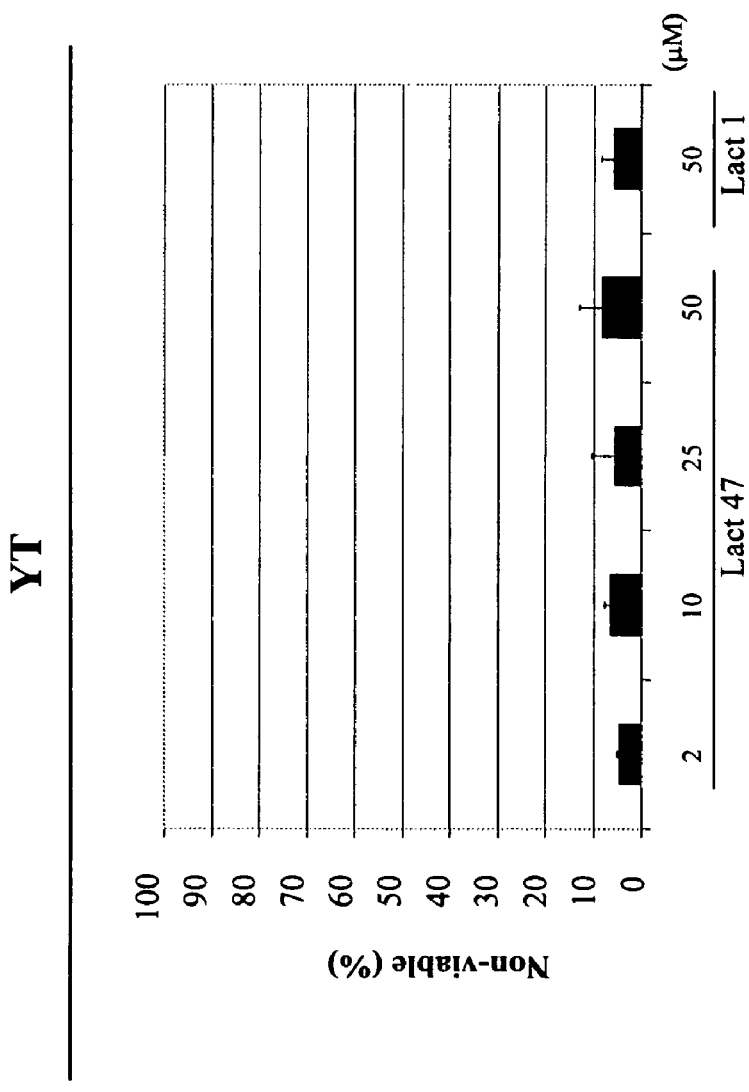
Figure 15D:
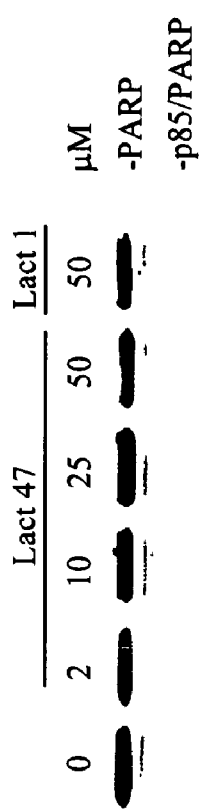

In the same experiment, when immortalized, non-transformed NK cells were treated with lactam 47 (using lactam 1 as a control), neither cell death (FIG. 15C) nor PARP cleavage (FIG. 15D) were observed. Therefore, like lactam 1, lactam 47 also induced apoptotic cell death preferentially in tumor cells over non-transformed cells.

Figure 16A:
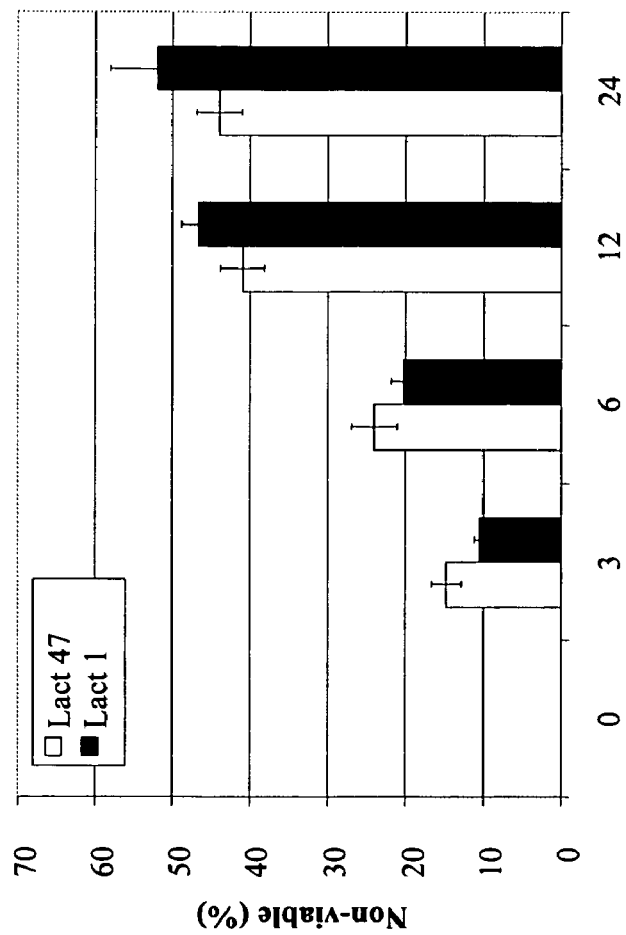
FIGS. 16A-B show a kinetic comparison between lactam 12 and lactam 1 to induce apoptosis in Jurkat T cells. Jurkat T cells were treated with 25 μM of lactam 12 versus 50 μM of lactam 1 for 3, 6, 12, and 24 h, followed by trypan blue dye exclusion assay (FIG. 16A), and PARP cleavage in Western blot assay (FIG. 16B). Results are representative of three different experiments. Standard deviations are shown with error bars from a mean of at least three independent experiments.
Figure 16B:
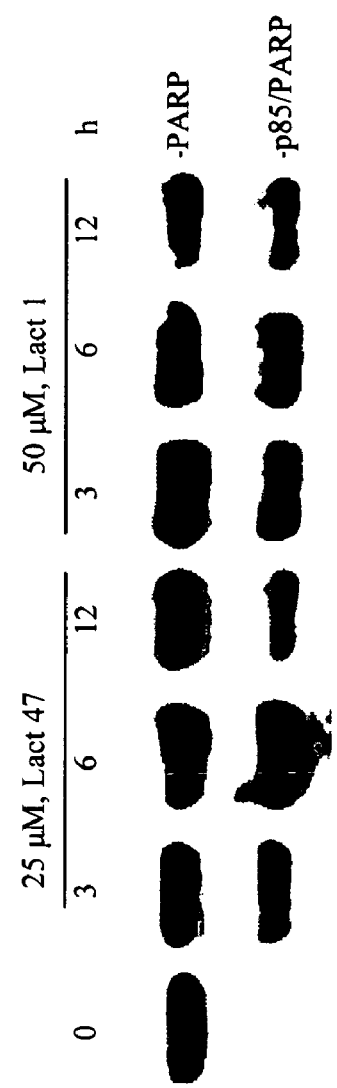

To further compare the potency of lactams 1 and 47, Jurkat T cells were treated with 25 μM of lactam 47 versus 50 μM of lactam 1 for 3, 6, 12, and 24 h, followed by determination of trypan blue incorporation and PARP cleavage. After 3 h, lactam 47 at 25 μM caused 15% versus 11% cell death with lactam 1 at 50 μM (FIG. 16A). Similarly, at 6 h, 24% of trypan blue-positive cells were found after 25 μM lactam 47 treatment, while only 20% observed in 50 μM lactam 1-treated cells (FIG. 16A). Only at later time points (12 and 24 h), lactam 1 at 50 μM was slightly more potent than lactam 47 at 25 μM (FIG. 16A). Similar levels of cleaved PARP were observed in Jurkat T cells treated with either 25 μM of lactam 47 or 50 μM of lactam 1 at each time point (FIG. 16B). Therefore, lactam 47 is able to induce similar amounts of apoptosis in Jurkat T cells at a concentration half of that of lactam 1.

Figure 17A:
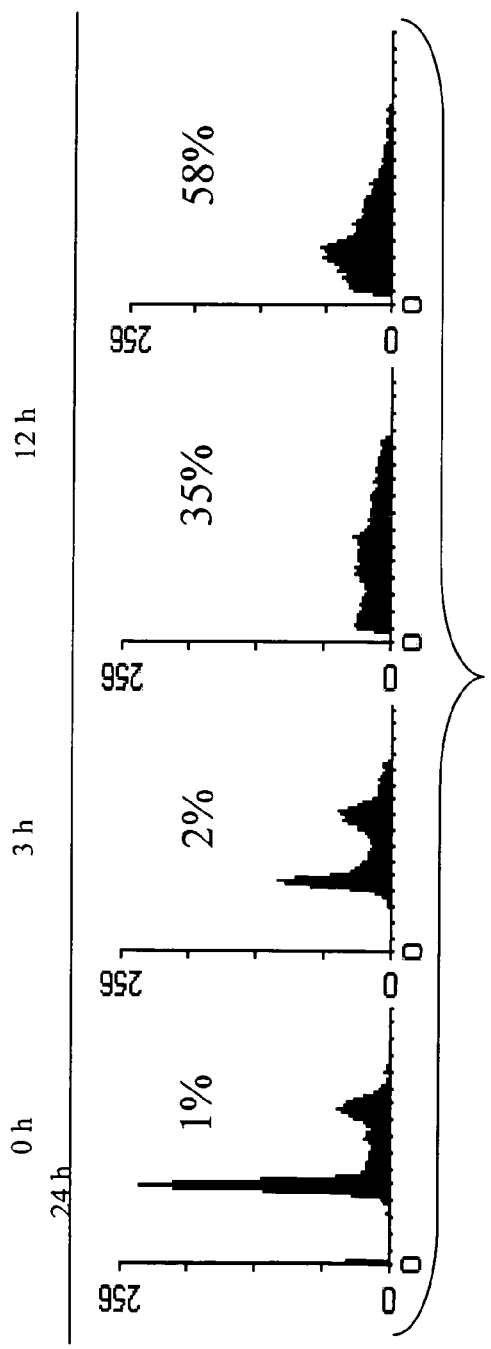
FIGS. 17A-B show lactam 12 induces sub-$G_1$ cell population and TUNEL-positivity. Jurkat T cells (0 h) were treated with 50 μM of lactam 12 for the indicated hours.

Levels of sub-G$_1$ populations, as a measurement of cells with DNA fragmentation (An B, Goldfarb R H, Siman R, Dou Q P., 1998, Novel dipeptidyl proteasome inhibitors overcome Bcl-2 protective function and selectively accumulate the cyclin-dependent kinase inhibitor p27 and induce apoptosis in transformed, but not normal, human fibroblasts. *Cell Death Differ* 5:1062-75), were examined in Jurkat T cells treated with lactam 47 or lactam 1. Treatment with 50 μM of lactam 47 increased the sub-G$_1$ populations by 34 and 57%, respectively, at 12 and 24 h (FIG. 17A). In comparison, 50 μM of lactam 1 treatment for 12 and 24 h induced sub-$G_1$ populations by 10 and 16%, respectively (Smith D M, Kazi A, Smith L, Long T E, Heldreth B, Turos, E, Dou Q P., 2002, A novel beta-lactam antibiotic activates tumor cell apoptotic program by inducing DNA damage. *Mol Pharmacol* 61:1348-58), confirming the greater potency of lactam 47.

EXAMPLE 11

Lactam 47 is Able to Induce DNA-Damage in Jurkat T Cells

Figure 17B:
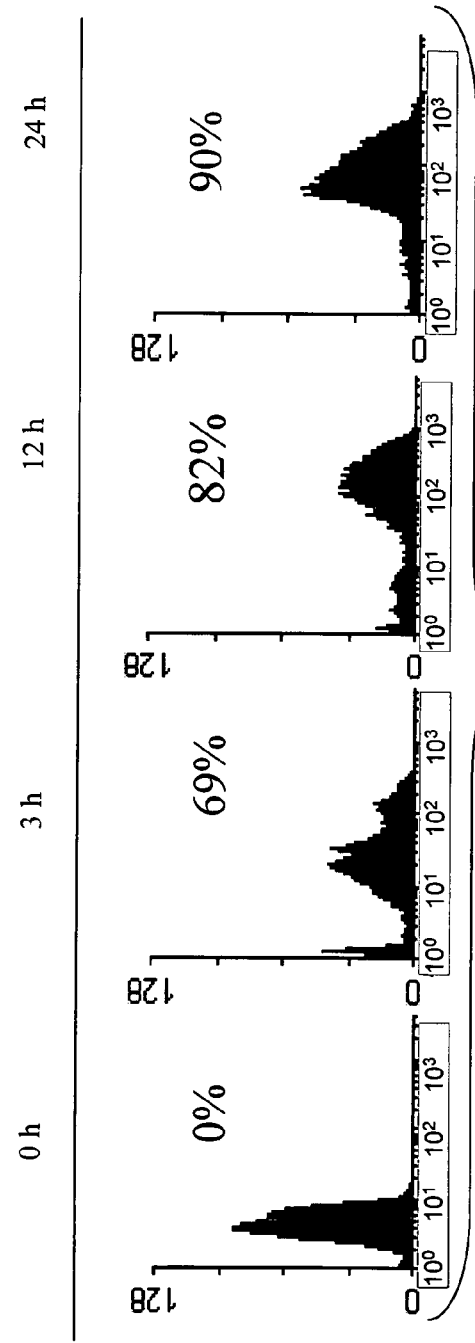

Jurkat T cells were treated with 50 µM of lactam 47, followed by performance of TUNEL assay, which detects DNA strand breaks (Smith D M, Kazi A, Smith L, Long T E, Heldreth B, Turos, E, Dou Q P., 2002, A novel beta-lactam antibiotic activates tumor cell apoptotic program by inducing DNA damage. *Mol Pharmacol* 61:1348-58). A significant population (~70%) of the cells exhibited DNA strand breaks after 3 h of incubation with lactam 47 (FIG. 17B). A total of 82-90% of the cells were TUNEL-positive after 12-24 h treatment with lactam 47 (FIG. 17B). In this experiment, 66% of TUNEL-positive cells were observed after treatment with 50 µM of lactam 1 for 24 h (data not shown). Thus, the increased DNA-damaging capability of lactam 47 is most likely responsible for its enhanced cell death-inducing activity (FIGS. 13-16).

EXAMPLE 12

Lactams 1 and 47 Induces Apoptosis and Inhibit Colony Formation in Human Prostate Cancer Cells To determine if lactam 1 and lactam 47 could also activate death program in solid tumor cells, human prostate cancer LnCaP cells were treated for 48 h with lactam 47 at 2-25 µM or lactam 1 at 50 µM, followed by measurement of cell-free caspase-3 activity. A dose-dependent increase in caspase-3 induction was observed in LNCaP cells treated with lactam 47: by 2-, 2.5- and 4.2-fold, respectively, at 2, 10 and 25 µM (FIG. 18A). Treatment with 50 µM of lactam 1 also increased levels of caspase-3 activity by 2.5-fold over the control (FIG. 18A). These data are consistent with the conclusion that lactam 47 has greater apoptosis-inducing potency than lactam 1.

The in vivo effects of lactam 1 and lactam 47 in a soft agar assay that measures the transforming activity of human tumor cells was investigated. LNCaP cells were plated in soft agar along with 50 µM of lactam 1, 50 µM of lactam 47, or solvent (DMSO), followed by a 21 day-incubation to allow for colony formation. The solvent (DMSO)-treated plates allowed for the development of ~500 colonies (FIGS. 18A and 18B). Lactam 1 inhibited 91%, and lactam 47 completely blocked (~100%), colony formation of LNCaP cells (FIGS. 18A and 18B). Therefore, both lactams are able to inhibit the transformation capability of prostate cancer cells.

EXAMPLE 13

Lactam 1 Selectively Inhibits Proliferation and Induces Apoptosis in Transformed but not Normal WI-38 Cells A normal human fibroblast cell line (WI-38) and its SV40-transformed derivative (VA-13) were tested to determine if lactam 1 could selectively induce cell death in tumor cells versus normal cells. An MTT assay was performed in a 96-well plate, which measures cellular mitochondrial function and thereby cytotoxicity. Treatment with 50 µM lactam 1 for 6 or 24 hours completely inhibited growth of the transformed VA-13 cells, compared to the same cells untreated (0 hour) or treated with DMSO (FIG. 19A). In contrast, the normal WI-38 cells continued to grow even after 24 hours treatment with 50 µM lactam 1, although such a treatment slightly inhibited the cell growth, compared to the DMSO-treated WI-38 cells (FIG. 19A). By 120 hours, no viable VA-13 cells are found, whereas the population of WI-38 cells is doubled (data not shown).

To investigate whether selective inhibition of cell proliferation by lactam 1 is related to selective induction of apoptosis in the transformed vs. normal WI-38 cells, caspase activation and apoptosis were measured. Treatment of VA-13 cells with lactam 1 for up to 48 hours activated cell-free caspase-9 activity (FIG. 19B). However, no caspase-9 activation was detected in normal WI-38 cells under the same treatment (FIG. 19B). Similarly, processing and thereby activation of caspase-3 was detected only in the transformed, but not normal, human cells (FIG. 19C).

Figure 19D:
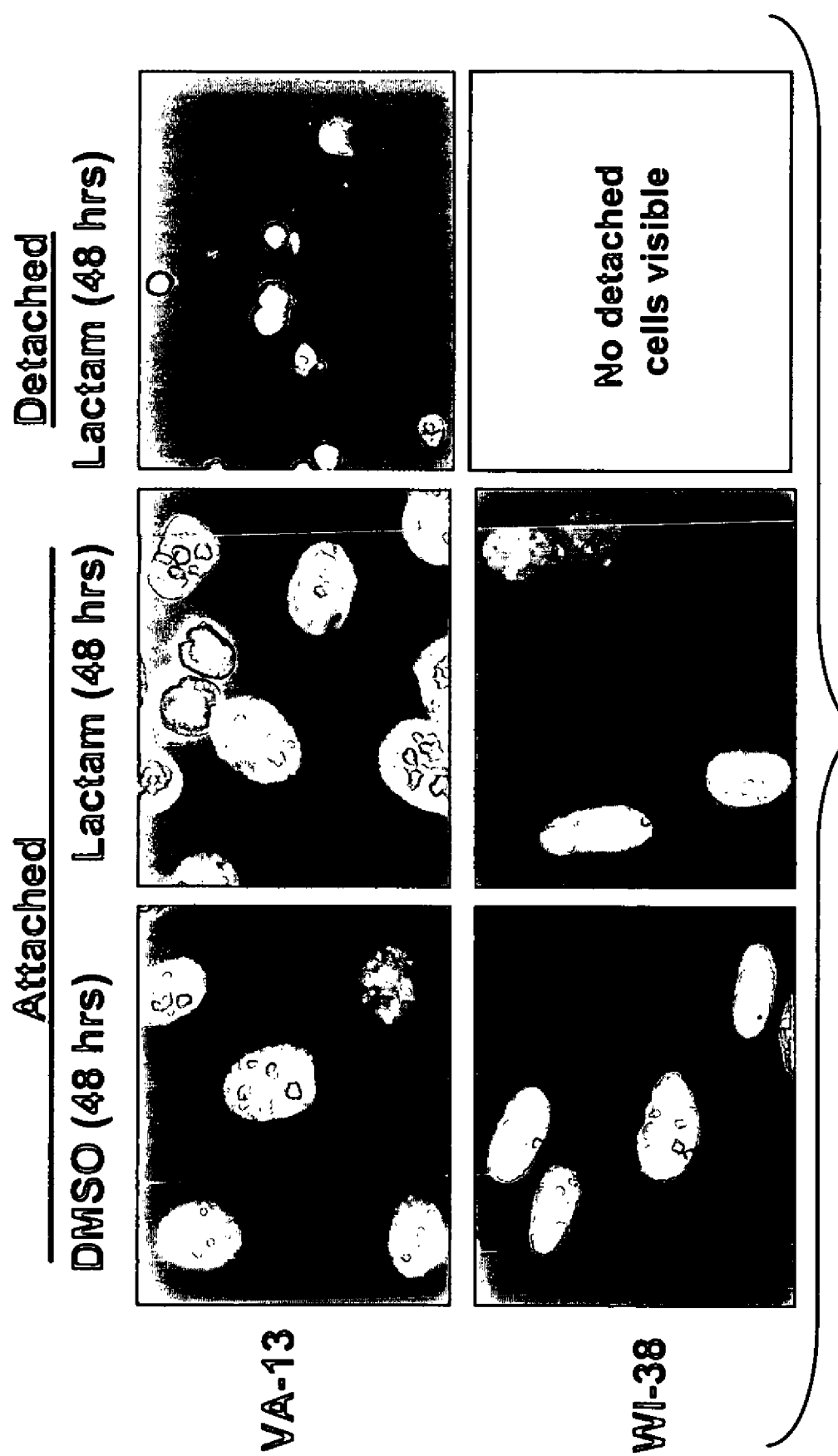

Consistent with selective activation of caspases, detachment was found only in VA-13, but not WI-38 cells, after lactam 1 treatment; the detached VA-13 cells revealed apoptotic nuclear condensation and fragmentation (FIG. 19D). Even the remaining attached VA-13 cells showed apoptotic nuclear morphology (FIG. 19D), indicating that apoptosis triggered detachment. In contrast, the treated WI-38 cells remained attached with normal nuclei (FIG. 19D). These results suggest that lactam 1 is able to selectively activate caspases and induce apoptosis in the transformed cells versus normal cells.

It should be understood that the examples and embodiments described herein are for illustrative purposes only and that various modifications or changes in light thereof will be suggested to persons skilled in the art and are to be included within the spirit and purview of this application.

We claim:

1. A method for inducing a cellular event selected from the group consisting of cell death, caspase cascade activation, mitochondrial cytochrome C release into cytoplasm, damage to DNA of a cell, and p38 MAP kinase activation, or for inhibiting an event selected from the group consisting of cell proliferation and DNA replication, said method comprising contacting or exposing a cell to an N-thiolated β-lactam compound having the structure of Formula A,

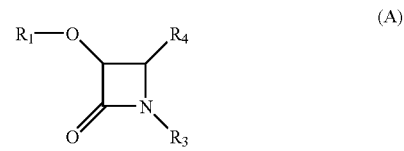

in which $R_1$ is a hydrocarbon group having 1-8 carbon atoms; $R_3$ is an —S-alkyl or —S-aryl wherein the alkyl or aryl group has 1-12 carbon atoms; and $R_4$ is cycloalkyl, heterocycloalkyl, cycloalkenyl, or heterocycloalkenyl, any of which can be optionally substituted with $R_2$, wherein $R_2$ is one or more halides, hydroxyl, nitro, cyano, alkyl, alkenyl, alkynyl, aryl, heteroaryl, cycloalkyl, heterocycloalkyl, cycloalkenyl, heterocycloalkenyl, alkoxy, amido, amino, —$CO_2$alkyl, wherein the alkyl group has 1-10 carbon atoms, CHO, COOH, or COX, wherein X is Cl, F, Br, or I; or a pharmaceutically acceptable salt thereof, in an amount effective to induce or inhibit said event.

2. The method according to claim 1, wherein said cell is from a mammal.

3. The method according to claim 1, wherein said cell is from a human.

4. The method according to claim 1, wherein $R_1$ of said compound is an alkyl group having 1-6 carbon atoms.

5. The method according to claim 1, wherein $R_2$ of said compound is a halide or halides and is selected from Cl, Br, or F.

6. The method according to claim 1, wherein $R_3$ of said compound is an alkylthio or an arylthio group having 1-12 carbon atoms.

7. A method for inducing a cellular event selected from the group consisting of cell death, caspase cascade activation, mitochondrial cytochrome C release into cytoplasm, damage to DNA of a cell, and p38 MAP kinase activation, or for inhibiting an event selected from the group consisting of cell proliferation and DNA replication, said method comprising contacting or exposing a cell to an N-thiolated β-lactam compound having the structure of:

3

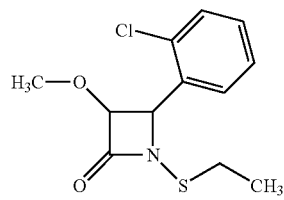

4

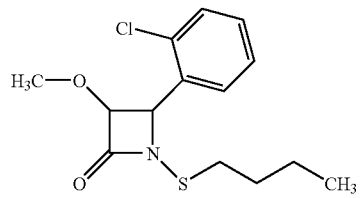

8

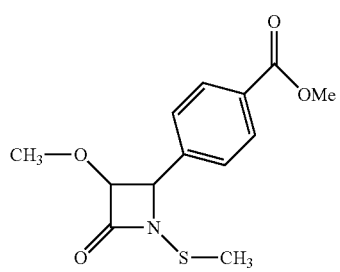

7

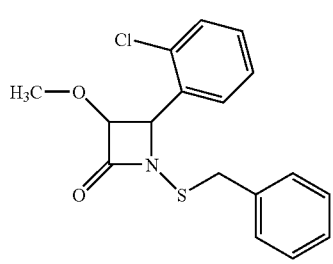

-continued

22

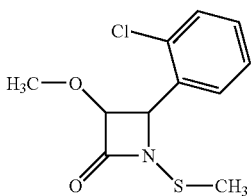

23

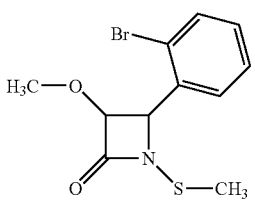

24

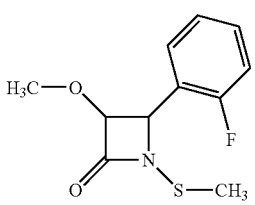

25

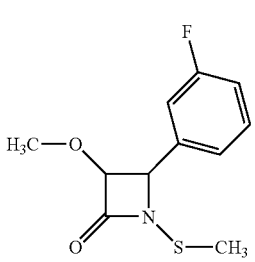

26

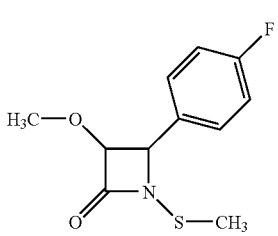

27

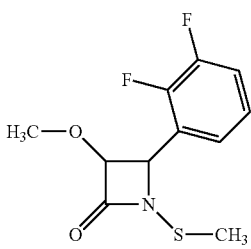

28

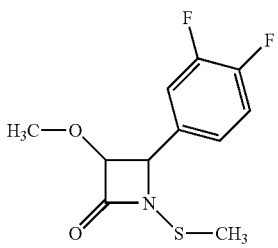

-continued

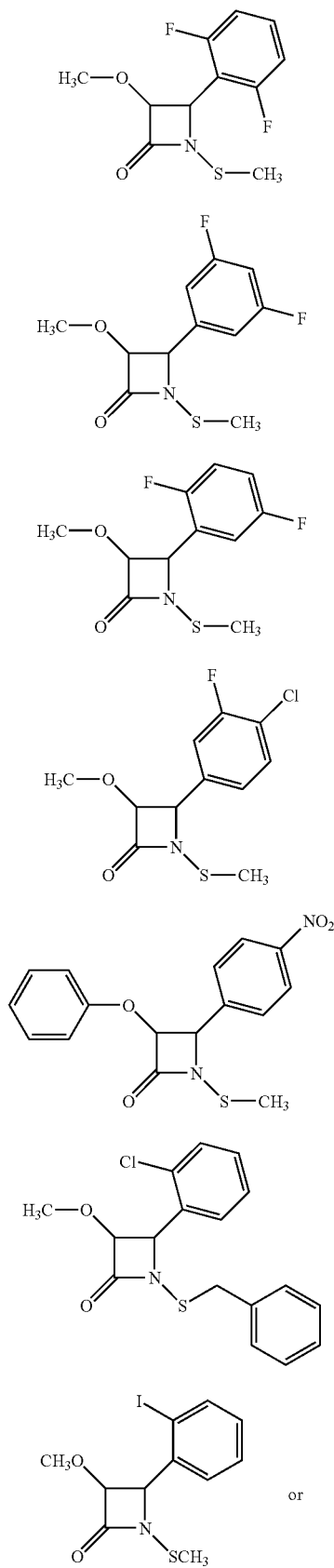

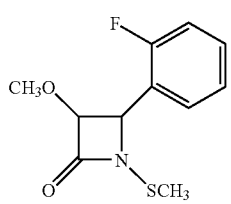

or a pharmaceutically acceptable salt of any said compounds.

8. The method according to claim 7, wherein the N-thiolated β-lactam compound is:

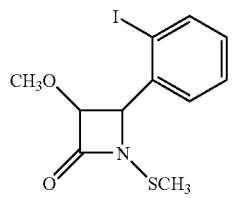

or a pharmaceutically acceptable salt thereof.

9. The method according to claim 7, wherein the N-thiolated β-lactam compound is:

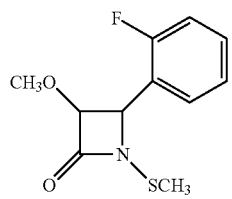

or a pharmaceutically acceptable salt thereof.

10. The method according to claim 1, wherein $R_1$ of said compound is a methyl group.

11. The method according to claim 7, wherein the N-thiolated β-lactam compound is:

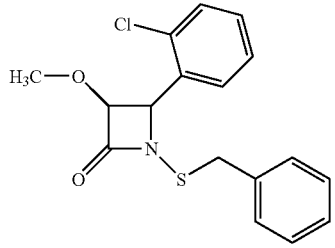

or a pharmaceutically acceptable salt thereof.

12. The method according to claim 1, wherein $R_4$ of said compound is, heterocycloalkyl or heterocycloalkenyl any of which can be substituted with $R_2$.

13. The method according to claim 7, wherein the N-thiolated β-lactam compound is:

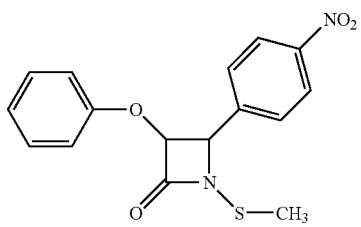

or a pharmaceutically acceptable salt thereof.

14. The method according to claim 1, wherein said cell is a tumor cell or cancer cell.

15. The method according to claim 4, wherein $R_1$ is a methyl group.

16. The method according to claim 4, wherein $R_4$ is heterocycloalkyl or heterocycloalkenyl any of which can be substituted with $R_2$.

17. The method according to claim 15, wherein $R_2$ is a halide or halides and is selected from Cl, Br, or F.

18. The method according to claim 16, wherein $R_2$ is a halide or halides and is selected from Cl, Br, or F.

19. The method according to claim 1, wherein $R_3$ is $-S(CH_2)_nCH_3$, wherein n=0 to 3.

20. The method according to claim 19, wherein $R_3$ is $-SCH_3$.

21. The method according to claim 1, wherein $R_3$ is $-S(CH_2)_n$phenyl, wherein n=0 to 1.

22. The method according to claim 21, wherein $R_3$ is $-SCH_2$phenyl.

23. The method according to claim 7, wherein the N-thiolated β-lactam compound is:

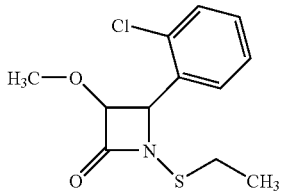

or a pharmaceutically acceptable salt thereof.

24. The method according to claim 7, wherein the N-thiolated β-lactam compound is:

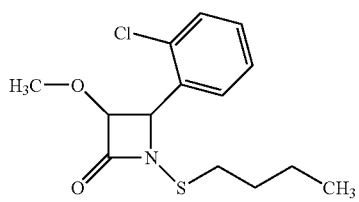

or a pharmaceutically acceptable salt thereof.

25. The method according to claim 7, wherein the N-thiolated β-lactam compound is:

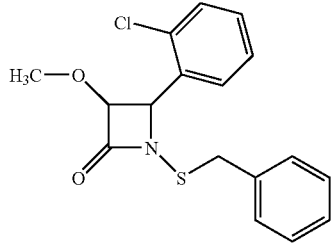

or a pharmaceutically acceptable salt thereof.

26. The method according to claim 7, wherein the N-thiolated β-lactam compound is:

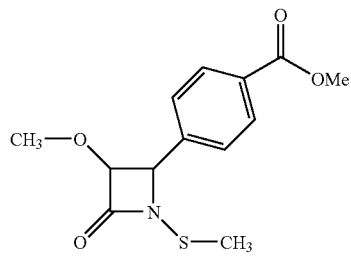

or a pharmaceutically acceptable salt thereof.

27. The method according to claim 7, wherein the N-thiolated β-lactam compound is:

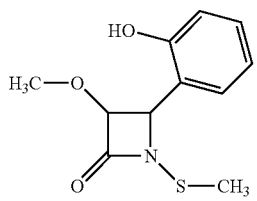

or a pharmaceutically acceptable salt thereof.

28. The method according to claim 7, wherein the N-thiolated β-lactam compound is:

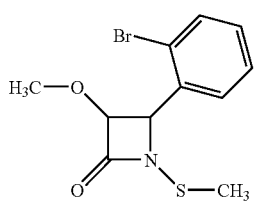

or a pharmaceutically acceptable salt thereof.

29. The method according to claim 7, wherein the N-thiolated β-lactam compound is:

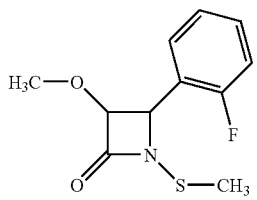

or a pharmaceutically acceptable salt thereof.

30. The method according to claim 7, wherein the N-thiolated β-lactam compound is:

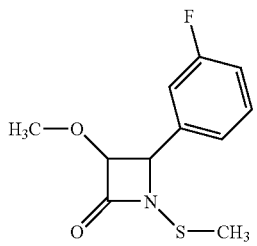

or a pharmaceutically acceptable salt thereof.

31. The method according to claim 7, wherein the N-thiolated β-lactam compound is:

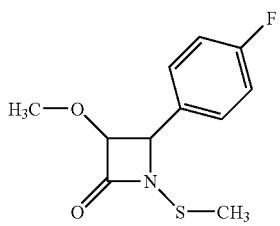

or a pharmaceutically acceptable salt thereof.

32. The method according to claim 7, wherein the N-thiolated β-lactam compound is:

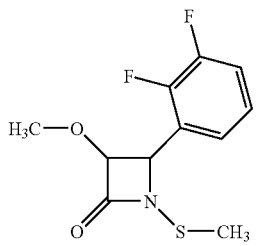

or a pharmaceutically acceptable salt thereof.

33. The method according to claim 7, wherein the N-thiolated β-lactam compound is:

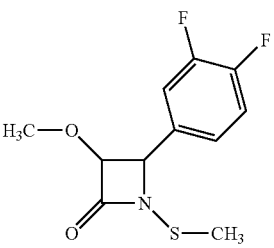

or a pharmaceutically acceptable salt thereof.

34. The method according to claim 7, wherein the N-thiolated β-lactam compound is:

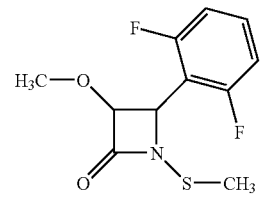

or a pharmaceutically acceptable salt thereof.

35. The method according to claim 7, wherein the N-thiolated β-lactam compound is:

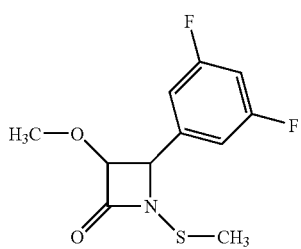

or a pharmaceutically acceptable salt thereof.

36. The method according to claim 7, wherein the N-thiolated β-lactam compound is:

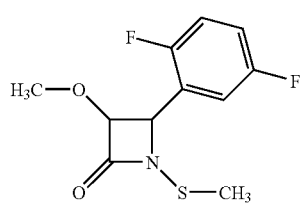
or a pharmaceutically acceptable salt thereof.
37. The method according to claim 7, wherein the N-thiolated β-lactam compound is:
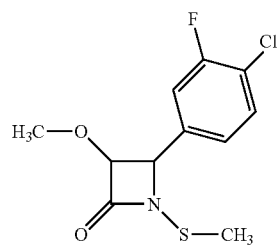
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 7,635,693 B2 | Page 1 of 1 |
| APPLICATION NO. | : 11/374814 | |
| DATED | : December 22, 2009 | |
| INVENTOR(S) | : Q. Ping Dou, Edward Turos and David M. Smith | |

It is certified that error appears in the above-identified patent and that said Letters Patent is hereby corrected as shown below:

Column 2,
Line 3, "Thomberry" should read --Thornberry--.

Column 4,
Line 38, "cells in $G_1$, S, G2 and" should read --cells in $G_1$, S, $G_2$ and--.

Column 7,
Line 5, "ofVa-13" should read --of Va-13--.

Column 13,
Lines 3-4, "carboxylate.    should read --carboxylate. The Use of--.
          The Use of"

Column 21,
Line 38, "355/460 rAM" should read --355/460 nM--.

Signed and Sealed this

Twenty-third Day of February, 2010

David J. Kappos
*Director of the United States Patent and Trademark Office*